(12) United States Patent
Miao et al.

(10) Patent No.: US 9,981,046 B2
(45) Date of Patent: May 29, 2018

(54) DRUG-CONJUGATES, CONJUGATION METHODS, AND USES THEREOF

(71) Applicant: CONCORTIS BIOSYSTEMS, CORP, San Diego, CA (US)

(72) Inventors: Zhenwei Miao, San Diego, CA (US); Yufeng Hong, San Diego, CA (US); Tong Zhu, San Diego, CA (US)

(73) Assignee: Concortis Biosystems, Corp., a wholly owned subsidiary of Sorrento Therapeutics, Inc., San Diego, CA (US)

( * ) Notice: Subject to any disclaimer, the term of this patent is extended or adjusted under 35 U.S.C. 154(b) by 45 days.

(21) Appl. No.: 14/401,115

(22) PCT Filed: May 14, 2013

(86) PCT No.: PCT/US2013/041027
§ 371 (c)(1),
(2) Date: Nov. 13, 2014

(87) PCT Pub. No.: WO2013/173392
PCT Pub. Date: Nov. 21, 2013

(65) Prior Publication Data
US 2016/0067350 A1    Mar. 10, 2016

Related U.S. Application Data

(60) Provisional application No. 61/647,300, filed on May 15, 2012, provisional application No. 61/648,532, filed on May 17, 2012, provisional application No. 61/648,406, filed on May 17, 2012, provisional application No. 61/652,512, filed on May 29, 2012.

(51) Int. Cl.
| | |
|---|---|
| *C07D 241/04* | (2006.01) |
| *A61K 47/48* | (2006.01) |
| *C07D 207/08* | (2006.01) |
| *C07D 207/09* | (2006.01) |
| *C07D 277/593* | (2006.01) |
| *C07D 401/12* | (2006.01) |
| *C07D 403/12* | (2006.01) |
| *C07F 5/02* | (2006.01) |
| *C07K 5/06* | (2006.01) |
| *A61K 38/07* | (2006.01) |
| *A61K 47/68* | (2017.01) |

(52) U.S. Cl.
CPC ........ *A61K 47/48584* (2013.01); *A61K 38/07* (2013.01); *A61K 47/6803* (2017.08); *A61K 47/6811* (2017.08); *A61K 47/6849* (2017.08); *A61K 47/6855* (2017.08); *A61K 47/6889* (2017.08); *C07D 207/08* (2013.01); *C07D 207/09* (2013.01); *C07D 277/593* (2013.01); *C07D 401/12* (2013.01); *C07D 403/12* (2013.01); *C07F 5/025* (2013.01); *C07K 5/06008* (2013.01)

(58) Field of Classification Search
None
See application file for complete search history.

(56) References Cited

U.S. PATENT DOCUMENTS

| | | |
|---|---|---|
| 5,780,588 A | 7/1998 | Pettit et al. |
| 6,124,431 A | 9/2000 | Sakakibara et al. |
| 6,569,834 B1 | 5/2003 | Pettit et al. |
| 7,531,162 B2 | 5/2009 | Collins et al. |
| 7,767,205 B2 | 8/2010 | Mao et al. |
| 7,829,531 B2 | 11/2010 | Senter et al. |
| 7,994,135 B2 | 8/2011 | Doronina et al. |
| 8,088,387 B2 | 1/2012 | Steeves et al. |
| 8,470,984 B2 | 6/2013 | Caruso et al. |
| 2005/0238649 A1 | 10/2005 | Doronina et al. |
| 2006/0128754 A1 | 6/2006 | Hoeft et al. |
| 2007/0092940 A1 | 4/2007 | Eigenbrot et al. |
| 2007/0134243 A1 | 6/2007 | Gazzard et al. |
| 2011/0206658 A1 | 8/2011 | Crowley et al. |
| 2011/0217321 A1 | 9/2011 | Torgov et al. |
| 2011/0245295 A1 | 10/2011 | Chai et al. |
| 2011/0263650 A1 | 10/2011 | Ellman et al. |
| 2011/0268751 A1 | 11/2011 | Sievers et al. |
| 2011/0301334 A1 | 12/2011 | Bhakta et al. |
| 2012/0148610 A1 | 6/2012 | Doronina et al. |
| 2013/0029900 A1 | 1/2013 | Widdison |
| 2013/0101546 A1 | 4/2013 | Yurkovetskiy et al. |
| 2013/0224228 A1 | 8/2013 | Jackson et al. |
| 2014/0030282 A1 | 1/2014 | Polakis et al. |
| 2015/0105539 A1 | 4/2015 | Miao et al. |

(Continued)

FOREIGN PATENT DOCUMENTS

| | | |
|---|---|---|
| CA | 2813056 A1 | 4/2012 |
| EP | 0624377 A2 | 11/1994 |
| JP | 2011515069 A | 5/2011 |
| JP | 2015-500287 A | 1/2015 |
| WO | 2005/081711 A2 | 9/2005 |
| WO | 2007/109567 A1 | 9/2007 |
| WO | 2008/112873 A2 | 9/2008 |
| WO | 2010/009124 A2 | 1/2010 |
| WO | 2012/010287 A1 | 1/2012 |
| WO | 2012/166559 A1 | 12/2012 |
| WO | 2012/166560 A1 | 12/2012 |
| WO | 2013/085925 A1 | 6/2013 |

(Continued)

OTHER PUBLICATIONS

"Antibody structure", http://www.biology.arizona.edu/immunology/tutorials/antibody/structure.html, accessed Sep. 8, 2016.*

(Continued)

*Primary Examiner* — Noble E Jarrell
(74) *Attorney, Agent, or Firm* — Womble Bond Dickinson (US) LLP; Danielle L. Herritt

(57) ABSTRACT

In one aspect, an active agent-conjugate, methods of preparing the active agent-conjugate, and uses thereof is provided.

2 Claims, 16 Drawing Sheets

(56) References Cited

U.S. PATENT DOCUMENTS

2015/0105540 A1    4/2015  Miao et al.
2015/0141646 A1    5/2015  Miao et al.

FOREIGN PATENT DOCUMENTS

| WO | 2013/173392 A1 | 11/2013 |
| WO | 2013/173393 A1 | 11/2013 |
| WO | 2103/173391 A1 | 11/2013 |
| WO | 2013/185117 A1 | 12/2013 |
| WO | 2013/192360 A1 | 12/2013 |
| WO | 2015/057876 A1 | 4/2015 |
| WO | 2016/123412 A1 | 8/2016 |
| WO | 2016/127081 A1 | 8/2016 |

OTHER PUBLICATIONS

Dosio et al., "Synthesis of Different Immunotoxins Composed by Ribosome Inactivating Proteins Non-Covalently Bound to Monoclonal Antibody" Il Farmaco, vol. 51, Issue 7, 1996, pp. 477-482.
Geroni et al., "Nemorubicin: A Doxorubicin-like Structure with a Novel Mechanism of Action Different from Anthracyclines" Proc. Amer. Assoc. Cancer Reserach, vol. 47, Abstract No. 3845, 2006.
Cella, R., et al., "Steroselective Synthesis of the Dolastatin Units by Organotriflouroborates Additions to Alpha-Amino Aldehydes", Tetrahedron Letters, 49 (2008) 16-19.
Ducry, L. et al., "Antibody-Drug Conjugates: Linking Cytotoxic Payloads to Monoclonal Antibodies" Bioconjugate Chemistry, 2010, vol. 21, No. 1, pp. 5-13.
Kingston, David "Tubulin Interactive Natural Products as Anticancer Agents" J Nat Prod. Mar. 2009; 72(3): 507-515.
Pettit, et al., "Specific Activities of Dolastatin 10 and Peptide Derivatives Against Crypococcus neoformans" Antimicrobial Agents and Chemotherapy, Nov. 1998, p. 2961-2965.
PubChemCompound datasheet (online compound summary) CID 56841603; Create Date: Mar. 21, 2012; http://pubchem.ncbi.nlm.nih.gov/summary/summary.cgi?cid=56841603.
Younes, A. et al., "Brentuximab Vedotin (SGN-35) for Relapsed CD30-Positive Lymphomas" The New England Journal of Medicine, 363; 19, 2010, 1812-1821.
U.S. Appl. No. 14/401,114, filed Nov. 13, 2014.
U.S. Appl. No. 14/401,318, filed Nov. 14, 2014.
U.S. Appl. No. 14/515,352, filed Oct. 15, 2014.
U.S. Appl. No. 15/009,775, filed Jan. 28, 2016.
U.S. Appl. No. 15/017,174, filed Feb. 5, 2016.
Tannock et al., The Basic Science of Oncology, Ch. 19—Experimental Chemotherapy, p. 338 and p. 352-359, New York, 1992.
Pettit, G. et al., "Antineoplastic Agents. 592. Highly Effective Cancer Cell Growth Inhibitory Structural Modifications of Dolastatin 10" Jouranl of Natual Products, 2011, 74, 962-968.
J.Am. Chem. Soc., 2010, 132, p. 1960-1965.

\* cited by examiner

DRUG-CONJUGATES, CONJUGATION METHODS, AND USES THEREOF

BACKGROUND

Recently, it has been found that an antibody (or antibody fragment such as a single-chain variable fragment) can be linked to a payload drug to form an immunoconjugate that has been termed antibody-drug conjugate, or ADC. The antibody causes the ADC to bind to the target cells. Often the ADC is then internalized by the cell and the drug is released to treat the cell. Because of the targeting, the side effects may be lower than the side effects of systemically administering the drug.

SUMMARY

Some embodiments provide active agent-conjugates, methods of preparing active agent-conjugates, and uses thereof.

Some embodiments provide an active agent-conjugate having the structure of Formula I:

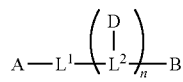
(I)

or a pharmaceutically acceptable salt thereof,
wherein:
A is a targeting moiety;
B is an auxiliary moiety that optionally includes a second targeting moiety, or B is null;
$L^1$ includes a group including at least one N (nitrogen) atom;
each D is independently selected, where each D includes an active agent;
each $L^2$ is independently a linker, wherein at least one $L^2$ links to $L^1$; and
n is 1, 2, 3, 4, 5, 6, 7, 8, 9, or 10. In some embodiments, $L^1$ includes —C(=O)—.

Some embodiments provide an active agent-conjugate having the structure of Formula Ia:

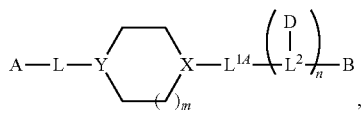
(Ia)

or a pharmaceutically acceptable salt thereof,
wherein:
A is a targeting moiety; B is an auxiliary moiety that optionally includes a second targeting moiety, or B is null; each D is independently selected, where each D includes an active agent; each $L^2$ is independently a linker; n is 1, 2, 3, 4, 5, 6, 7, 8, 9, or 10; X is N (nitrogen) or CH; Y is N (nitrogen), or CH; m is 0, 1, or 2; L is a linker, or null; and $L^{1A}$ is a linker, or null.

Some embodiments provide an active agent-conjugate having the structure of Formula Iaa:

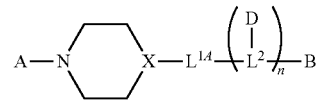
(Iaa)

or a pharmaceutically acceptable salt thereof,
wherein:
A is a targeting moiety; B is an auxiliary moiety that optionally includes a second targeting moiety, or B is null; each D is independently selected, where each D includes an active agent; each $L^2$ is independently a linker; n is 1, 2, 3, 4, 5, 6, 7, 8, 9, or 10; X is N (nitrogen) or CH; and $L^{1A}$ is a linker, or null.

Some embodiments provide an active agent-conjugate having the structure of Formula Iab:

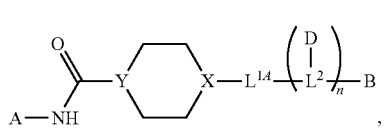
(Iaa)

or a pharmaceutically acceptable salt thereof,
wherein:
A is a targeting moiety; B is an auxiliary moiety that optionally includes a second targeting moiety, or B is null; each D is independently selected, where each D includes an active agent; each $L^2$ is independently a linker; n is 1, 2, 3, 4, 5, 6, 7, 8, 9, or 10; X is N (nitrogen) or CH; and $L^{1A}$ is a linker, or null.

Some embodiments provide a method of chemical synthesis comprising:

reacting an amine of formula I-A with a dialdehyde of formula I-B

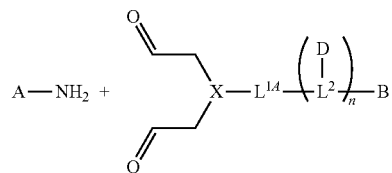

I-A          I-B to provide the active agent-conjugate of Formula Iaa.

Some embodiments provide a method of chemical synthesis comprising:

reacting with a compound of formula II-A with a compound of formula II-B

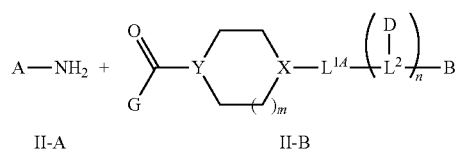

II-A          II-B to provide the active agent-conjugate of Formula Iab.

In some embodiments,

may be:

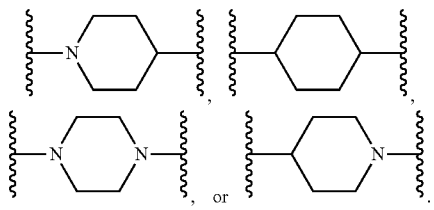

In some embodiments, L comprises —NH—C(=O)—, —NH—C(=O)—NH— or —NH—C(=O)—O—. In some embodiments, L may be —NH—C(=O)—, —NH—C(=O)—NH— or —NH—C(=O)—O—. In some embodiments, L may be null. In some embodiments, L includes —C(=O)—, —NH—C(=O)—, —C(=O)—O—, —NH—C(=O)—NH— or —NH—C(=O)—O—. In some embodiments, L may be —C(=O)—, —NH—C(=O)—, —C(=O)—O—, —NH—C(=O)—NH— or —NH—C(=O)—O—. In some embodiments, L may be —C(=O)—.

In some embodiments, $L^{1A}$ includes —$(CH_2)_n$— where n is 1, 2, 3, 4, 5, 6, 7, 8, 9, or 10. In some embodiments, $L^{1A}$ includes —$(CH_2CH_2O)_n$— where n is 1, 2, 3, 4, 5, 6, 7, 8, 9, or 10. In some embodiments, $L^{1A}$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, $L^{1A}$ includes peptide, oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or combinations thereof.

In some embodiments, the A component comprises a monoclonal antibody (mAB). In some embodiments, the A component comprises an antibody fragment, surrogate, or variant. In some embodiments, the A component comprises a protein ligand. In some embodiments, the A component comprises a protein scaffold. In some embodiments, the A component comprises a peptide. In some embodiments, the A component comprises a small molecule ligand. In some embodiments, the A component comprises at least one modified n-butyl L-α-amino acid residue.

In some embodiments, $L^2$ includes a noncleavable unit. In some embodiments, the noncleavable unit includes —$(CH_2)_n$— where n is 1, 2, 3, 4, 5, 6, 7, 8, 9, or 10. In some embodiments, the noncleavable unit includes —$(CH_2CH_2O)_n$— where n is 1, 2, 3, 4, 5, 6, 7, 8, 9, or 10. In some embodiments, $L^2$ includes a cleavable unit. In some embodiments, the cleavable unit comprises a peptide. In some embodiments, $L^2$ comprises at least one component selected from the group consisting of a peptide, an oligosaccharide, —$(CH_2)$—, O (oxygen), S (sulfur), —NH—, —$(CH_2CH_2O)$—, Val, Cit, PAB, Phe, Lys, D-Val, Leu, Lys, Gly, Ala, Asn, and the like. In some embodiments, $L^2$ includes —$(CH_2)_n$— where n is 1, 2, 3, 4, 5, 6, 7, 8, 9, or 10. In some embodiments, $L^2$ comprises —$(CH_2CH_2O)_n$— where n is 1, 2, 3, 4, 5, 6, 7, 8, 9, or 10. In some embodiments, $L^2$ comprises at least one Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, $L^2$ comprises a peptide oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or combinations thereof.

Some embodiments provide a composition comprising an active agent-conjugate as disclosed and described herein. In some embodiments, >70% of the composition consists of no more than two active components. In some embodiments, >60% of the composition consists of no more than two active components. In some embodiments, >50% of the composition consists of no more than two active components. Some embodiments provide a composition comprising an active agent-conjugate as disclosed and described herein. In some embodiments, >70% of the composition consists of only two active components. In some embodiments, >60% of the composition consists of only two active components. In some embodiments, >50% of the composition consists of only two active components.

DETAILED DESCRIPTION

Figure 1:
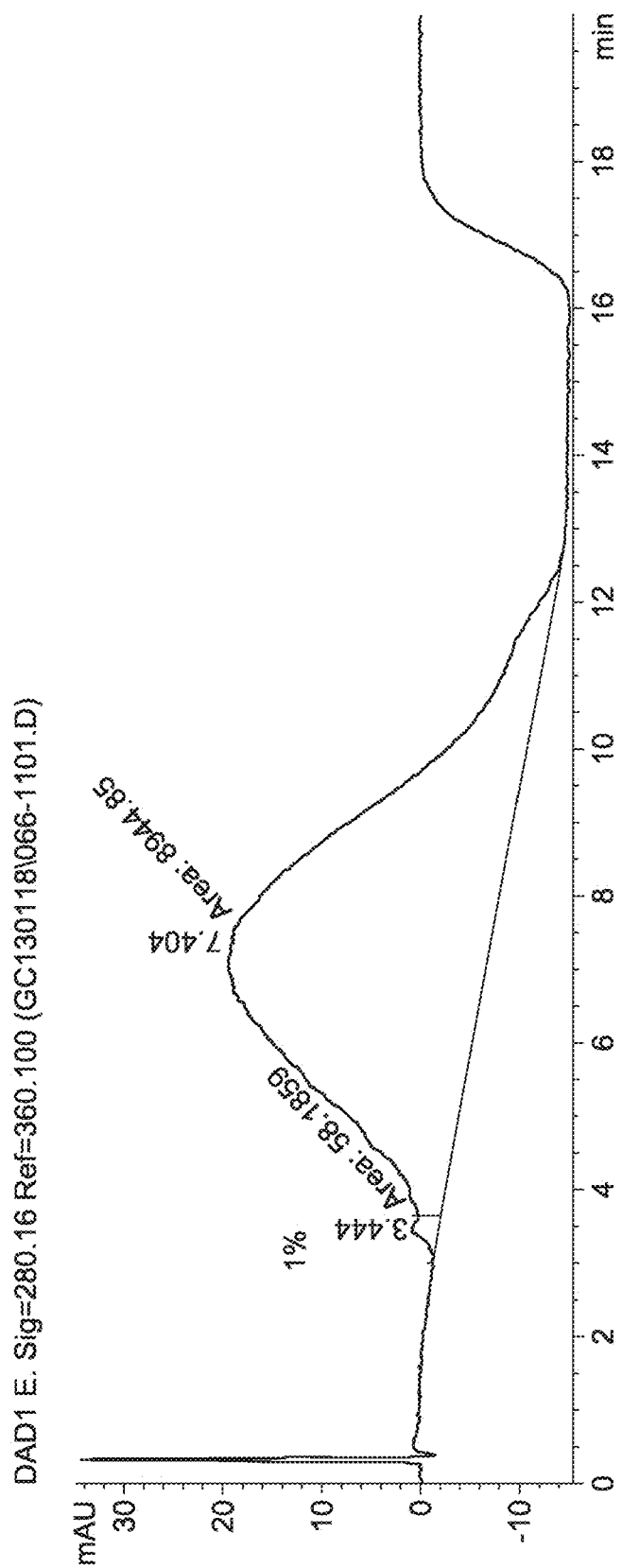
FIG. 1 shows the HIC-HPLC chromatogram product of a conventional trastuzumab-emtansine two-step conjugation reaction.

Some embodiments provide an active agent-conjugate. In some embodiments, the active agent-conjugate is a drug-conjugate. In some embodiments, the drug-conjugate includes a targeting molecule. In some embodiments, the targeting molecule includes a monoclonal antibody (mAB). In some embodiments, the drug-conjugate includes a spacer or a multifunctional linker. In some embodiments, the spacer connects to the mAB by a group including a N (nitrogen) atom. In some embodiments, the multifunctional linker connects to the mAB by a group including a N (nitrogen) atom. In some embodiments, the spacer or multifunctional linker may be optionally connected to an auxiliary moiety. In some embodiments, the auxiliary moiety may be a second targeting molecule such as mAB and peptide. In some embodiments, the auxiliary moiety may be a hydrophilic polymer such as polyethylene glycol (PEG), and the like. In some embodiments, the spacer or multifunctional linker may include a group including a N (nitrogen) atom. In some embodiments, the spacer or multifunctional linker may include a cyclic group including a N (nitrogen) atom.

Conjugation methods to derivatize a polypeptide with a payload can be accomplished by forming an amide bond with a lysine side chain. Due to the presence of large number of lysine side chain amines with similar reactivity, this conjugation strategy can produce very complex heterogeneous mixtures. The compositions and methods provided herein provide conjugation through lysine, where, in some embodiments, enhanced selectivity of the lysine can result in a less heterogenous mixture.

Definitions

As used herein, common organic abbreviations are defined as follows:
Ac Acetyl
aq. Aqueous
BOC or Boc tert-Butoxycarbonyl
BrOP bromo tris(dimethylamino) phosphonium hexafluorophosphate
Bu n-Butyl
° C. Temperature in degrees Centigrade
DCM methylene chloride
DEPC Diethylcyanophosphonate
DIC diisopropylcarbodiimide
DIEA Diisopropylethylamine
DMF N,N'-Dimethylformamide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOAt 1-Hydroxy-7-azabenzotriazole
HOBT N-Hydroxybenzotriazole
HOSu N-Hydroxysuccinimide
HPLC High-performance liquid chromatography
LC/MS Liquid chromatography-mass spectrometry
Me Methyl
MeOH Methanol
MeCN Acetonitrile
mL Milliliter(s)
MS mass spectrometry
RP-HPLC reverse phase HPLC
rt room temperature
t-Bu tert-Butyl
TEA Triethylamine
Tert, t tertiary
TFA Trifluoracetic acid
THF Tetrahydrofuran
THP Tetrahydropyranyl
TLC Thin-Lyser chromatography
µL Microliter(s)

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO₂R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO₂NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO₂R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "urea" group refers to a "—N(R$_A$)C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH₂).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF₃), halo($C_1$-$C_6$)alkoxy (e.g., —OCF₃), $C_1$-$C_6$ alkylthio, arylthio, amino, amino($C_1$-$C_6$)alkyl, nitro, O-carbamyl, N-carbamyl, 0-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH₂—, —CH₂CH₂—, —CH₂CH(CH₃)CH₂—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

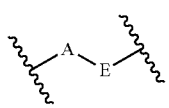

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

Compounds

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element present in a compound either specifically or generically described herein may include any isotope of said element. For example, in a compound specifically or generically described herein a hydrogen atom may be explicitly disclosed or understood to be present in the compound and each such hydrogen atom is any isotope of hydrogen, including but not limited to hydrogen-1 (protium) and hydrogen-2 (deuterium). Thus, reference herein to a compound encompasses all potential isotopic forms unless the context clearly dictates otherwise.

Conjugation Methods, Spacers and Linkers Involved

Some embodiments provide a method of conjugating of a targeting molecule through a spacer or a multifunctional linker. In some embodiments, the spacer or multifunctional linker may include a group including a N (nitrogen) atom. In some embodiments, the method includes a single-step or sequential conjugation approach. In some embodiments, the drug-conjugates include a spacer or a multifunctional linker. In some embodiments, the spacer or multifunctional linker may include a noncleavable or cleavable unit such as a peptide or a disulfide bond.

Utilities and Applications

Some embodiments provide a method of treating a patient in need thereof comprising administering an active agent-conjugate as disclosed and described herein to said patient. In some embodiments, the patient may have cancer, immune diseases, infectious diseases or metabolic diseases such as diabetes.

Some embodiments provide a method of diagnosis or imaging comprising administering an active agent-conjugate as disclosed and described herein to an individual.

Certain Structures

Some embodiments provide an active agent-conjugate having the structure of Formula I

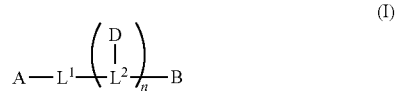

(I)

or a pharmaceutically acceptable salt thereof, wherein:

A may be a targeting moiety;

B is an auxiliary moiety that optionally includes a second targeting moiety, water soluble polymer or B is null;

$L^1$ includes a group including a N (nitrogen) atom;

each D is independently selected, where each D includes an active agent;

each L² is independently a linker, wherein at least one L² links to L¹; and n is 1, 2, 3, 4, 5, 6, 7, 8, 9, or 10.

In some embodiments, A may be a monoclonal antibody (mAB), more specifically, A may be a human antibody, humanized antibody or a chimeric antibody.

In some embodiments, A may be an antibody fragment, surrogate, or variant.

In some embodiments, A may be a protein ligand.

In some embodiments, A may be a protein scaffold.

In some embodiments, A may be a peptide.

In some embodiments, A may be a small molecule ligand.

In some embodiments, B may be a hydrophilic polymer. In some embodiments, the hydrophilic polymer may polyethylene glycol (PEG), and the like. In some embodiments, B may be a biodegradable polymer. In some embodiments, the biodegradable polymer may be unstructured proteins polyamino acids, polypeptides polysaccharides and combinations thereof.

In some embodiments, B may be a monoclonal antibody (mAB).

In some embodiments, B may be an antibody fragment, surrogate, or variant.

In some embodiments, B may be a protein ligand.

In some embodiments, B may be a protein scaffold.

In some embodiments, B may be a peptide.

In some embodiments, B may be RNA or DNA.

In some embodiments, B may be a RNA or DNA fragment.

In some embodiments, B may be a small molecule ligand.

In some embodiments, D may be a biologically active compound.

In some embodiments, D may be a drug.

In some embodiments, D may be a chemotherapy drug.

In some embodiments, D may be a natural product.

In some embodiments, D may be an immune modulator.

In some embodiments, D may be a tubulin-binder.

In some embodiments, D may be a DNA-alkylating agent.

In some embodiments, D may be an RNA polymerase inhibitor.

In some embodiments, D may be a DNA topoisomerase inhibitor.

In some embodiments, D may be an anti-epigenetic agent.

In some embodiments, D may be a protein synthesis inhibitor.

In some embodiments, D may be an anti-metabolism agent.

In some embodiments, D may be an enzyme inhibitor.

In some embodiments, D may be a peptide.

In some embodiments, D may be a peptidomimetic.

In some embodiments, D may be a siRNA.

In some embodiments, D may be an antisense DNA.

In some embodiments, D may be a DNA intercalactor.

In some embodiments, L² may include a spacer or a multifunctional linker. In some embodiments, L² may include a spacer and a multifunctional linker. In some embodiments, L² may include a multifunctional linker. In some embodiments, each L² may be a linker, wherein the linker may be cleavable or non-cleavable under biological conditions. In some embodiments, the linker may be cleavable by an enzyme. In some embodiments, L² may include Linker.

In some embodiments, L¹ includes a cyclic group including at least one N (nitrogen) atom. In some embodiments, L¹ includes a cyclic group including at least two N (nitrogen) atoms. In some embodiments, L¹ includes a cyclic group including at least one N (nitrogen) atom and a spacer. In some embodiments, L¹ includes a cyclic group including at least two N (nitrogen) atoms and a spacer. In some embodiments, the spacer connects to the mAB by an amide bond. In some embodiments, the spacer connects to the mAB through an amine bond.

In some embodiments, A comprises at least one modified n-butyl L-α-amino acid. In some embodiments, at least one modified L-Lysine residue is from an L-Lysine residue of a peptide before conjugation. In some embodiments, at least one nitrogen of L¹ is from an at least one modified n-butyl L-α-amino acid of a peptide before conjugation. In some embodiments, A and L¹ together comprise at least one modified L-Lysine residue. In some embodiments, the terminal nitrogen of the side chain of an L-Lysine residue of a peptide before conjugation is the at least one N (nitrogen) atom of L¹. In some embodiments, A comprises the —(CH₂)₄— of the side chain of an L-Lysine residue of a peptide before conjugation that provides the at least one N (nitrogen) atom of L¹. In some embodiments, A comprises a modified n-butyl α-amino acid residue.

In some embodiments, Linker may be a peptide.

In some embodiments, Linker may include an oligosaccharide. For example, Linker may include chitosan. In some embodiments, L² may include Linker and —(CH₂)ₙ— where n is 1, 2, 3, 4, 5, 6, 7, 8, 9, or 10. In some embodiments, L² may include Linker and —(CH₂CH₂O)ₙ— where n is 1, 2, 3, 4, 5, 6, 7, 8, 9, or 10.

In some embodiments, Linker may include —(CH₂)ₙ— where n is 1, 2, 3, 4, 5, 6, 7, 8, 9, or 10.

In some embodiments, Linker may include —(CH₂CH₂O)ₙ— where n is 1, 2, 3, 4, 5, 6, 7, 8, 9, or 10.

In some embodiments, Linker may include Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB, or the like.

In some embodiments, Linker may include any combination of peptide, oligosaccharide, —(CH₂)ₙ—, —(CH₂CH₂O)ₙ—, Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB, and the like.

In some embodiments, the spacer may include a peptide.

In some embodiments, the spacer may include an oligosaccharide. For example, the spacer may include chitosan.

In some embodiments, the spacer may include —(CH₂)ₙ— where n is 1, 2, 3, 4, 5, 6, 7, 8, 9, or 10. In some embodiments, L¹ may include a component including a 4-carbon bridge and —(CH₂)ₙ— where n is 1, 2, 3, 4, 5, 6, 7, 8, 9, or 10.

In some embodiments, the spacer may include —(CH₂CH₂O)ₙ— where n is 1, 2, 3, 4, 5, 6, 7, 8, 9, or 10. In some embodiments, L¹ may include a component including a 4-carbon bridge and —(CH₂CH₂O)ₙ— where n is 1, 2, 3, 4, 5, 6, 7, 8, 9, or 10.

In some embodiments, the spacer may include Val-Cit-PAB, Val-Ala-PAB, Val-Lys(Ac)-PAB, Phe-Lys-PAB, Phe-Lys(Ac)-PAB, Ala-Ala-Asn-PAB, Ala-PAB, PAB, or the like.

In some embodiments, the spacer may be any combination of peptide, oligosaccharide, —(CH₂)ₙ—, —(CH₂CH₂O)ₙ—, Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB, and the like.

In some embodiments, L¹ may include, but is not limited to,

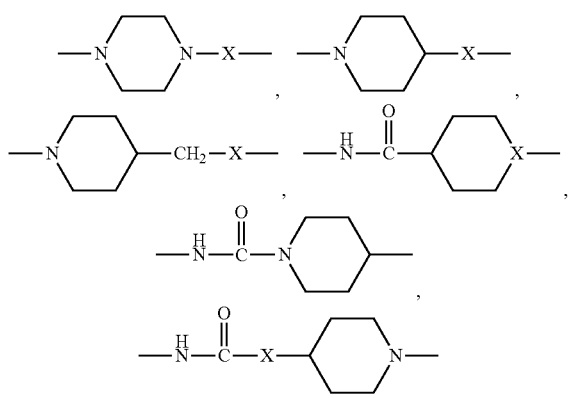

and the like.

In some embodiments, the agent-conjugate having the structure of Formula I has the structure of Formula Ia:

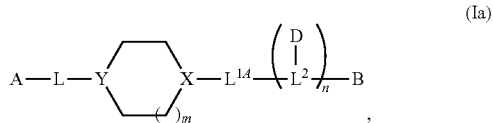

or a pharmaceutically acceptable salt thereof, wherein X is N (nitrogen), CH— or CH—C(=O)—. Y is N (nitrogen), CH— or CH—CH2-. m may be 0, 1, or 2; and $L^{14}$ may be a linker, or null; L is but not limited to —NH—C(=O)—, —NH—C(=O)—NH— or —NH—C(=O)—O—.

In some embodiments, the A component comprises a monoclonal antibody (mAB). In some embodiments, the A component comprises an antibody fragment, surrogate, or variant. In some embodiments, the A component comprises a protein ligand. In some embodiments, the A component comprises a protein scaffold. In some embodiments, the A component comprises a peptide. In some embodiments, the A component comprises a small molecule ligand. In some embodiments, the A component comprises at least one modified L-Alanine residue. In some embodiments, the A component comprises at least two modified L-Alanine residues. In some embodiments, at least one $L^2$ includes —(CH$_2$)$_n$— where n is 1, 2, 3, 4, 5, 6, 7, 8, 9, or 10. In some embodiments, at least one $L^2$ includes —(CH$_2$CH$_2$O)$_n$— where n is 1, 2, 3, 4, 5, 6, 7, 8, 9, or 10. In some embodiments, at least one $L^2$ includes Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB. In some embodiments, at least one $L^2$ includes a peptide, an oligosaccharide, —(CH$_2$)$_n$—, —(CH$_2$CH$_2$O)$_n$—, Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB, or combinations thereof. In some embodiments, $L^1$ includes —C(=O)—. In some embodiments, $L^1$ includes —C(=O)—, —NH—C(=O)—, —C(=O)—O—, —NH—C(=O)—NH— or —NH—C(=O)—O—. In some embodiments, $L^1$ may be —C(=O)—, —NH—C(=O)—, —C(=O)—O—, —NH—C(=O)—NH— or —NH—C(=O)—O—. In some embodiments, $L^1$ is —C(=O)—. In some embodiments, at least one $L^2$ includes:

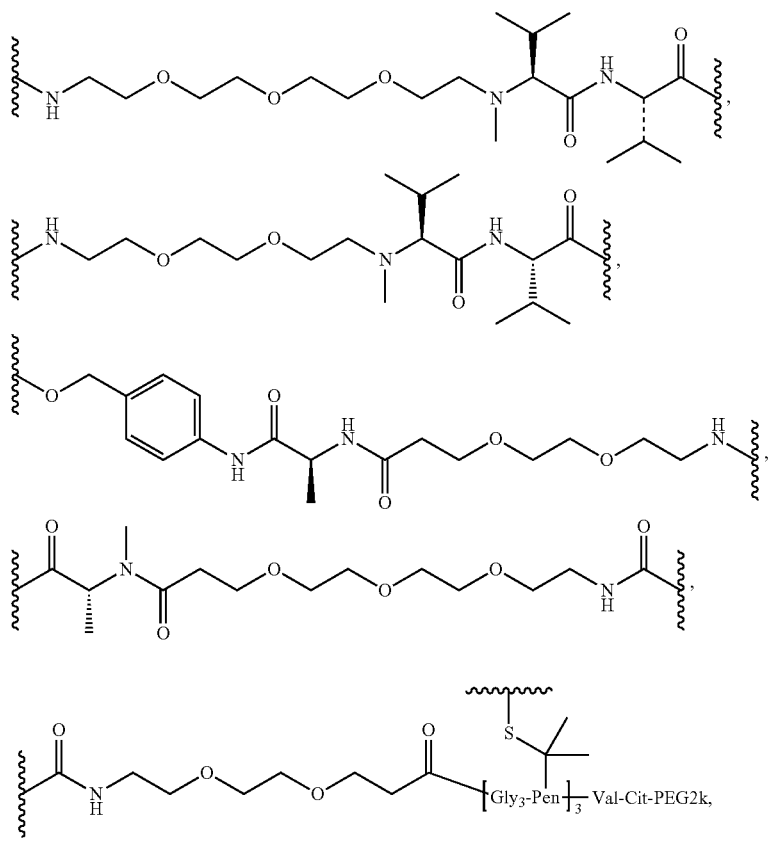

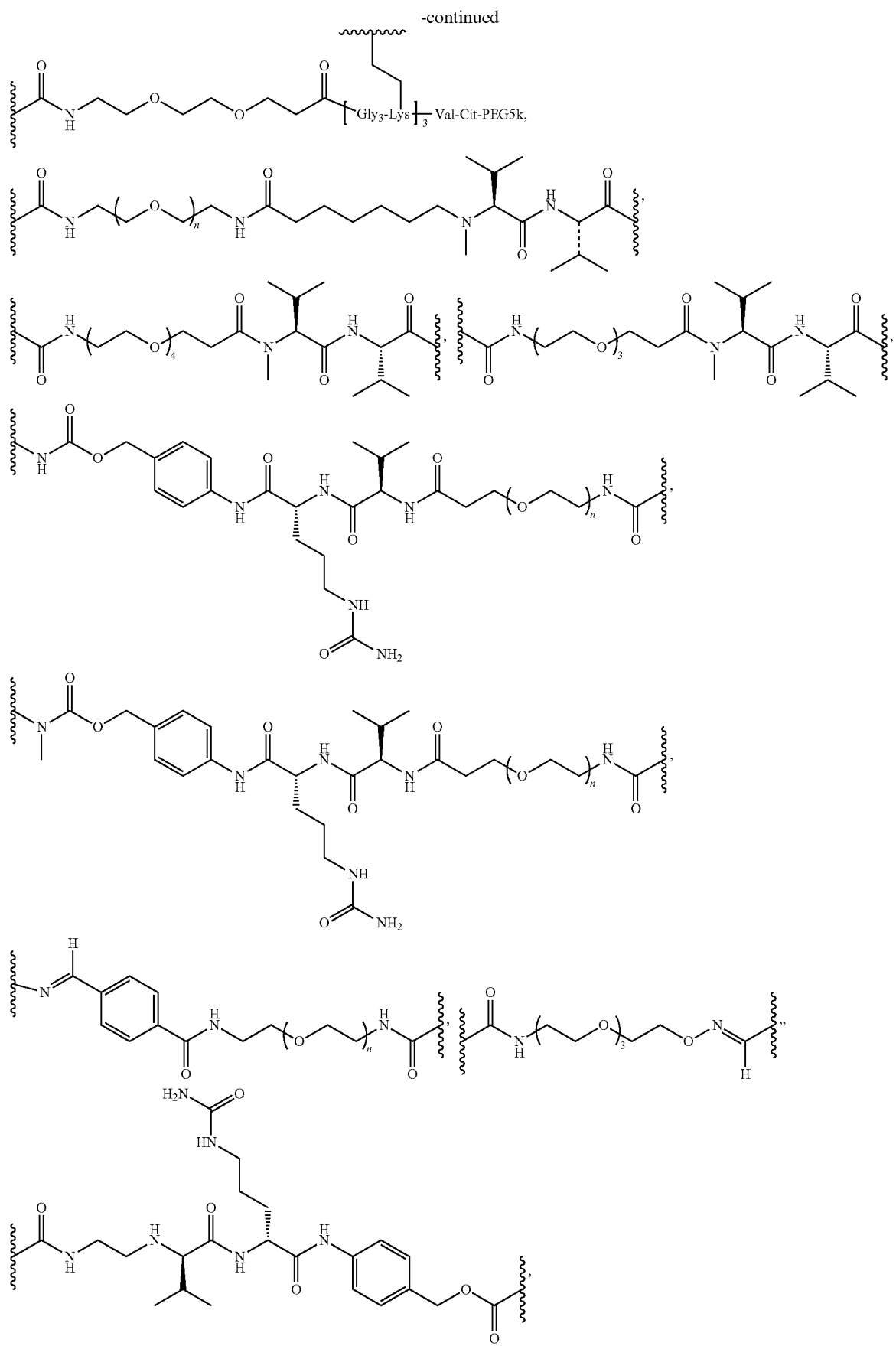

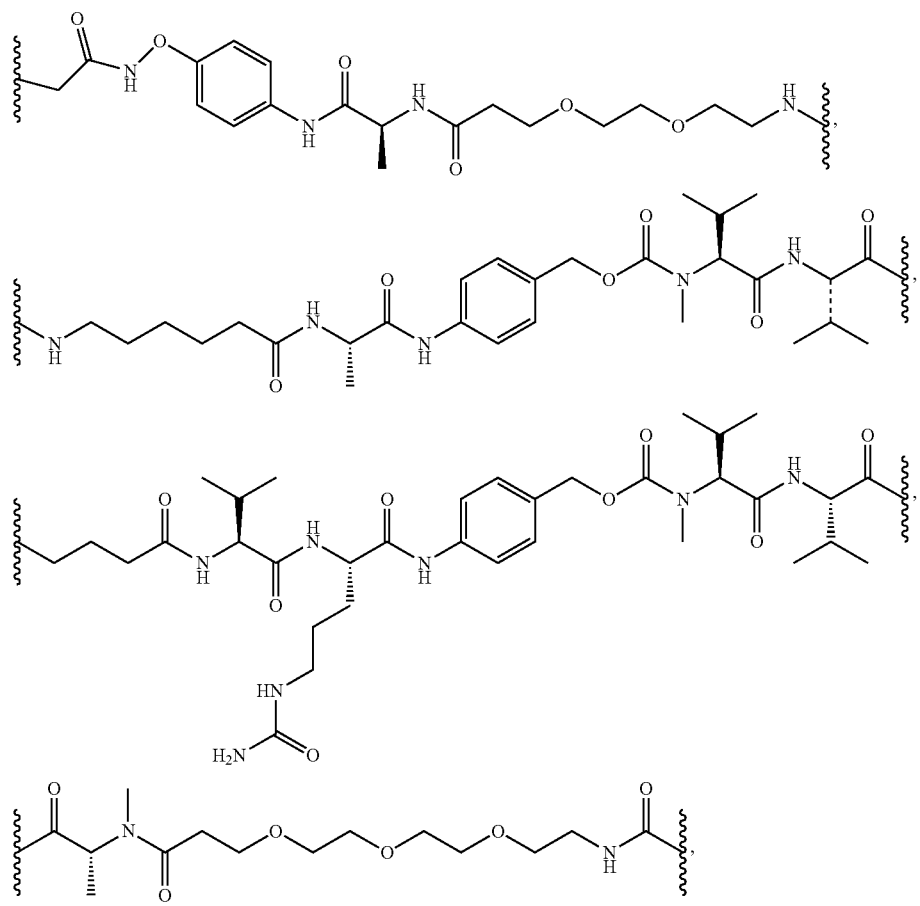
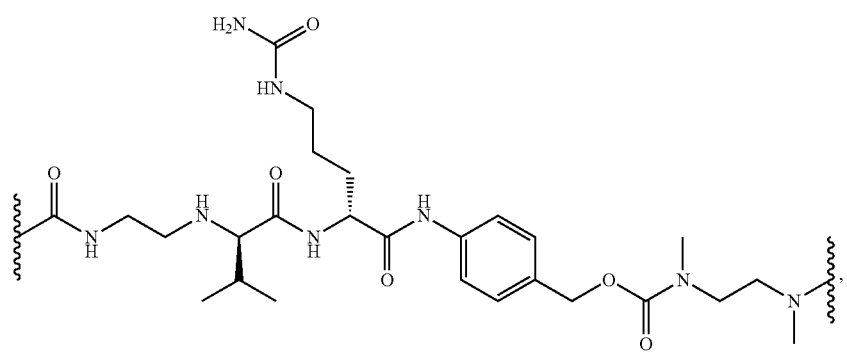
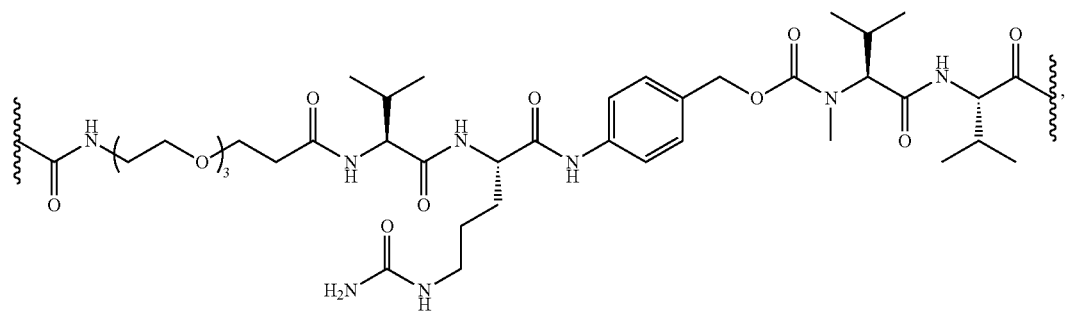

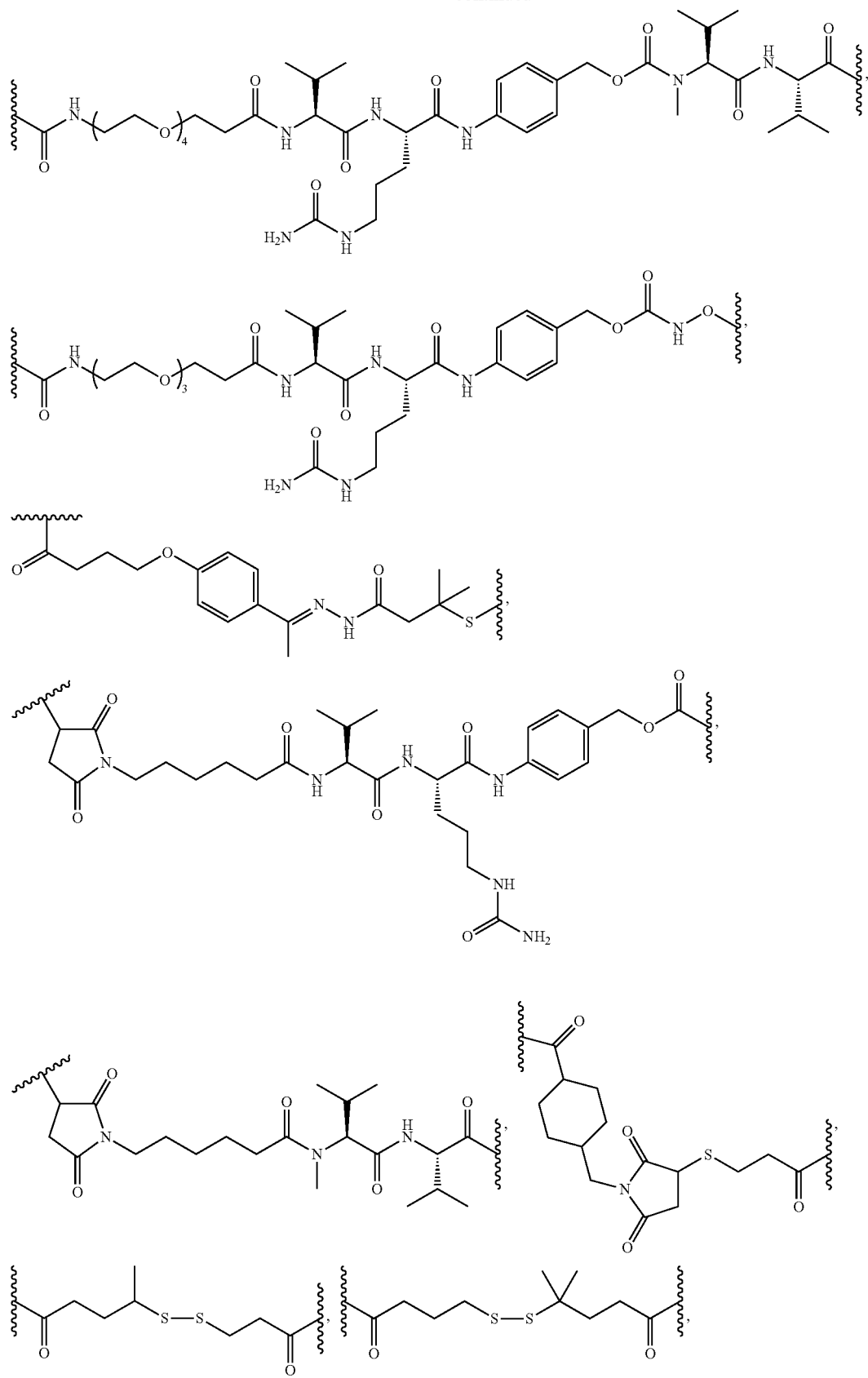

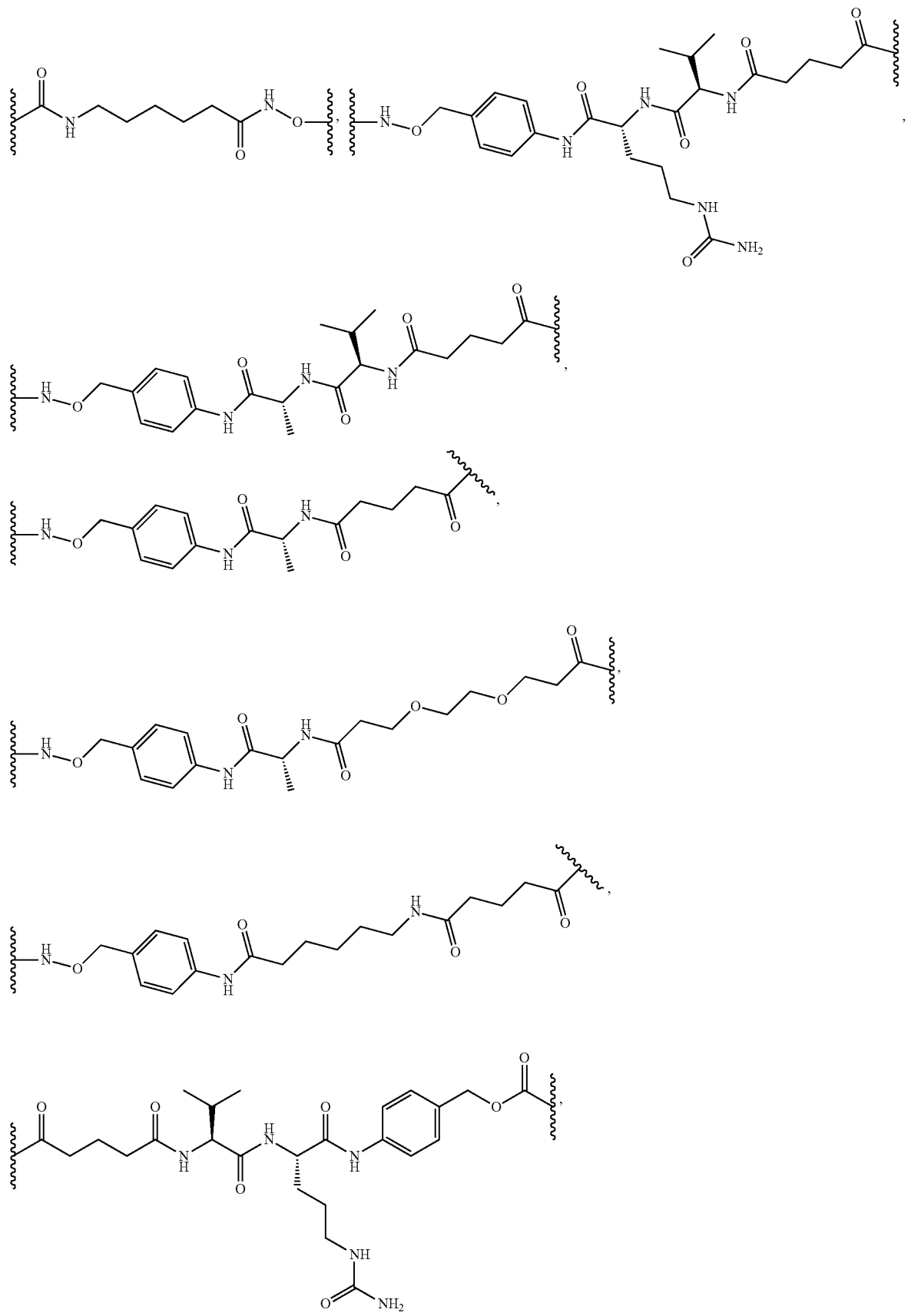

-continued
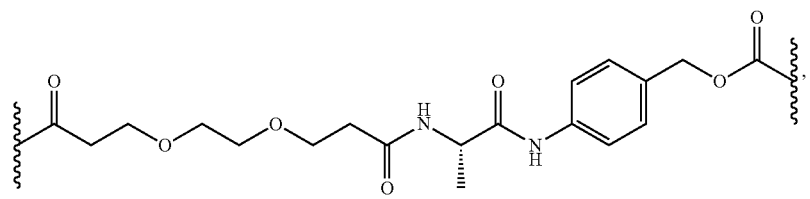
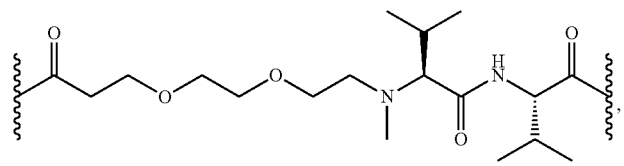
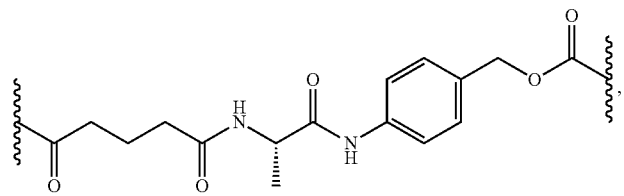
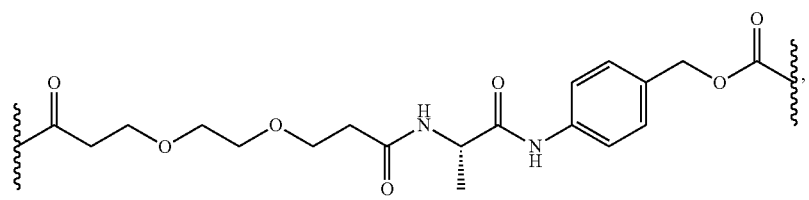
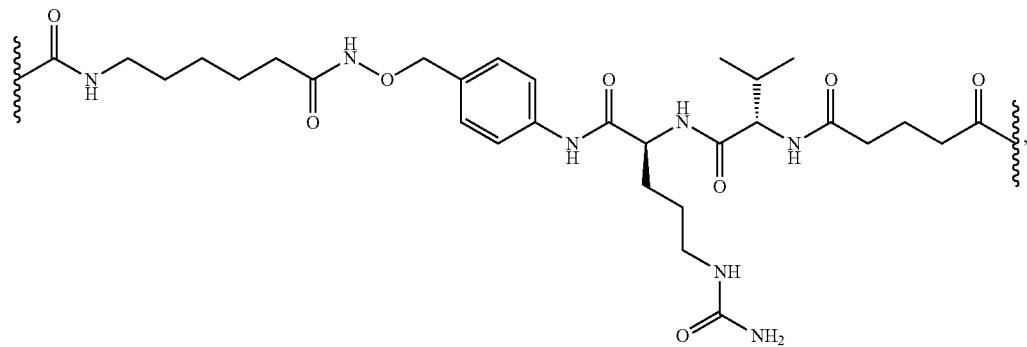
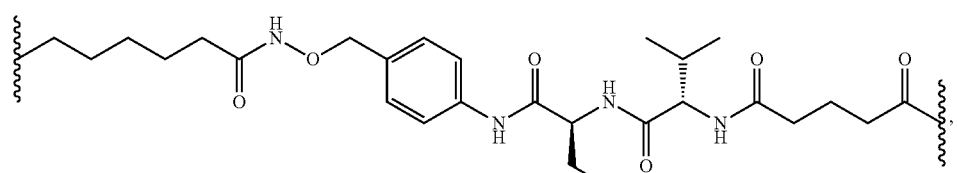
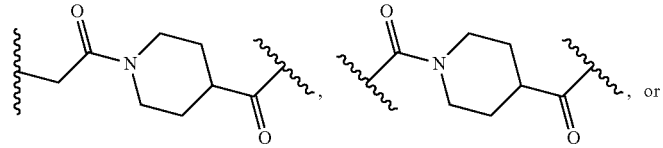

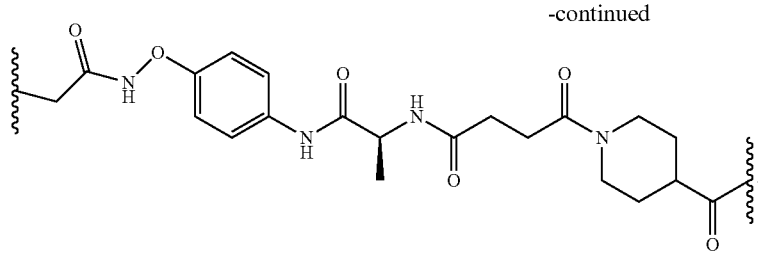

In some embodiments, the agent-conjugate having the structure of Formula I has the structure of:

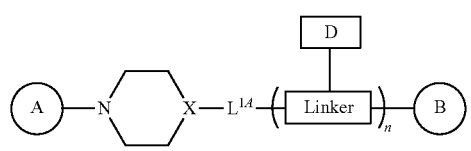

or a pharmaceutically acceptable salt thereof, wherein Linker comprises at least one component selected from the group consisting a peptide, an oligosaccharide, —(CH$_2$)—, O (oxygen), S (sulfur), —NH—, —(CH$_2$CH$_2$O)—, Val, Cit, PAB, Phe, Lys, D-Val, Leu, Lys, Gly, Ala, Asn, and the like.

In some embodiments, Linker may include —(CH$_2$)$_n$— where n is 1, 2, 3, 4, 5, 6, 7, 8, 9, or 10.

In some embodiments, Linker may include —(CH$_2$CH$_2$O)$_n$— where n is 1, 2, 3, 4, 5, 6, 7, 8, 9, or 10.

In some embodiments, Linker may include Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB, or the like.

In some embodiments, Linker may include any combination of peptide, oligosaccharide, —(CH$_2$)$_n$—, —(CH$_2$CH$_2$O)$_n$—, Val-Cit-PAB, Val-Ala-PAB, Val-Lys(Ac)-PAB, Phe-Lys-PAB, Phe-Lys(Ac)-PAB, Ala-PAB, PAB, D-Val-Leu-Lys, Gly-Gly-Arg, Ala-Ala-Asn-PAB, and the like.

Description of the Conjugation Methods

General Procedure A:

Some embodiments provide a method of chemical synthesis comprising: reacting an amine of formula I-A with a dialdehyde of formula I-B to provide the active agent-conjugate of formula (Iab).

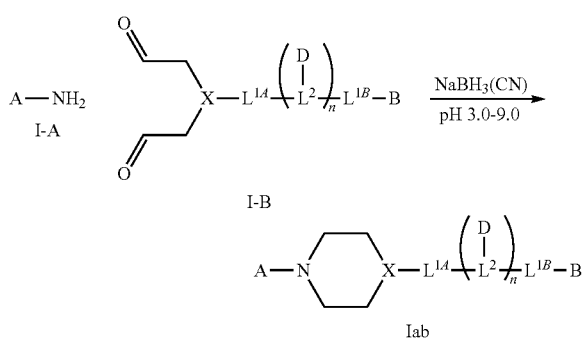

General Procedure B:

Some embodiments provide a method of chemical synthesis comprising: reacting an amine of formula II-A with a activated carboxylic component of formula II-B to provide the active agent-conjugate of formula (Ia").

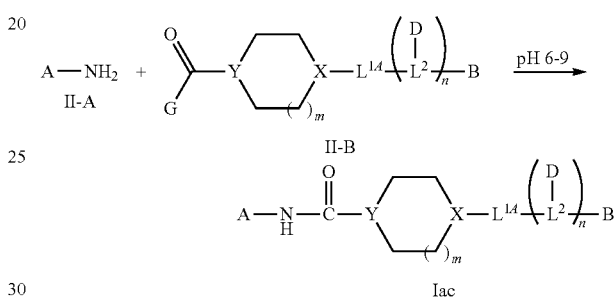

Selectively react with amino groups to form a six-membered ring, examples include but are not limited:

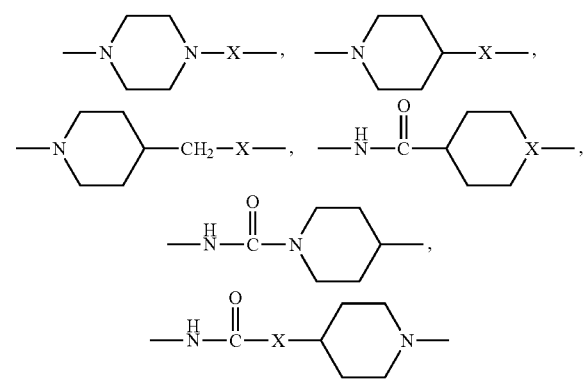

and the like.

In some embodiments, the agent-conjugates may include one or more components selected from the group consisting of an amino acid, an amino acid residue, an amino acid analog, and a modified amino acid.

As used herein, the term "targeting moiety" refers to a structure that binds or associates with a biological moiety or fragment thereof.

In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand.

In some embodiments, the targeting moiety may be an antibody fragment described in Janthur et al., "Drug Conjugates Such as Antibody Drug Conjugates (ADCs), Immunotoxins and Immunoliposomes Challenge Daily Clinical Practice," *Int. J. Mol. Sci.* 2012, 13, 16020-16045, the disclosure of which is incorporated herein by reference in its entirety. In some embodiments, the targeting moiety may be an antibody fragment described in Trail, Pa., "Antibody Drug Conjugates as Cancer Therapeutics," *Antibodies* 2013, 2, 113-129, the disclosure of which is incorporated herein by reference in its entirety.

In some embodiments, the targeting moiety may be HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544. In some embodiments, the targeting moiety may comprise, consist of, or consist essentially of the antibody portion of HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544.

In some embodiments, the targeting moiety may be Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of the antibody portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of Brentuximab, Inotuzumab, Gemtuzumab, Milatuzumab, Trastuzumab, Glembatumomab, Lorvotuzumab, or Labestuzumab.

As used herein, the term "peptide" refers to a structure including one or more components each individually selected from the group consisting of an amino acid, an amino acid residue, an amino acid analog, and a modified amino acid. The components are typically joined to each other through an amide bond.

As used herein, the term "amino acid" includes naturally occurring amino acids, a molecule having a nitrogen available for forming an amide bond and a carboxylic acid, a molecule of the general formula NH$_2$—CHR—COOH or the residue within a peptide bearing the parent amino acid, where "R" is one of a number of different side chains. "R" can be a substituent found in naturally occurring amino acids. "R" can also be a substituent referring to one that is not of the naturally occurring amino acids.

As used herein, the term "amino acid residue" refers to the portion of the amino acid which remains after losing a water molecule when it is joined to another amino acid.

As used herein, the term "amino acid analog" refers to a structural derivative of an amino acid parent compound that often differs from it by a single element.

As used herein, the term "modified amino acid" refers to an amino acid bearing an "R" substituent that does not correspond to one of the twenty genetically coded amino acids.

As used herein, the abbreviations for the genetically encoded L-enantiomeric amino acids are conventional and are as follows: The D-amino acids are designated by lower case, e.g. D-proline=p, etc.

TABLE 1

| Amino Acids | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Certain amino acid residues in the active agent-conjugate can be replaced with other amino acid residues without significantly deleteriously affecting, and in many cases even enhancing, the activity of the peptides. Thus, also contemplated by the preferred embodiments are altered or mutated forms of the active agent-conjugate wherein at least one defined amino acid residue in the structure is substituted with another amino acid residue or derivative and/or analog thereof. It will be recognized that in preferred embodiments, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into nonpolar and aromatic amino acids. The definitions of the various categories of amino acids are as follows:

The term "hydrophilic amino acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R).

The term "hydrophobic amino acid" refers to an amino acid exhibiting a hydrophobicity of greater than zero according to the normalized consensus hydrophobicity scale of Eisenberg, 1984, J. Mol. Biol. 179:1.25-142. Genetically encoded hydrophobic amino acids include Pro (P), Ile (I), Phe (F), Val (V), Leu (L), Trp (W), Met (M), Ala (A), Gly (G) and Tyr (Y).

The term "acidic amino acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

The term "basic amino acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

The term "polar amino acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

The term "nonpolar amino acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Leu (L), Val (V), Ile (I), Met (M), Gly (G) and Ala (A).

The term "aromatic amino acid" refers to a hydrophobic amino acid with a side chain having at least one aromatic or heteroaromatic ring. In some embodiments, the aromatic or heteroaromatic ring may contain one or more substituents such as —OH, —SH, —CN, —F, —Cl, —Br, —I, —NO$_2$, —NO, —NH$_2$, —NHR, NRR, —C(O)R, —C(O)OH, —C(O)OR, —C(O)NH$_2$, —C(O)NHR, —C(O)NRR and the like where each R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_5$-C$_{20}$) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

The term "aliphatic amino acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the preferred embodiments Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

While the above-defined categories have been exemplified in terms of the genetically encoded amino acids, the amino acid substitutions need not be, and in certain embodiments preferably are not, restricted to the genetically encoded amino acids. In some embodiments, the active agent-conjugate may contain genetically non-encoded amino acids. Thus, in addition to the naturally occurring genetically encoded amino acids, amino acid residues in the active agent-conjugate may be substituted with naturally occurring non-encoded amino acids and synthetic amino acids.

Certain commonly encountered amino acids which provide useful substitutions for the active agent-conjugates include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Ahx); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-phenylphenylalanine, 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH$_2$)); N-methyl valine (Me-Val); homocysteine (hCys), homophenylalanine (hPhe) and homoserine (hSer); hydroxyproline (Hyp), homoproline (hPro), N-methylated amino acids and peptoids (N-substituted glycines).

Other amino acid residues not specifically mentioned herein can be readily categorized based on their observed physical and chemical properties in light of the definitions provided herein.

The classifications of the genetically encoded and common non-encoded amino acids according to the categories defined above are summarized in Table 2, below. It is to be understood that Table 2 is for illustrative purposes only and does not purport to be an exhaustive list of amino acid residues and derivatives that can be used to substitute the active agent-conjugate described herein.

TABLE 2

CLASSIFICATIONS OF COMMONLY ENCOUNTERED AMINO ACIDS

| Classification | Genetically Encoded | Non-Genetically Encoded |
|---|---|---|
| Hydrophobic | | |
| Aromatic | F, Y, W | Phg, Nal, Thi, Tic, Phe (4-Cl), Phe (2-F), Phe (3-F), Phe (4-F), hPhe |
| Nonpolar | L, V, I, M, G, A, P | t-BuA, t-BuG, MeIle, Nle, MeVal, Cha, McGly, Aib |
| Aliphatic | A, V, L, I | b-Ala, Dpr, Aib, Ahx, MeGly, t-BuA, t-BuG, MeIle, Cha, Nle, MeVal |
| Hydrophilic | | |
| Acidic | D, E | |
| Basic | H, K, R | Dpr, Orn, hArg, Phe(p-$NH_2$), Dbu, Dab |
| Polar | C, Q, N, S. T | Cit, AcLys, MSO, bAla, hSer |
| Helix-Breaking | P, G | D-Pro and other D-amino acids (in L-peptides) |

Other amino acid residues not specifically mentioned herein can be readily categorized based on their observed physical and chemical properties in light of the definitions provided herein.

While in most instances, the amino acids of the active agent-conjugate will be substituted with L-enantiomeric amino acids, the substitutions are not limited to L-enantiomeric amino acids. In some embodiments, the peptides may advantageously be composed of at least one D-enantiomeric amino acid. Peptides containing such D-amino acids are thought to be more stable to degradation in the oral cavity, gut or serum than are peptides composed exclusively of L-amino acids.

In some embodiments, the compositions and method provided herein can provide an increased selectivity in targeting lysine side chain amino groups. In some embodiments >80% of a composition comprising an active agent-conjugate as disclosed and described herein consists of no more than two active components. In some embodiments >70% of a composition comprising an active agent-conjugate as disclosed and described herein consists of no more than two active components. In some embodiments >60% of a composition comprising an active agent-conjugate as disclosed and described herein consists of no more than two active components. In some embodiments >50% of a composition comprising an active agent-conjugate as disclosed and described herein consists of no more than two active components. In some embodiments >40% of a composition comprising an active agent-conjugate as disclosed and described herein consists of no more than two active components. In some embodiments >30% of a composition comprising an active agent-conjugate as disclosed and described herein consists of no more than two active components. In some embodiments >80% of a composition comprising an active agent-conjugate as disclosed and described herein consists of only two active components. In some embodiments >70% of a composition comprising an active agent-conjugate as disclosed and described herein consists of only two active components. In some embodiments >60% of a composition comprising an active agent-conjugate as disclosed and described herein consists of only two active components. In some embodiments >50% of a composition comprising an active agent-conjugate as disclosed and described herein consists of only two active components. In some embodiments >40% of a composition comprising an active agent-conjugate as disclosed and described herein consists of only two active components. In some embodiments >30% of a composition comprising an active agent-conjugate as disclosed and described herein consists of only two active components.

Single-Step Conjugation—Dialdehyde Reductive Amination

General Conjugation Procedure I:

To a solution of 0.5-50 mgs/mL of targeting molecule A in buffet at pH 3.0-8.0, was added 2-6 eq of dialdehyde component and 2-50 eq of NaBCNH3. The reaction was performed at 0-40° C. for 0.5-50 hours with gentle stirring or shaking, monitored by HIC-HPLC. The resultant crude ADC product underwent necessary down-stream steps of desalt, buffet changes/formulation, and optionally, purification, using the state-of-art procedures. The final ADC product was characterized by HIC-HPLC, SEC, RP-HPLC, and optionally LC-MS. The average DAR was calculated by UV absorption and/or MS spectroscopy.

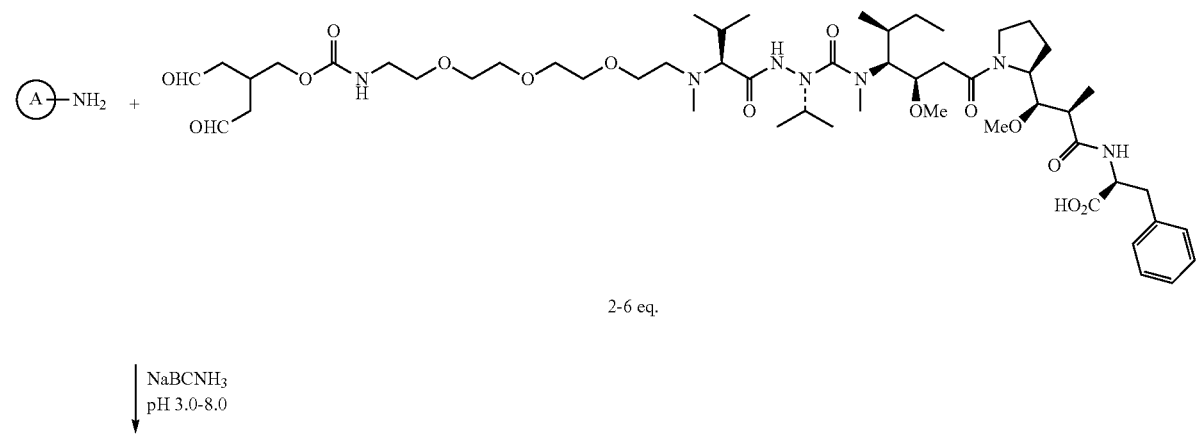

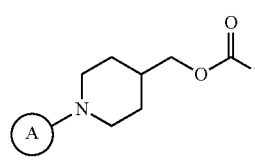
-continued
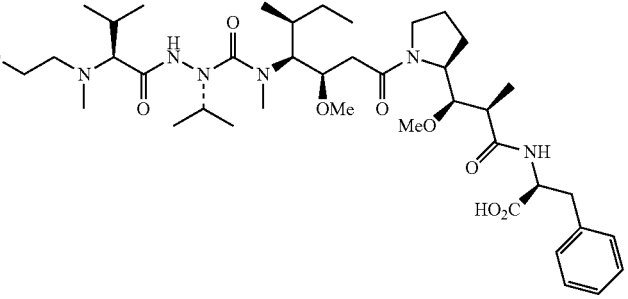
Examples that may be prepared by General Scheme I include, but are not limited, the following general compounds:
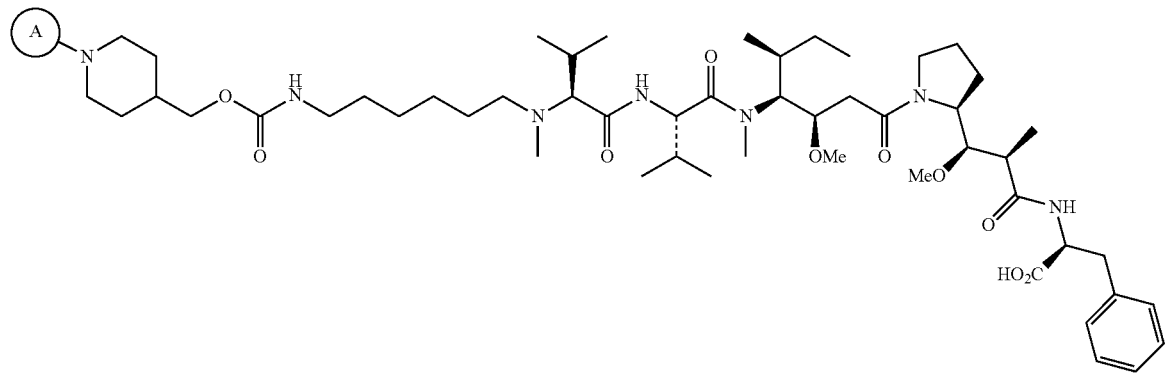
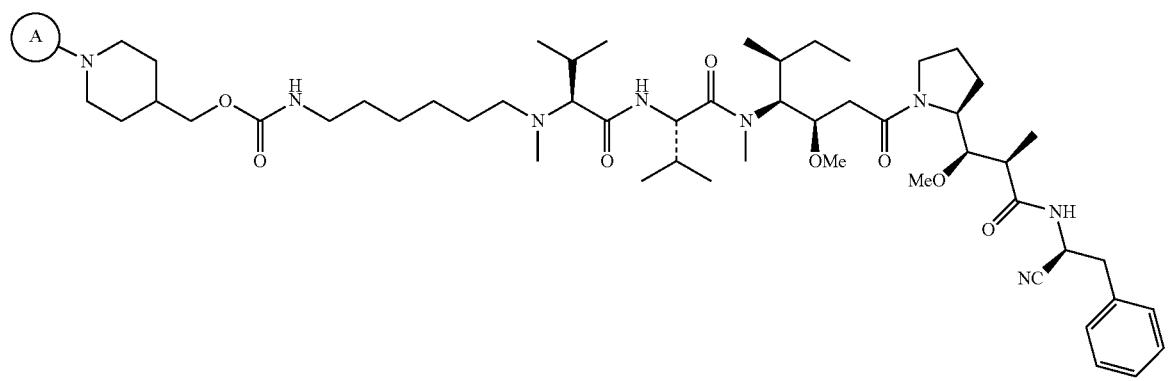
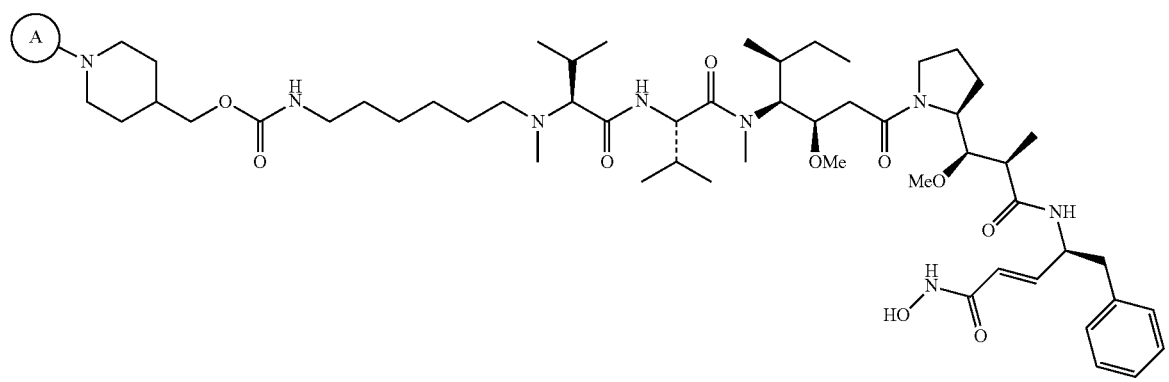

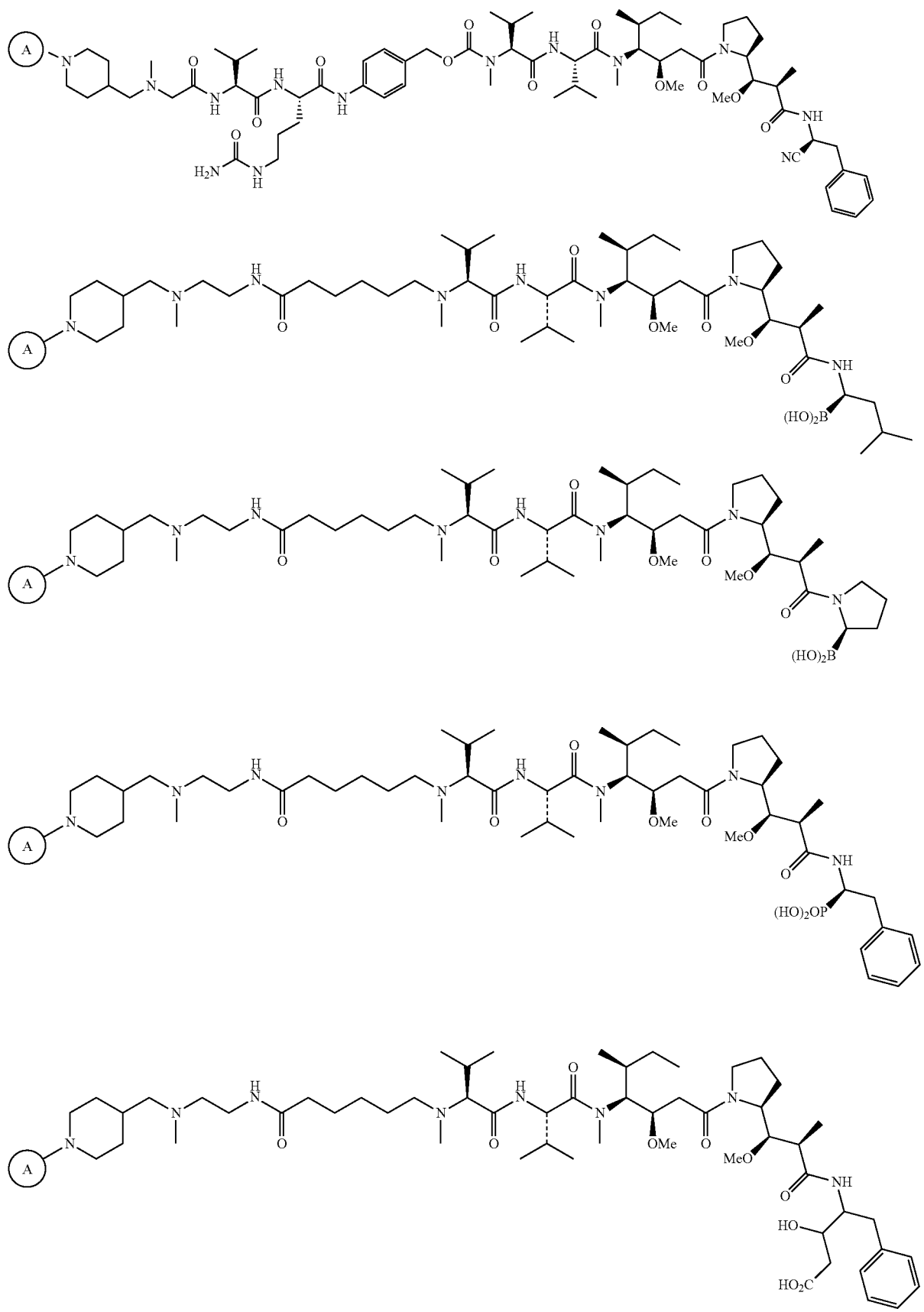

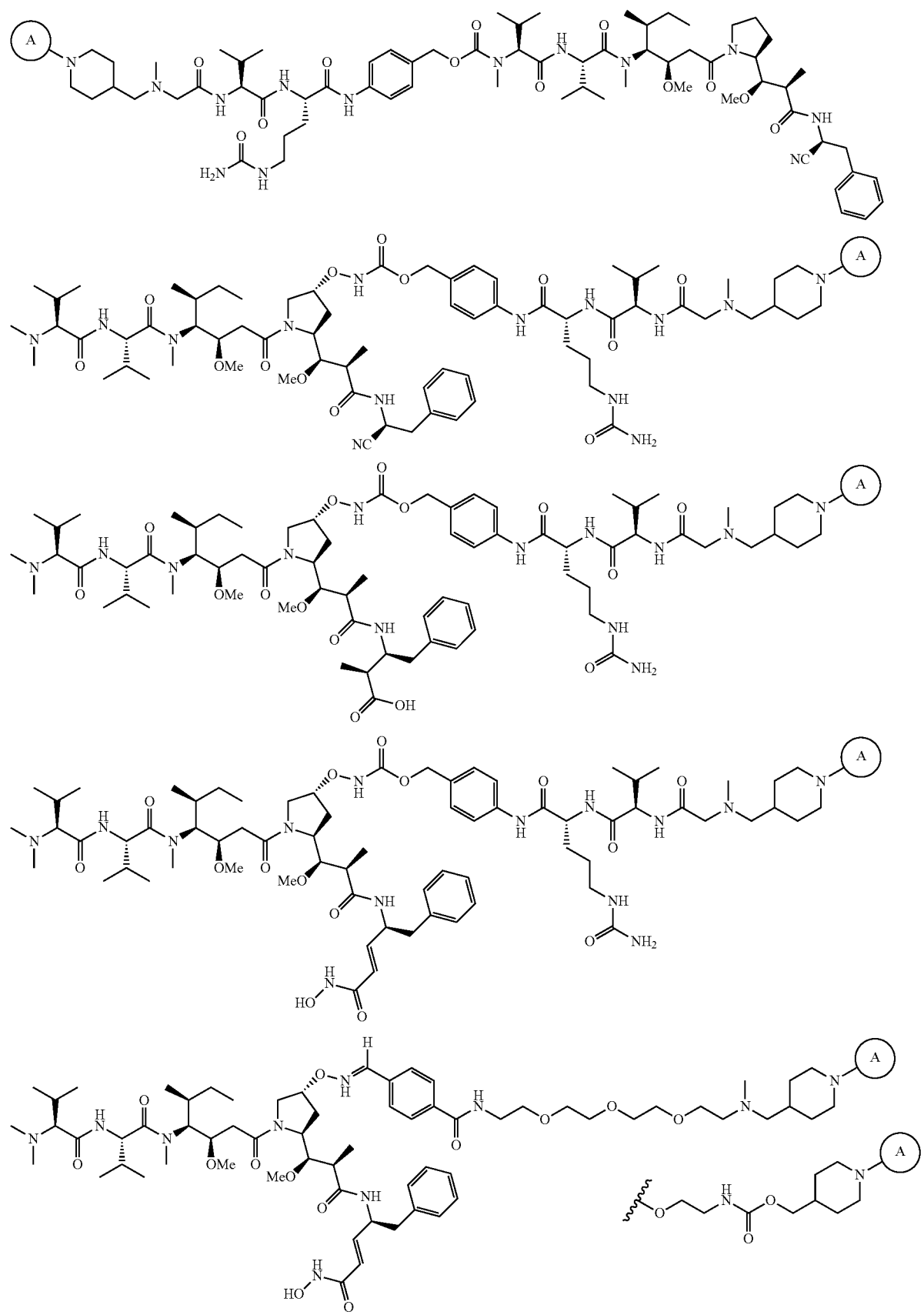

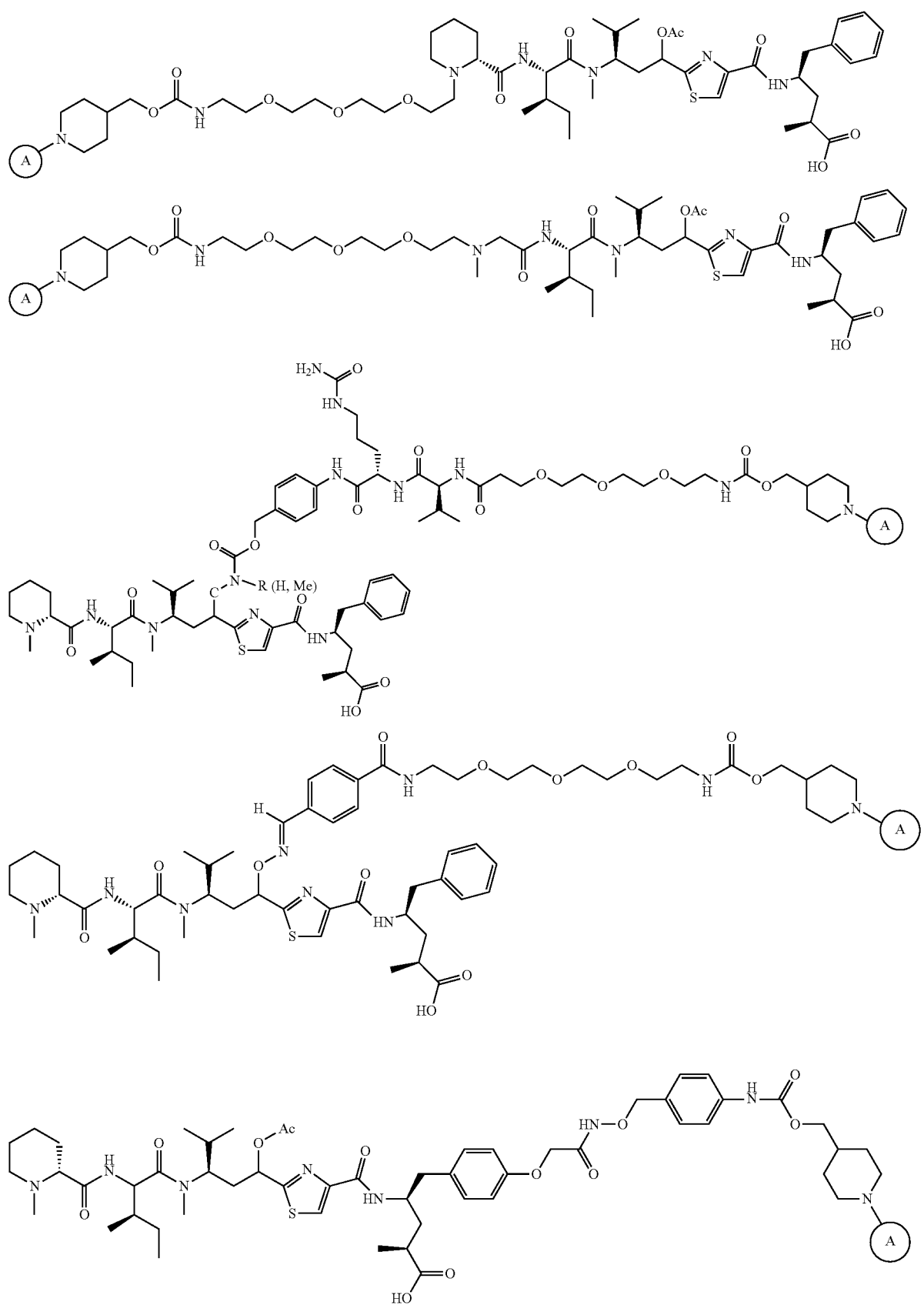

-continued

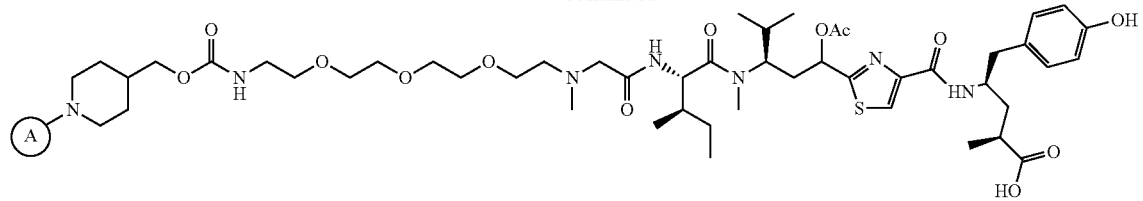

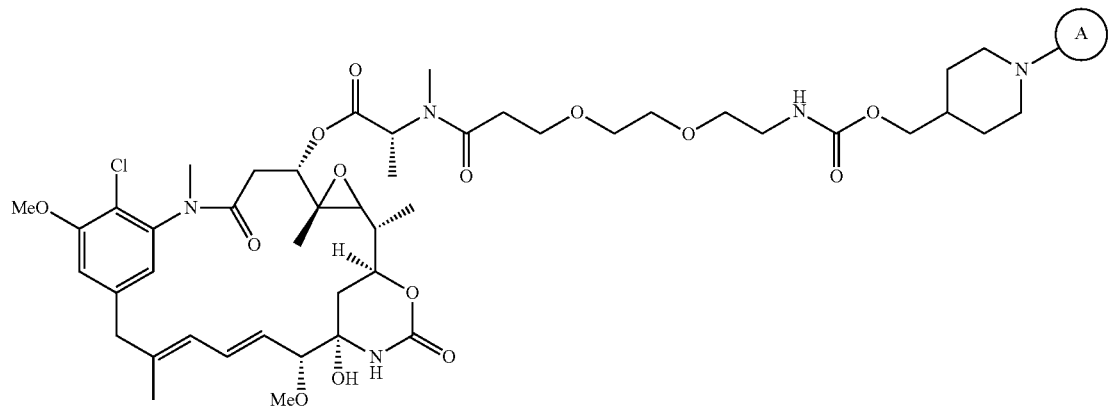

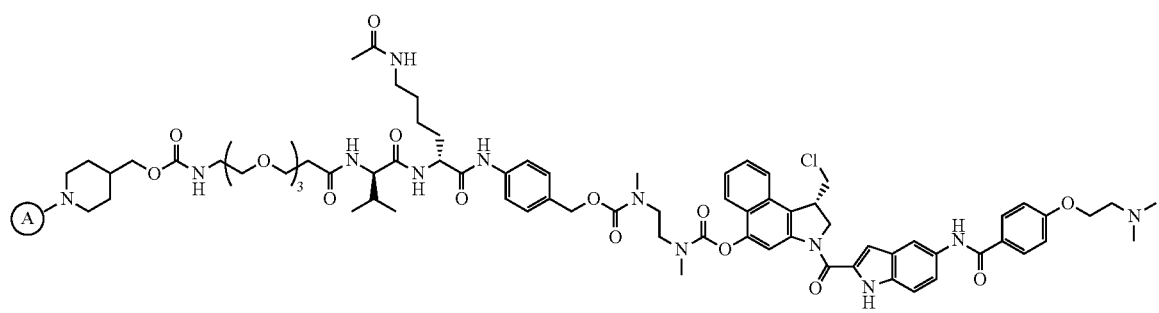

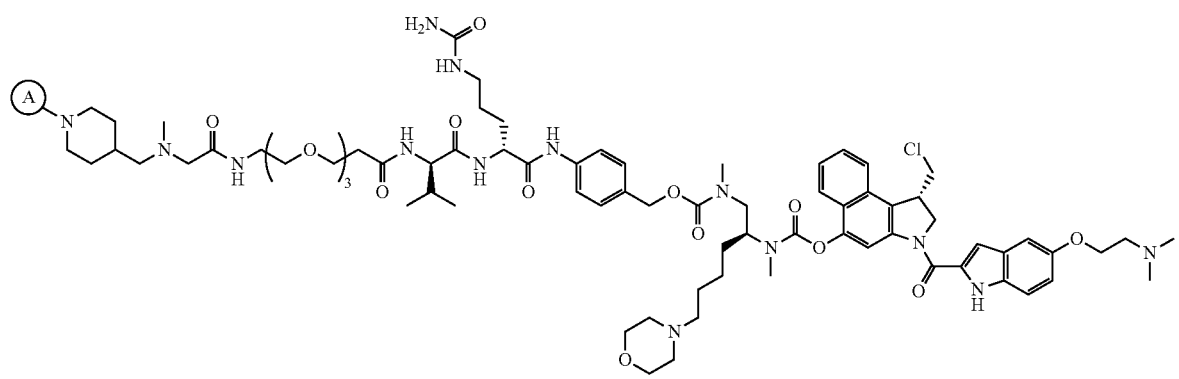

General Conjugation Procedure II:

To a solution of 0.5-50 mgs/mL of targeting molecule A in buffer at pH 6.0-9.0 with 0-30% organic solvent, was added 0.1-10 eq of activated carboxylic component in a manner of portion wise or continuous flow. The reaction was performed at 0-40° C. for 0.5-50 hours with gentle stirring or shaking, monitored by HIC-HPLC. The resultant crude ADC product underwent necessary down-stream steps of desalt, buffet changes/formulation, and optionally, purification, using the state-of-art procedures. The final ADC product was characterized by HIC-HPLC, SEC, RP-HPLC, and optionally LC-MS. The average DAR was calculated by UV absorption and/or MS spectroscopy.

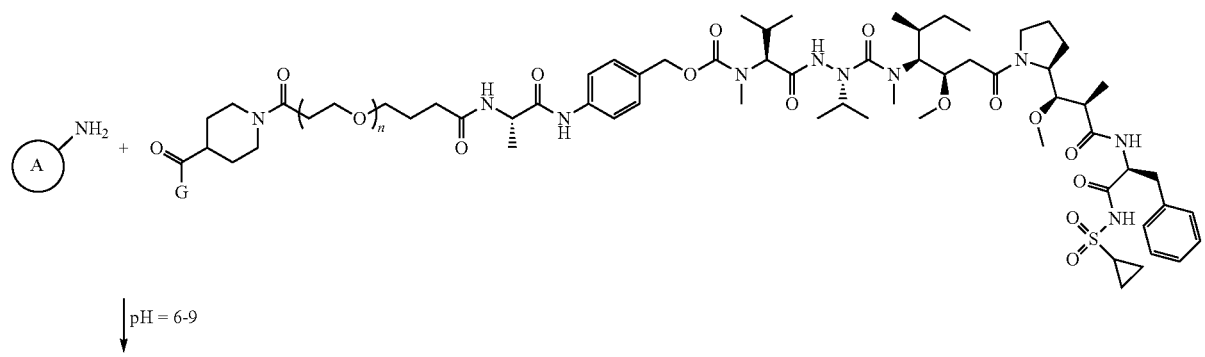

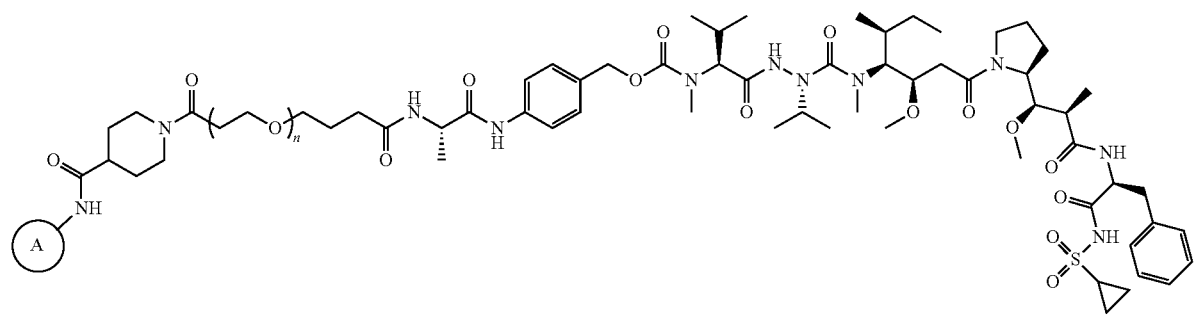

Some activated carboxylic components in General Conjugation Procedure II [0160] bear a leaving group G selected from —F, —Cl, —Br, —I, —N₃, —OR (R=substituted alkyl, substituted aryl, heterocycle, substituted heterocycle), SR (R=alkyl, aryl, substituted aryl), —ON(R¹)R², RC(=O)O—, and RSO₂—O—.

Some activated carboxylic components were selected, not limited from the following group to provide active agent-conjugates of Formula I according to General Conjugation Procedure II:

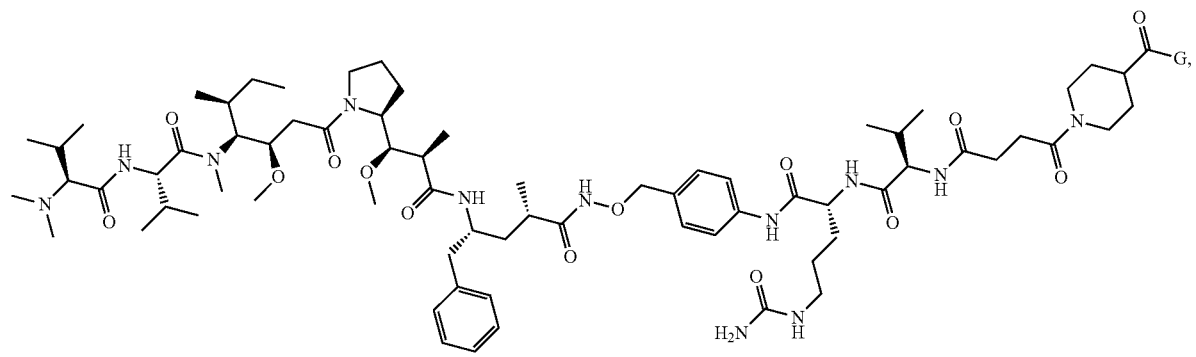

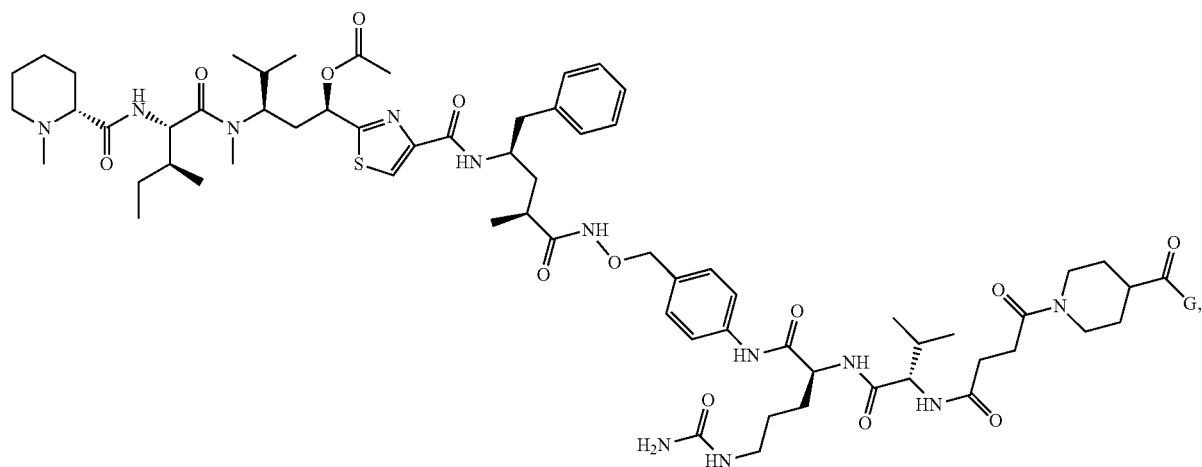
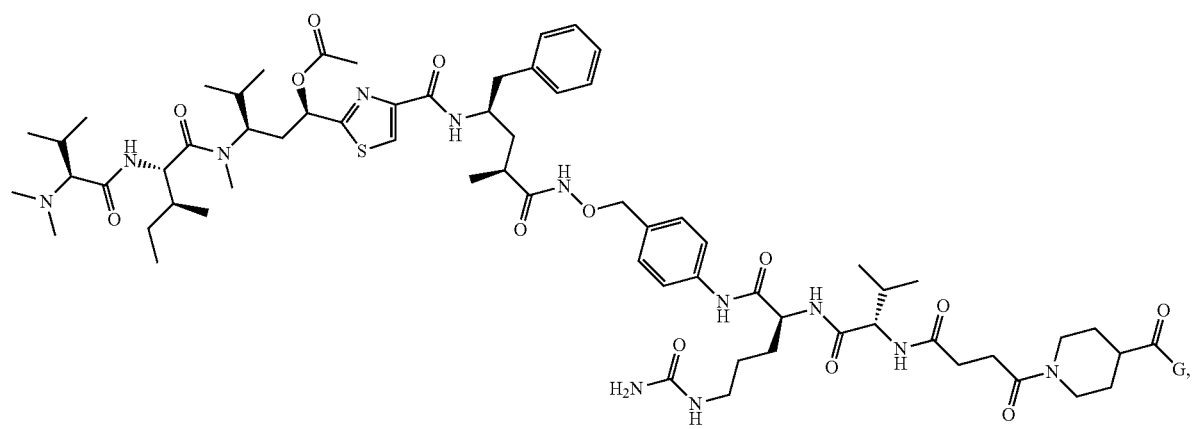
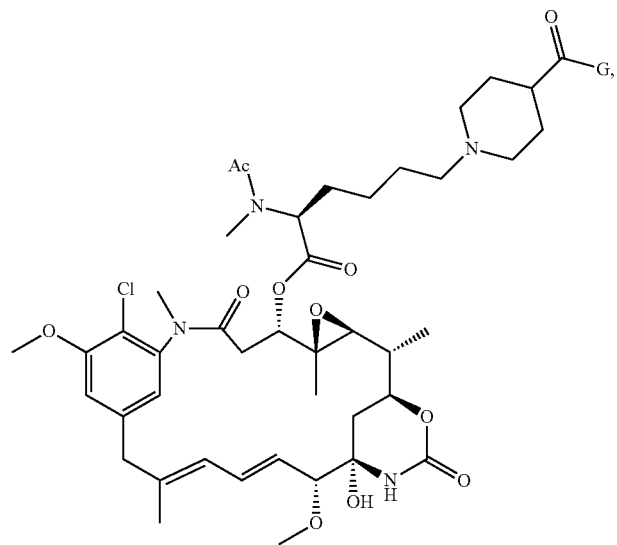

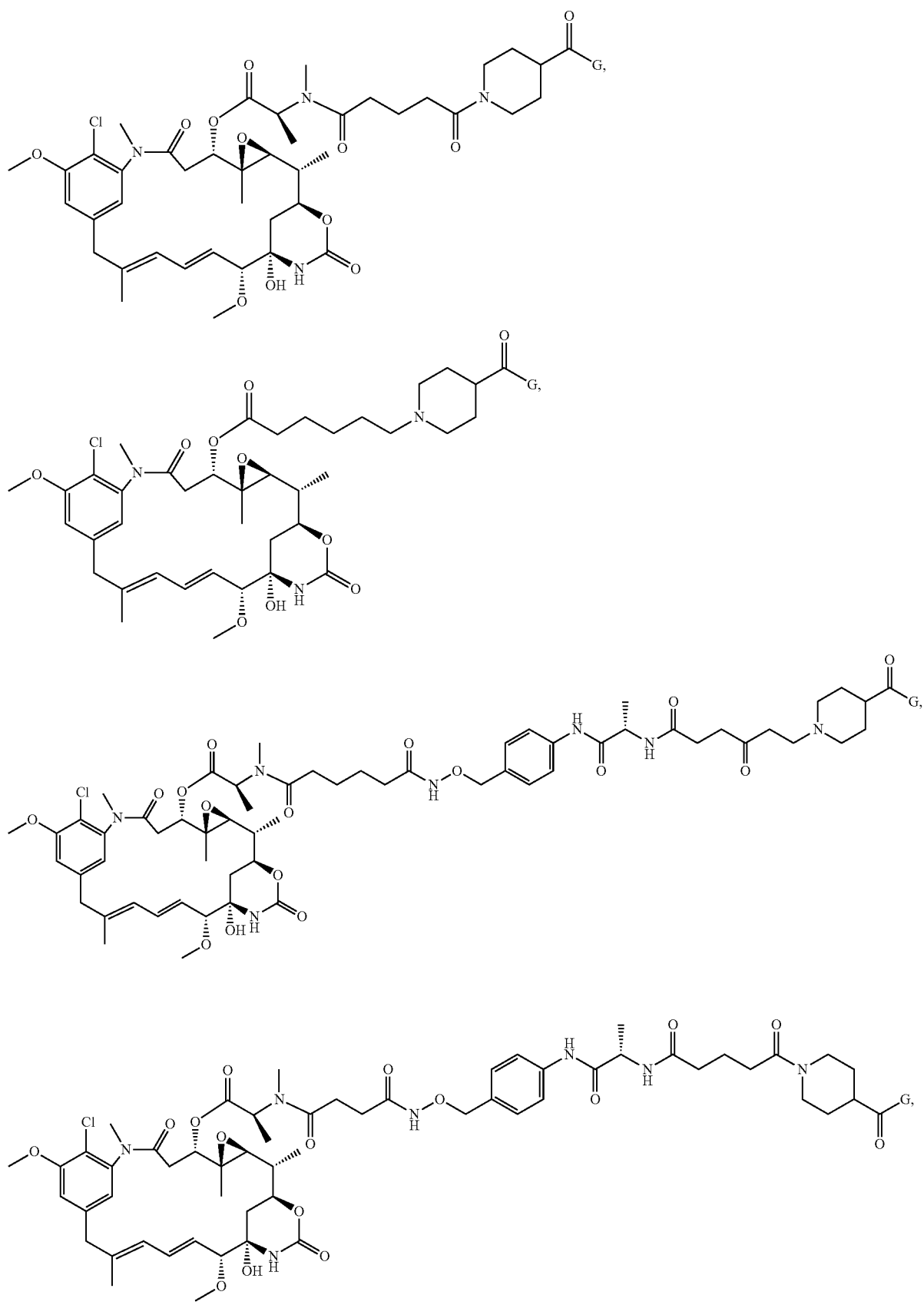

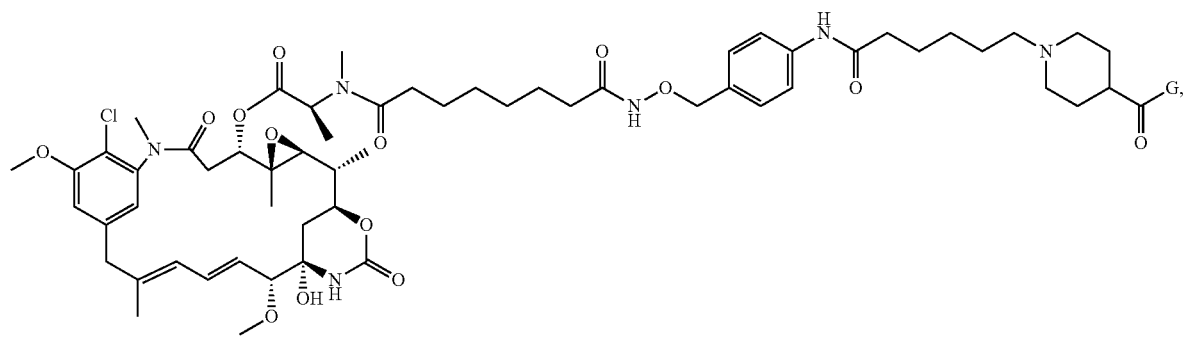
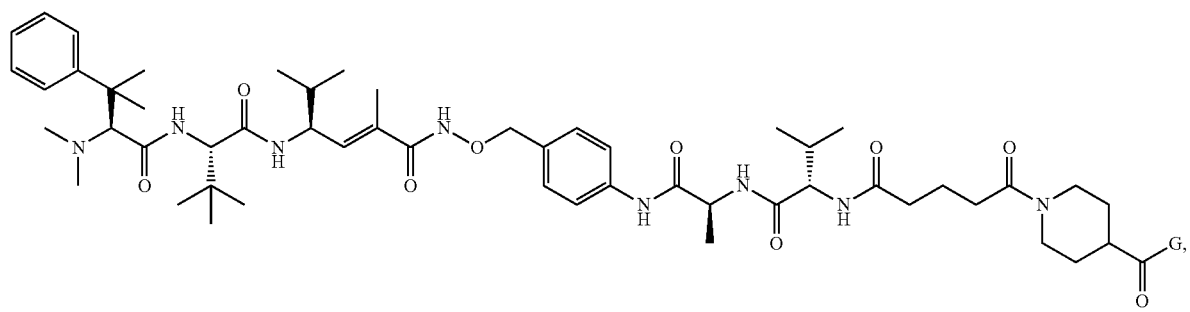
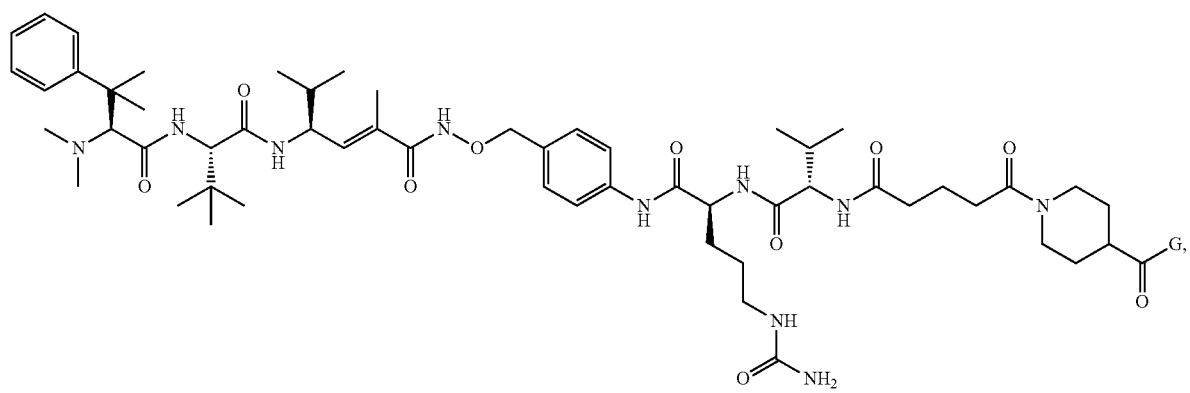
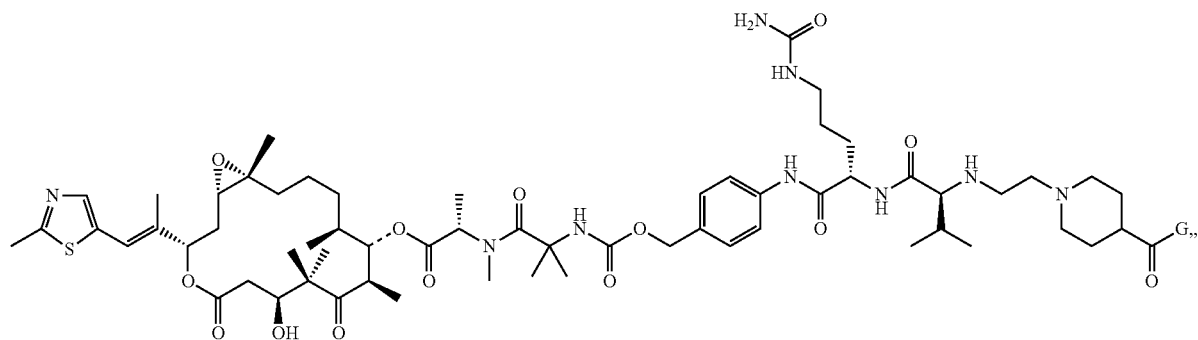

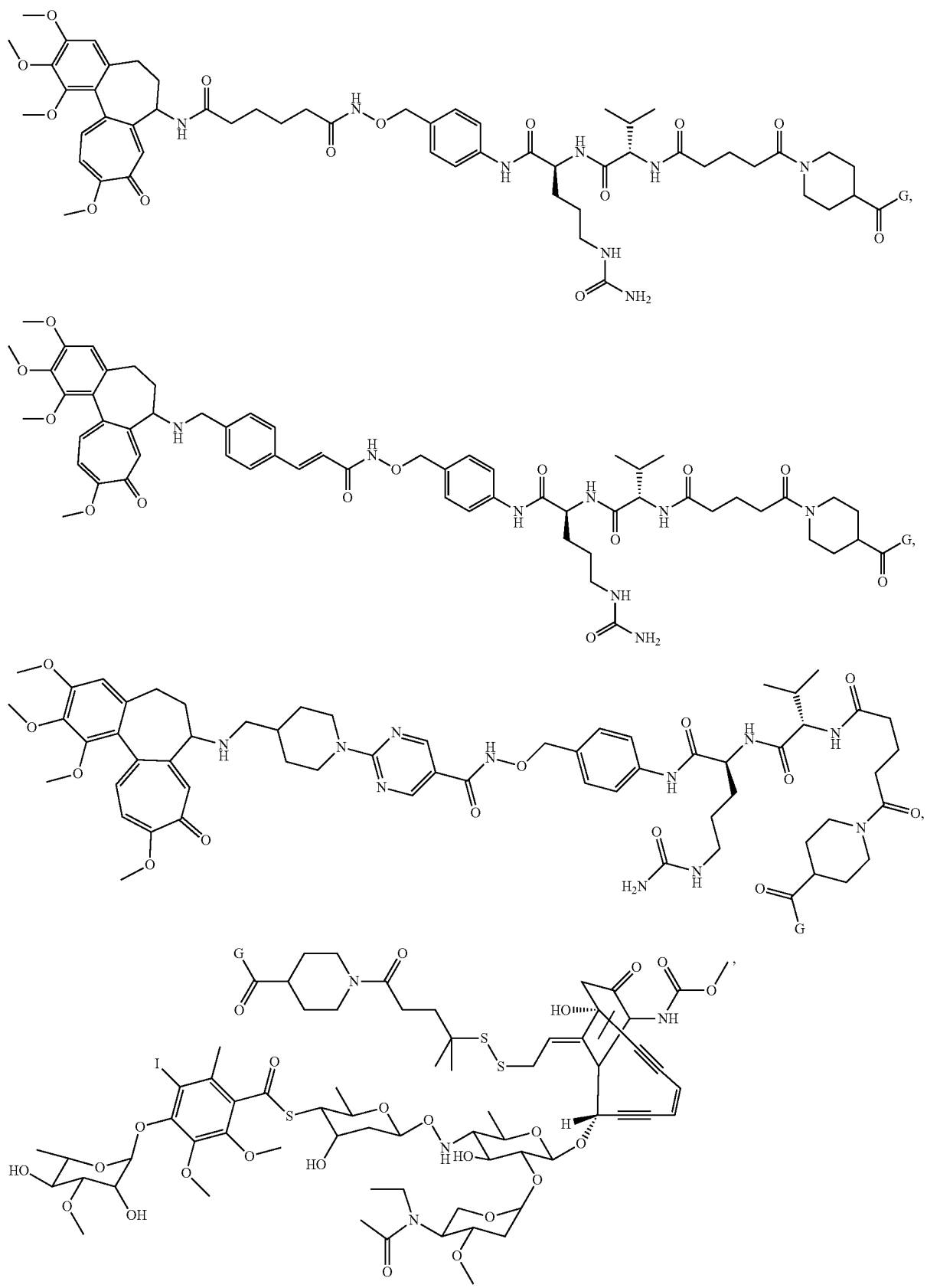

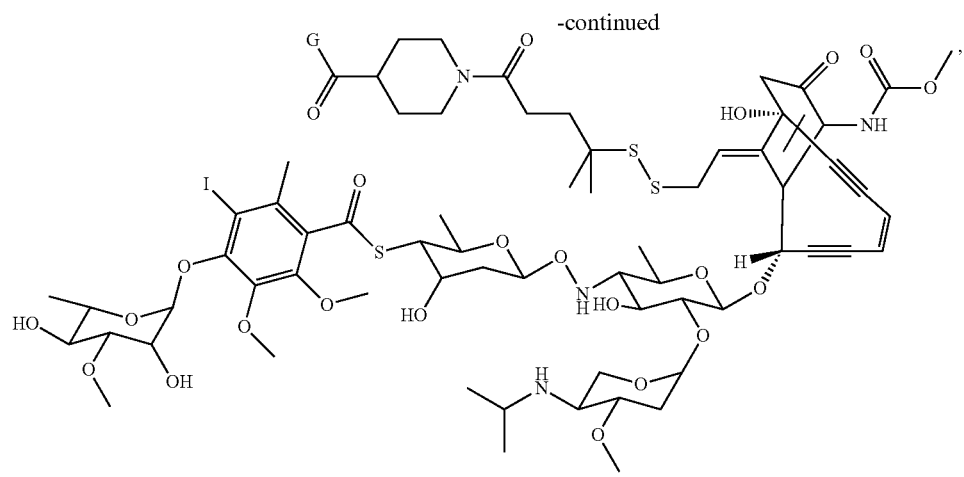
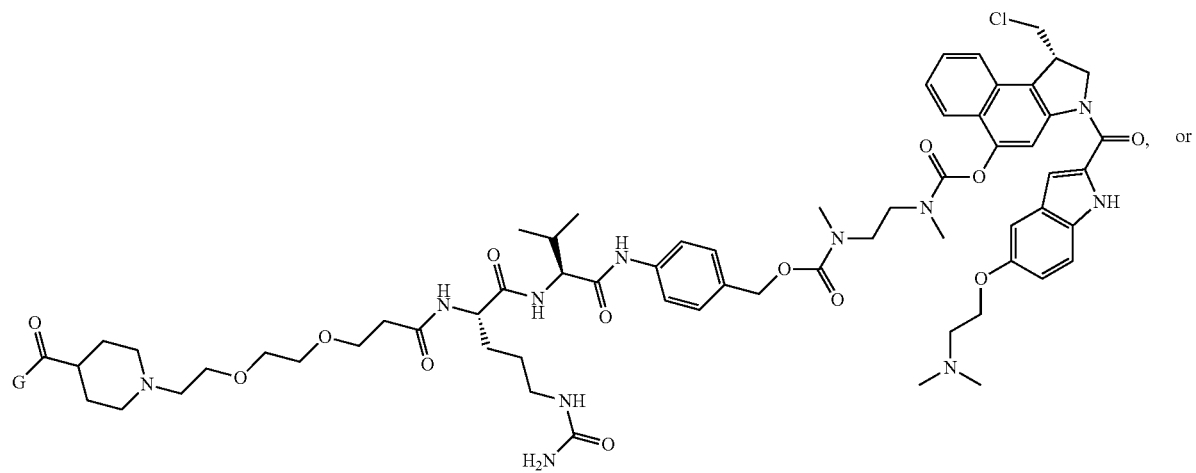
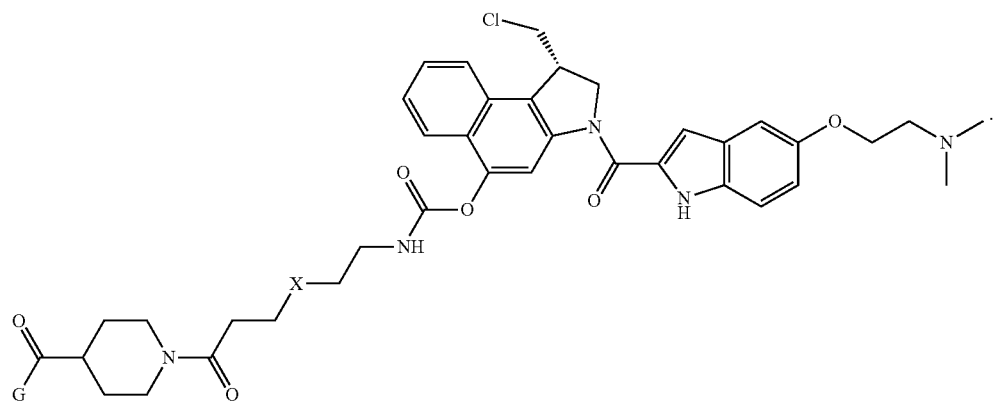
X = O, or CH₂
In some embodiments, active agent-conjugates of Formula I made according to General Conjugation Procedure II have, but are not limited to, the following structures:

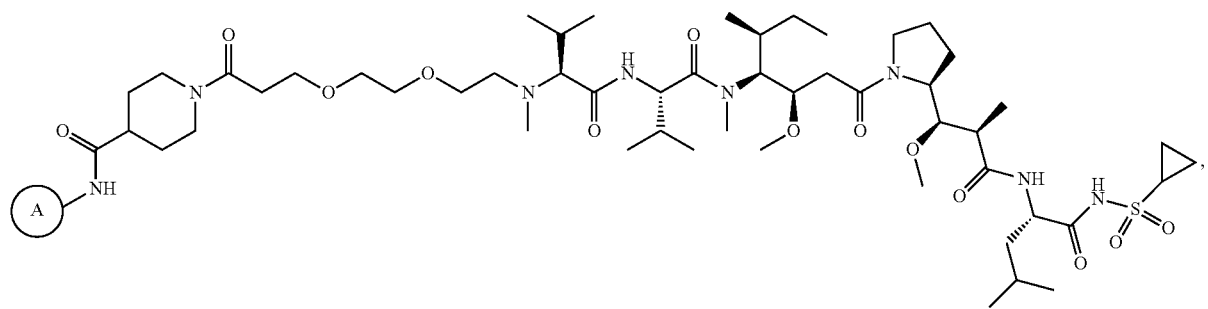
and like.
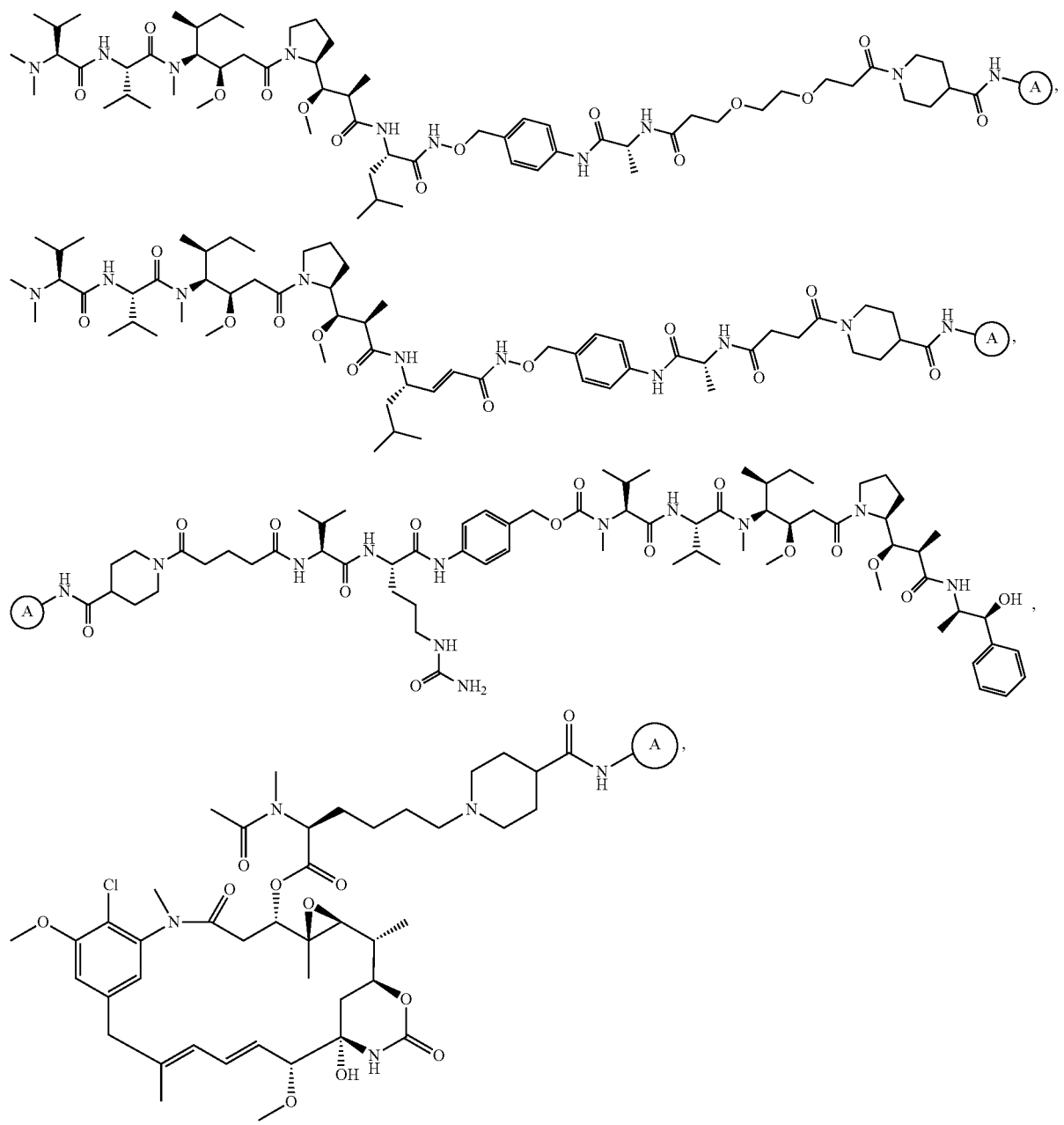

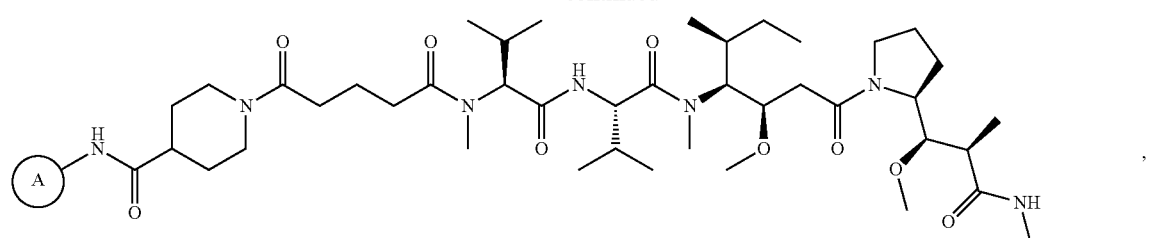
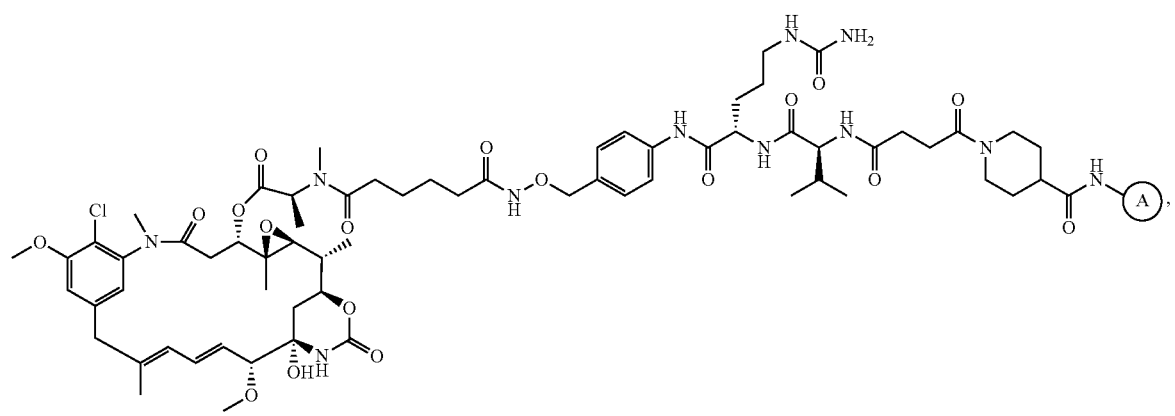
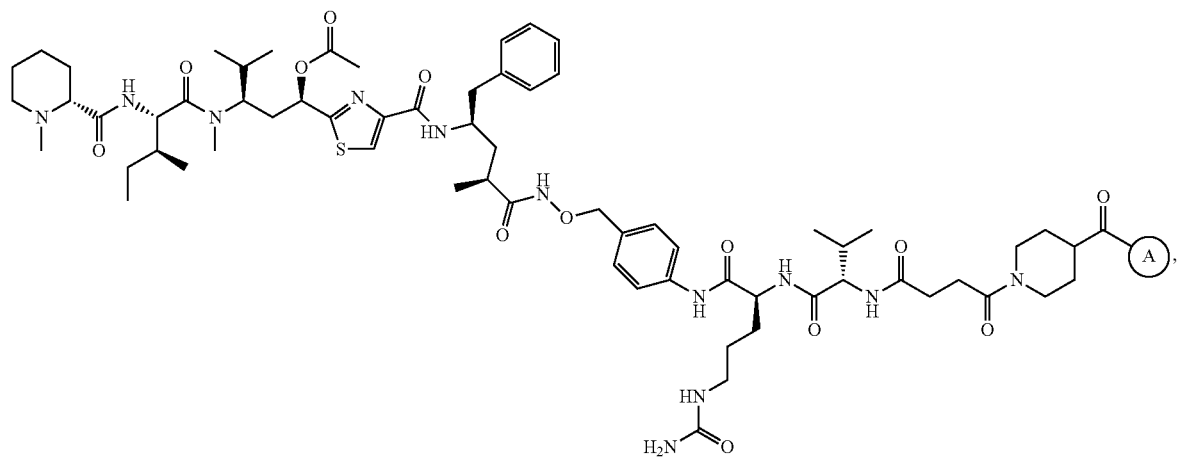
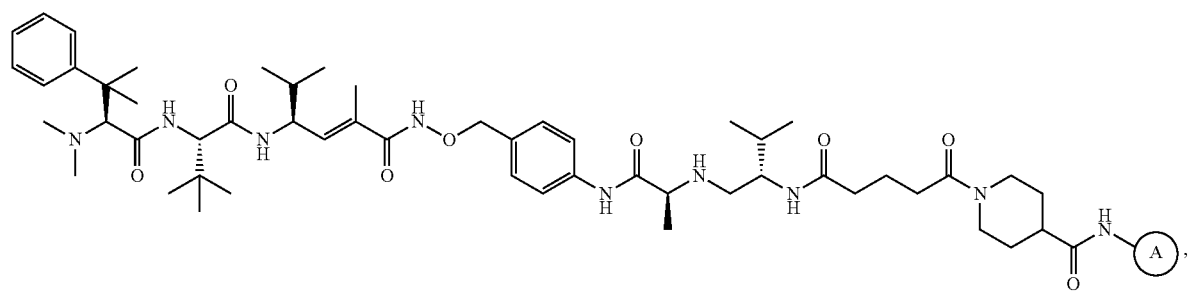

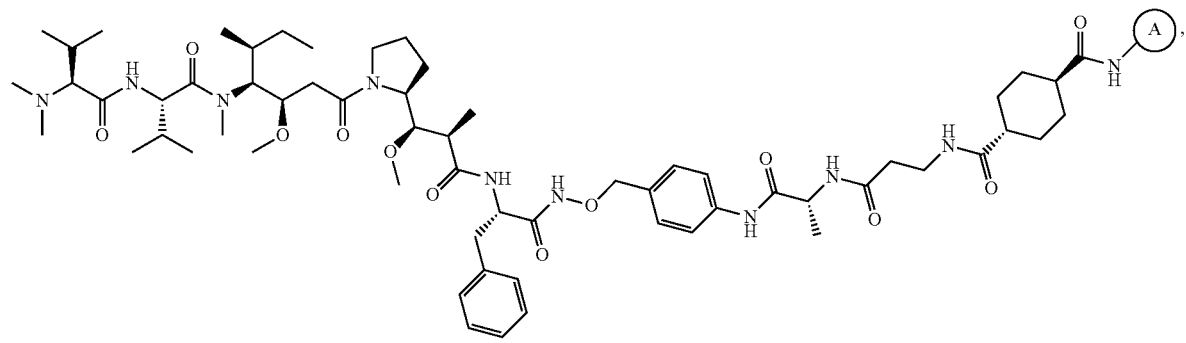
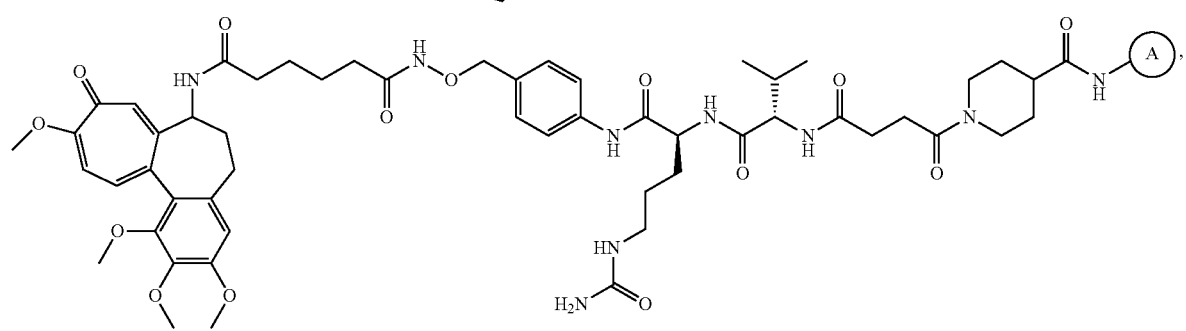
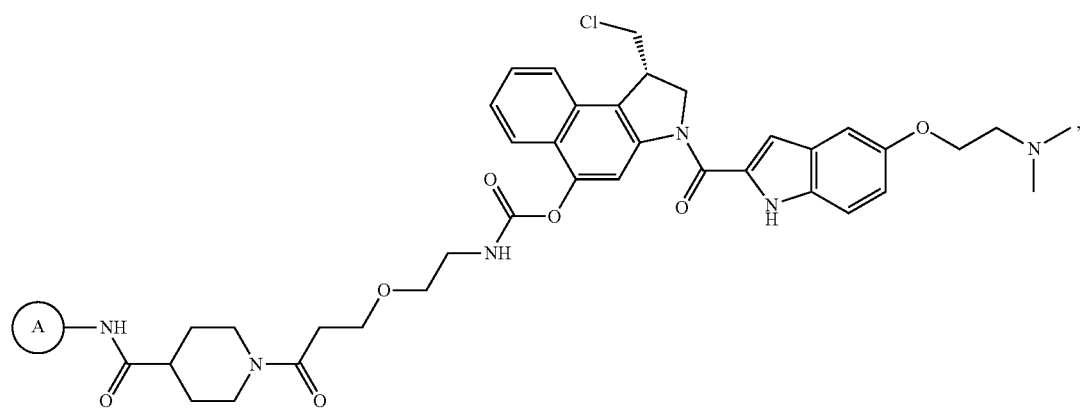
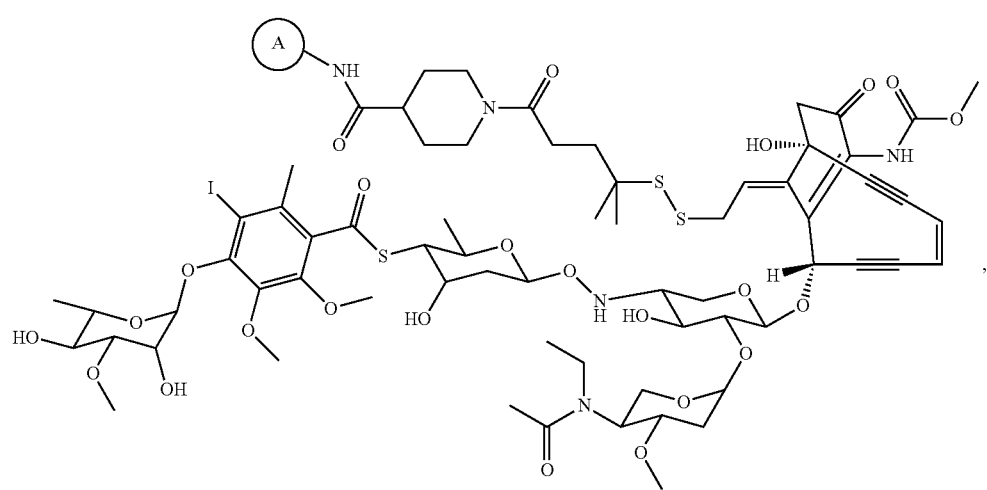

-continued

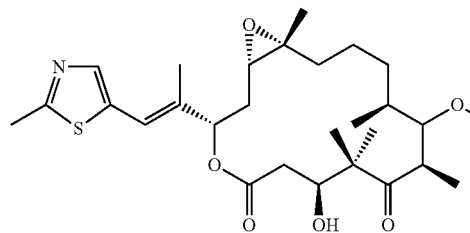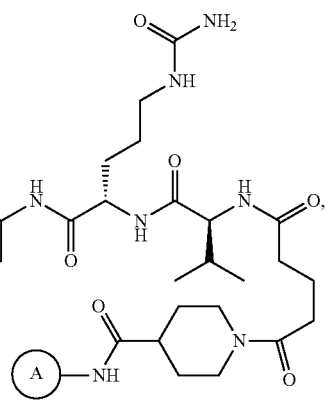

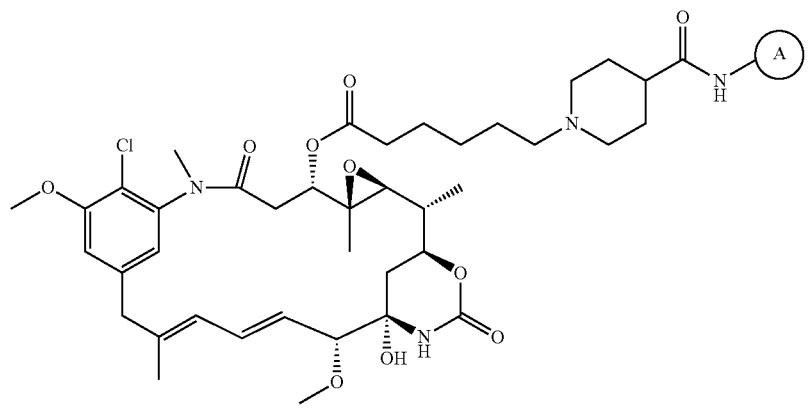

or the like.

EXPERIMENTALS

General Synthetic Procedures
General Procedure A—HATU Mediated Amide Bond Formation To an acid (1.1 eq with respect to amine) in anhydrous DMF was added HATU (1 eq with respect to acid) and DIEA (2 eq with respect to acid) and the mixture was stirred at room temperature for 1 minute. The mixture was then added to a solution of amine in DMF and the reaction mixture was stirred at room temperature till the completion of the reaction (monitored by LC/MS). The solvent was removed under reduced pressure and the residue was optionally purified by reverse phase HPLC to give final pure product.

General Procedure B—DIC/HOAt Mediated Amide Bond Formation

To a stirred solution of carboxylic acid (1.1 eq), amine and HOAt (1.1 eq) in anhydrous DMF was added DIC (1.1 eq) and the reaction mixture was stirred at room temperature. Upon completion (monitored by LC/MS), the solvent was removed under reduced pressure and the residue was optionally purified by reverse phase HPLC to give final pure product.

General Procedure C—Removal of Acid Sensitive Protecting Groups (Boc, THP, t-Bu) Using HCl/Dioxane The acid sensitive protecting groups containing compound was dissolved in 4N HCl/dioxane and the mixture was stirred at room temperature for 2 h. The solution was then concentrated under reduced pressure and the residue was washed twice with cold ether. Purification was carried out on reverse phase HPLC if necessary.

General Procedure D—Removal of Fmoc Group

The Fmoc containing compound was dissolved in 2-5% piperidine in DMF. The mixture was stirred at room temperature for 1 h. The solvents were removed under reduced pressure. Purification was carried out on reverse phase HPLC if necessary.

General Procedure E—Reductive Alkylation

An amine was dissolved in DMF and aldehyde (5 eq) was added, followed by addition of sodium cyanoborohydride (5 eq). HOAc was added to adjust the pH of the reaction mixture to 4-5. The mixture was stirred at room temperature till completion (1-4 h, monitored by HPLC). Purification was carried out on reverse phase HPLC if necessary.

General Procedure F—Saponification—Removal of Me/Et from Esters

To a stirred solution of an ester in MeOH was added 1M aq. solution of LiOH till pH of the mixture was about 13-14 and the reaction mixture was stirred at room temperature till completion (~16 h, monitored by HPLC). Citric acid (~10% aq.) was added to neutralize the reaction and the solvents were removed under reduced pressure. The crude product was optionally purified by RP-HPLC or used directly in the next step.

General Procedure G—Activation of a Hydroxyl/Phenol Group with Bis(p-Nitrophenyl)Carbonate To a stirred solution of an alcohol/phenol in THF/DMF (2/1) was added bis(p-nitrophenyl) carbonate (3-5 eq), followed by DIEA (2-4 eq) and the reaction mixture was stirred at room temperature until most of the starting material was consumed. The progress of the reaction was monitored by LC/MS. The crude product was optionally purified by flash column chromatography or by precipitation and washing.

General Procedure H—Reaction of an Amine with a Cyclic Anhydride (Glutaric Anhydride or Succinic Anhydride)

An amine containing compound was dissolved in DMF. Glutaric anhydride (3 eq) was added, followed by addition of DIEA (4 eq). The reaction mixture was stirred at room temperature until most of the starting material was consumed. The progress of the reaction was monitored by LC/MS. The crude product was purified by RP-HPLC to yield the pure carboxylic acid.

General Procedure I—Formation of Carbamate with p-Nitrophenyl Carbonate (e.g. FmocVC-PAB-PNP)

An amine containing compound was dissolved in DMF and alkyl/aryl p-nitrophenyl carbonate (1.5 eq) was added, followed by addition of DIEA (2 eq) and HOBt (cat., 5%). The reaction mixture was stirred at room temperature until most of the amine was consumed. The progress of the reaction was monitored by LC/MS. The crude product was optionally purified by RP-HPLC to yield the pure carbamate.

General Procedure J—Formation of an Activated Ester (e.g. NHS) from an Acid

An acid was dissolved in DCM and DMF was added to aid dissolution if necessary. N-hydroxysuccinimide (1.5 eq) was added, followed by EDC.HCl (1.5 eq). The reaction mixture was stirred at room temperature for 1 h until most of the acid was consumed. The progress of the reaction was monitored by RP-HPLC. The mixture was then diluted with DCM and washed successively with citric acid (aq. 10%) and brine. The organic Lyser was dried and concentrated to dryness. The crude product was optionally purified by RP-HPLC or silica gel column chromatography.

General Scheme for Active Agent Conjugates Formation
Conjugation Method A. Conjugation on Lys Residues Via an Activated Cyclic Carboxylic Acid A cyclic carboxylic acid moiety can also be easily obtained from the linear carboxylic acid derivative if the cyclic acid is not directly installed.

For example:

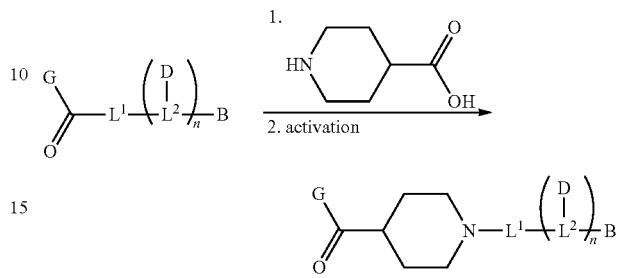

Conjugation Method B. Conjugation on Lys Residues Via an Activated Colic Carboxylic Acid

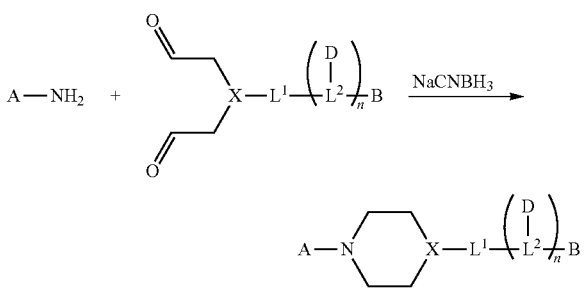

Experimental Description

Step 1. Drug-Linker Construct Synthesis (-L2-D)

Methods of Drug-Linker Construct Synthesis, but No Limited to:

Method 1-1: Linker and Drug Connected Via a Carbamate Bond. The Following General Procedures were Employed:

General Procedure G and I for Activation and Carbamate Formation

General Procedure C, D, and F for Removal of Protective Groups for Further Derivatization.

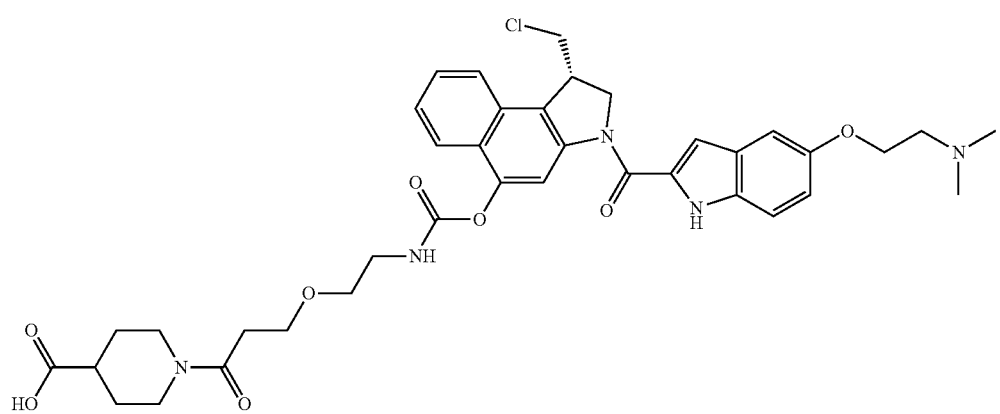 [SMILES: CN(C)CCOc1ccc2[nH]c(C(=O)N3C[C@@H](CCl)c4c3cc(OC(=O)NCCOCCC(=O)N3CCC(C(=O)O)CC3)c3ccccc43)cc2c1]

67 68
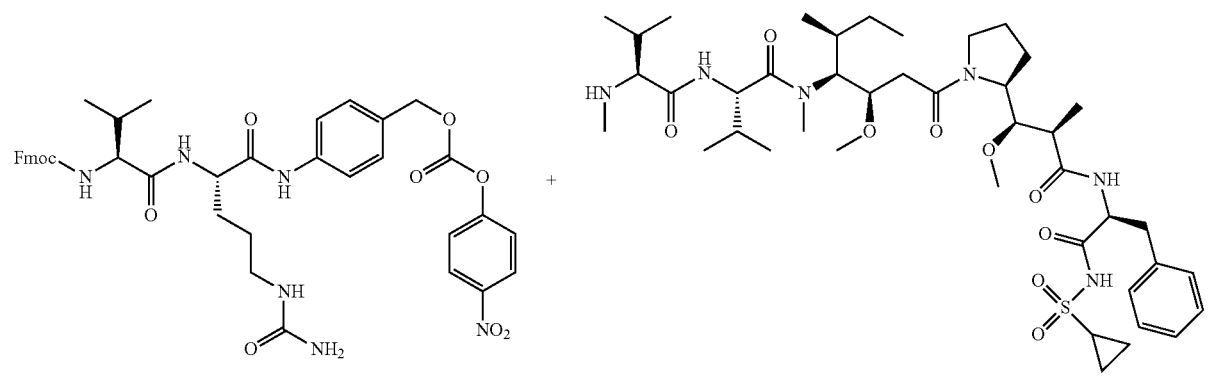
| HOBt, DIEA
↓
| Piperidine, DMF
↓
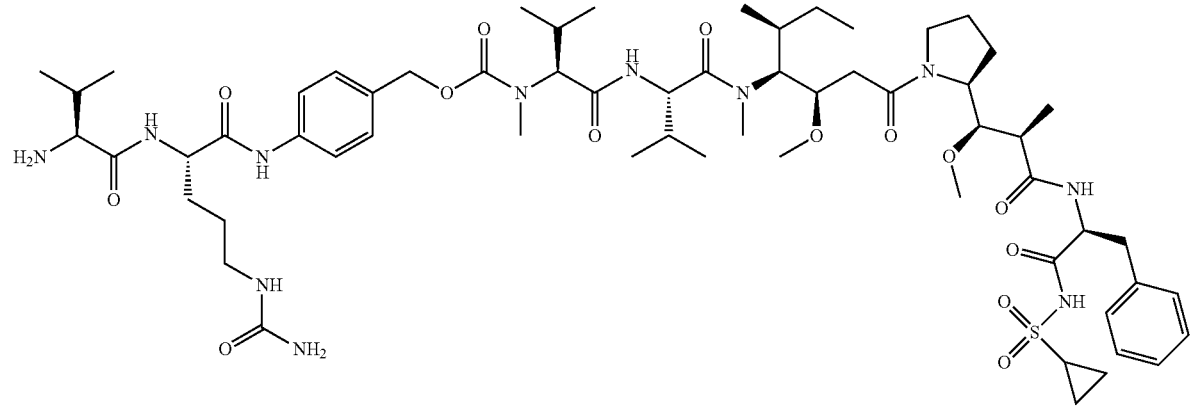
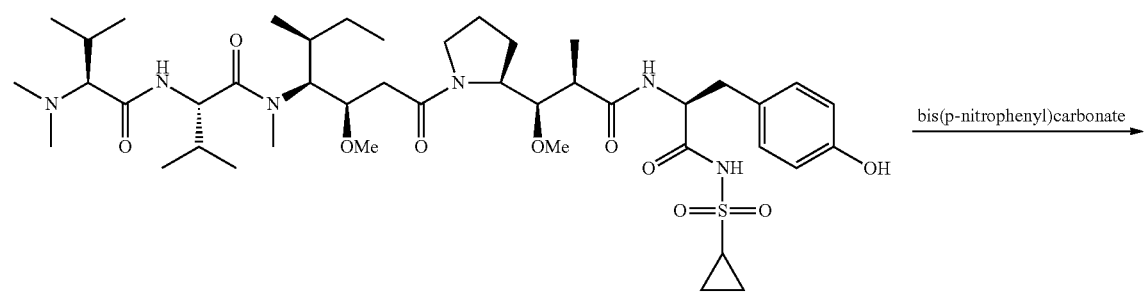  bis(p-nitrophenyl)carbonate →
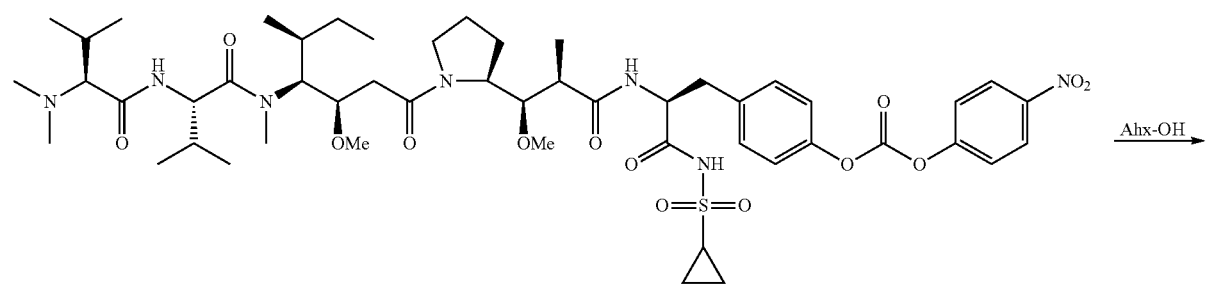  Ahx-OH →

-continued
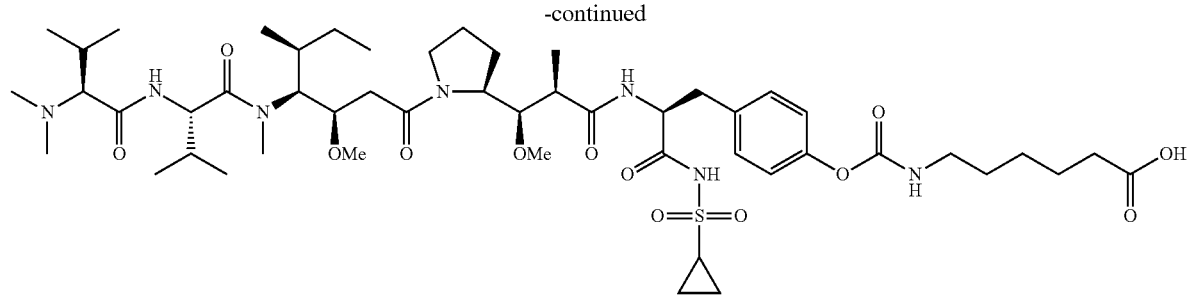
Method 1-2: Linker and Drug Connected Via Reductive Alkylation Reaction (General Procedure E)
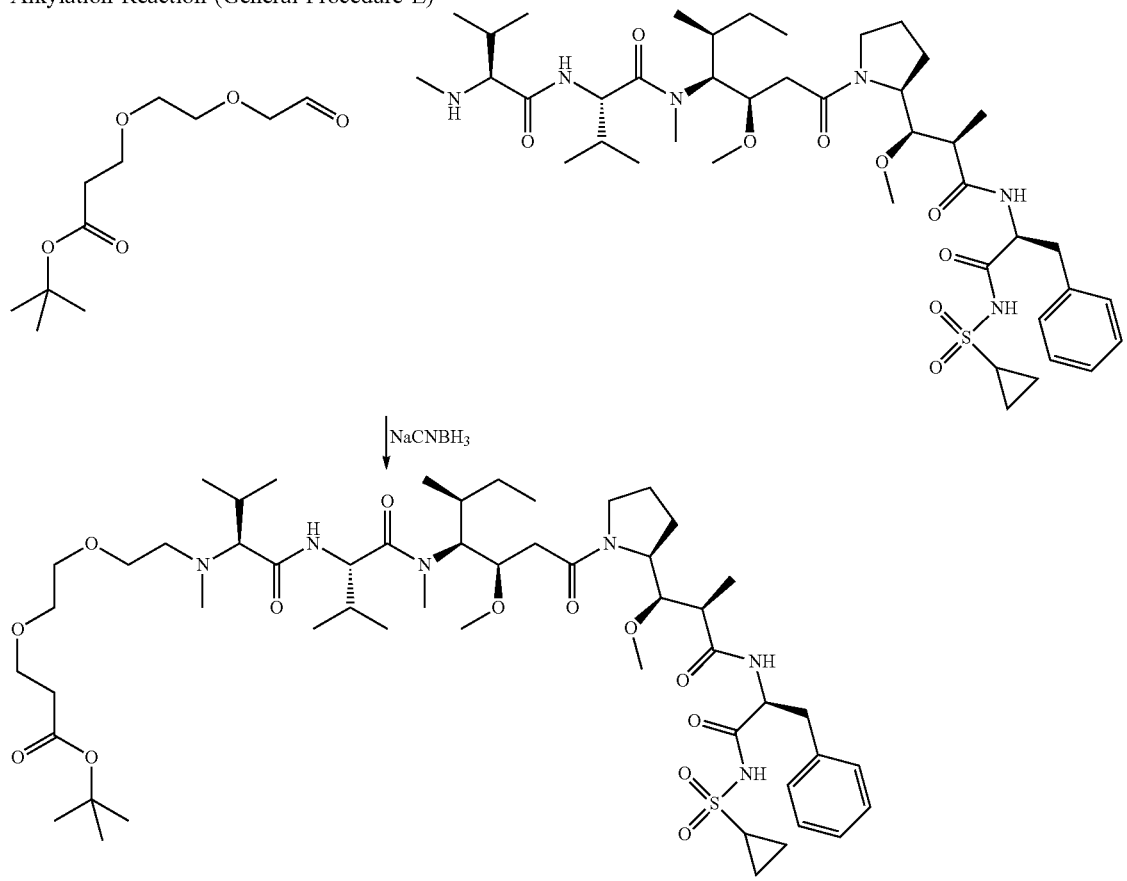
Method 1-3. Active Molecule Containing a Carboxylic Acid Moiety Connected to an Alkoxyamino Linker Via Formation of Hydroxamate (General Procedure A or B), Followed by Removal of Protective Groups.
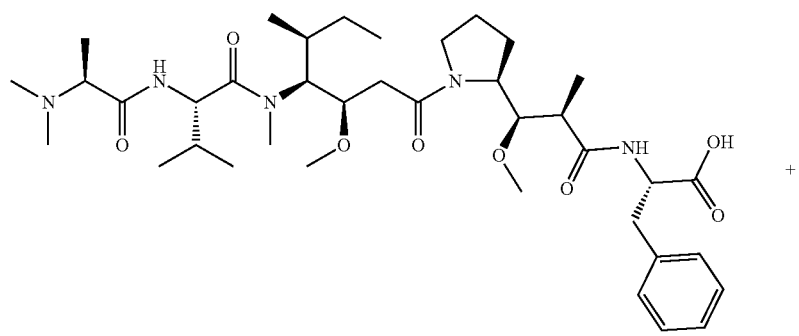

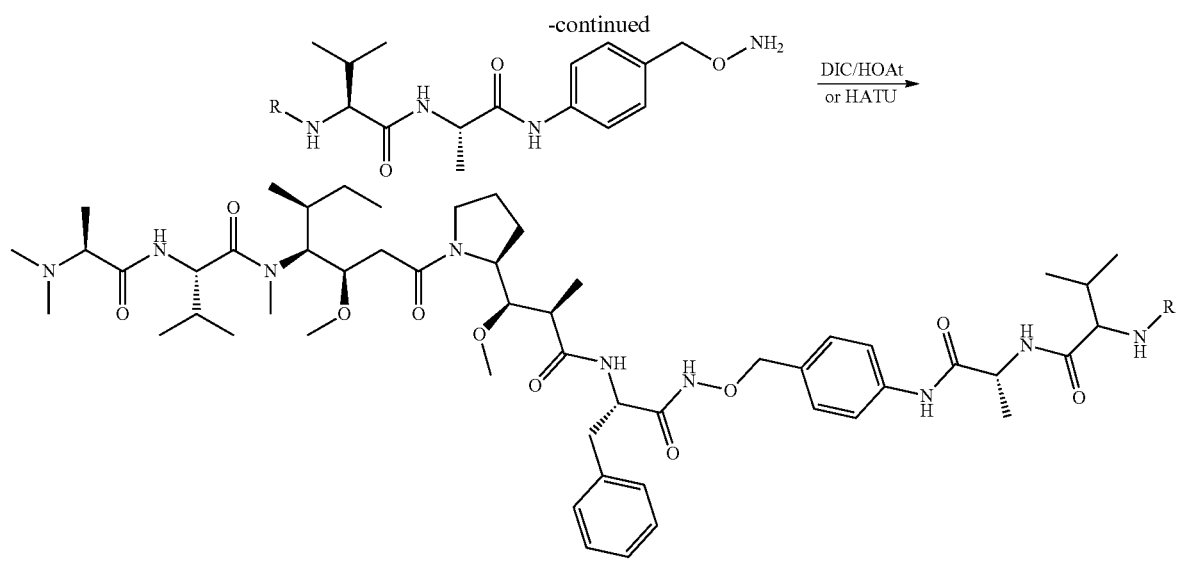
For active molecules that are hydroxamic acids, the above method still can be employed since the construct will release hydroxamic acid under enzymatic cleavage conditions. The reaction needs to start from its corresponding carboxylic acid.
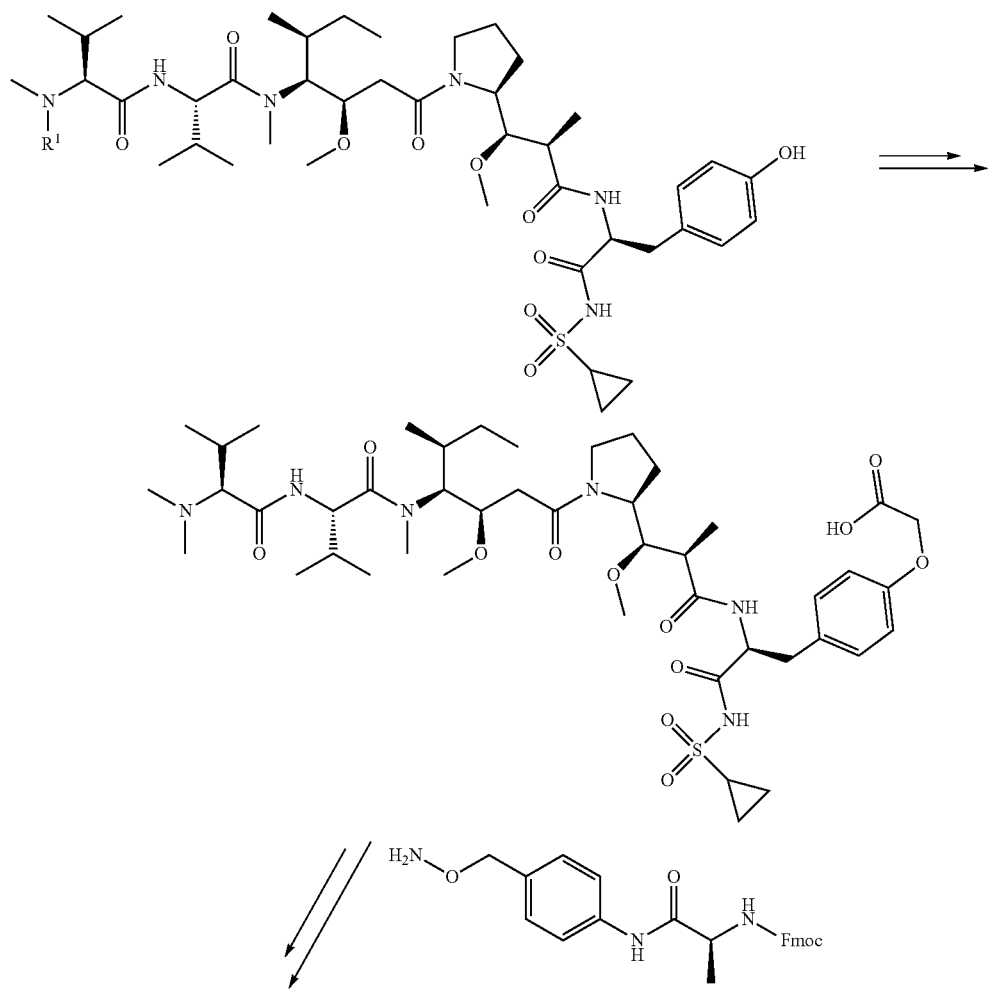

-continued
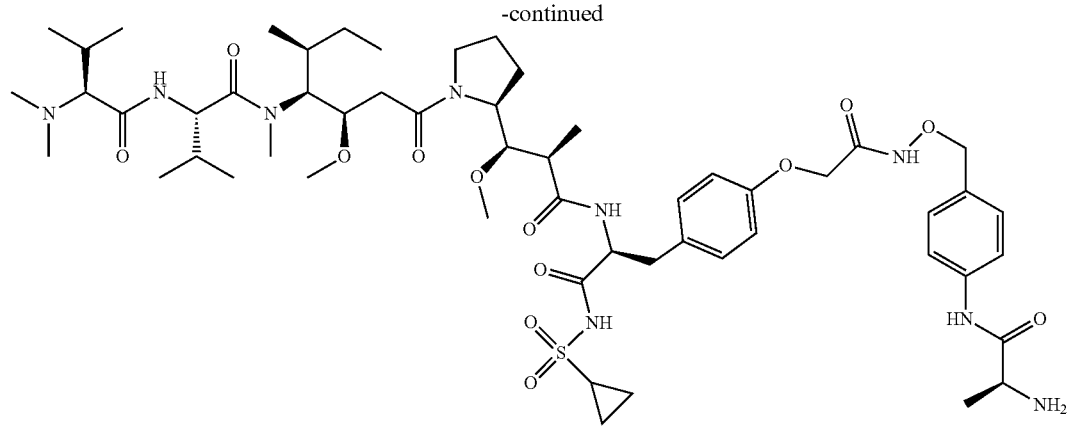
Step 2. Introducing Functional Groups to L1-(L2-D)
Methods to Introduce Functional Groups that Suitable for Conjugation Reaction, but not Limited to:
Method 2-1. Compounds Bearing Free Amino Group to React with an Cyclic Anhydride to Introduce Carboxylic Acid (General Procedure H).
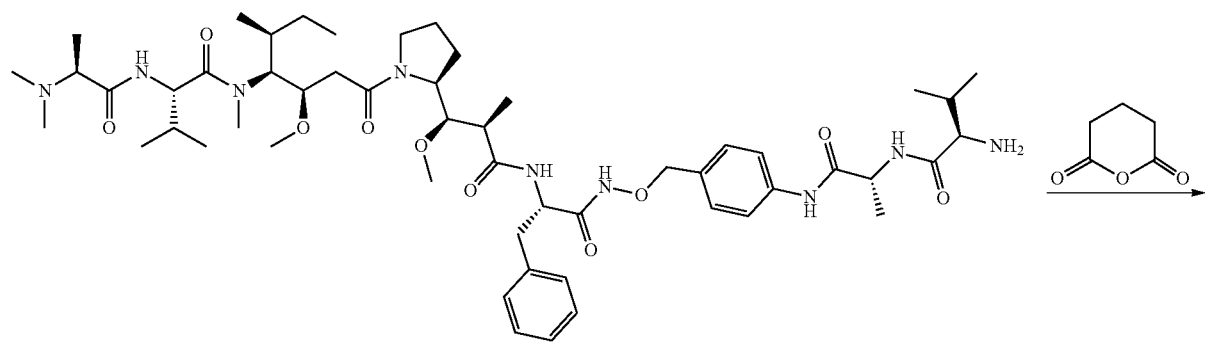
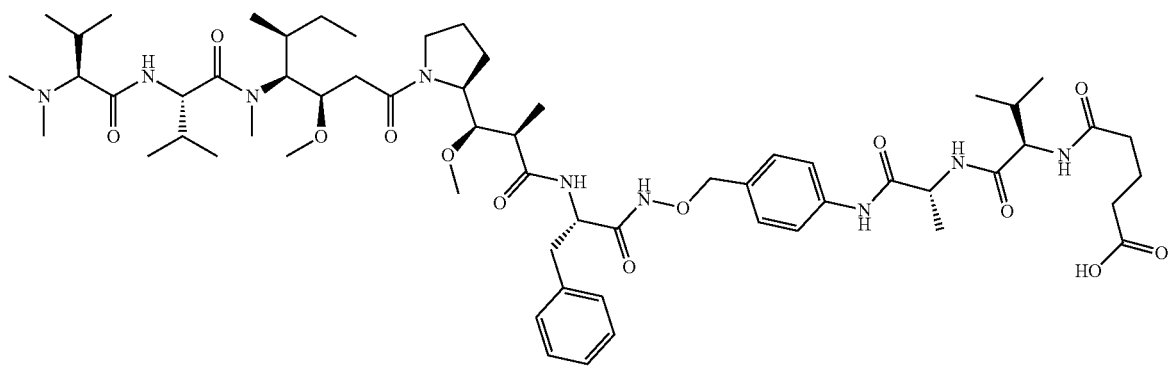

Method 2-2. Compounds Bearing Free Amino Group to React with a Di-Acid to Introduce Carboxylic Acid (General Procedure B).
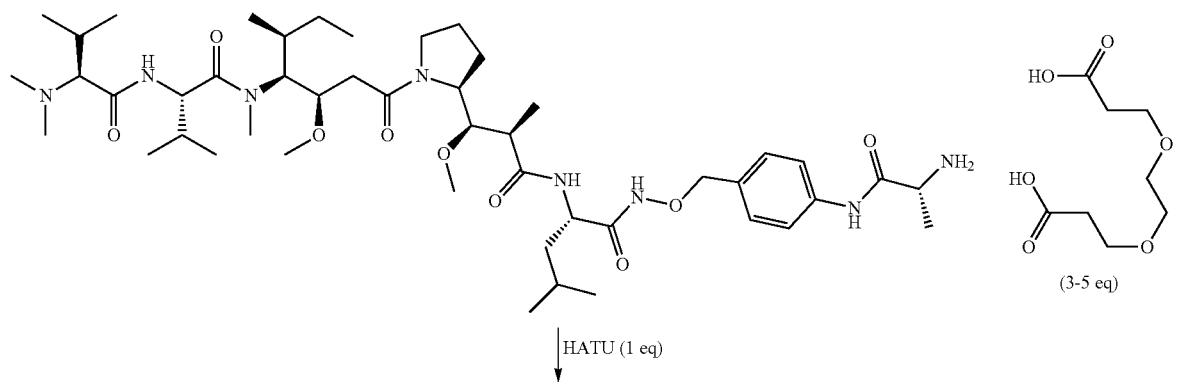
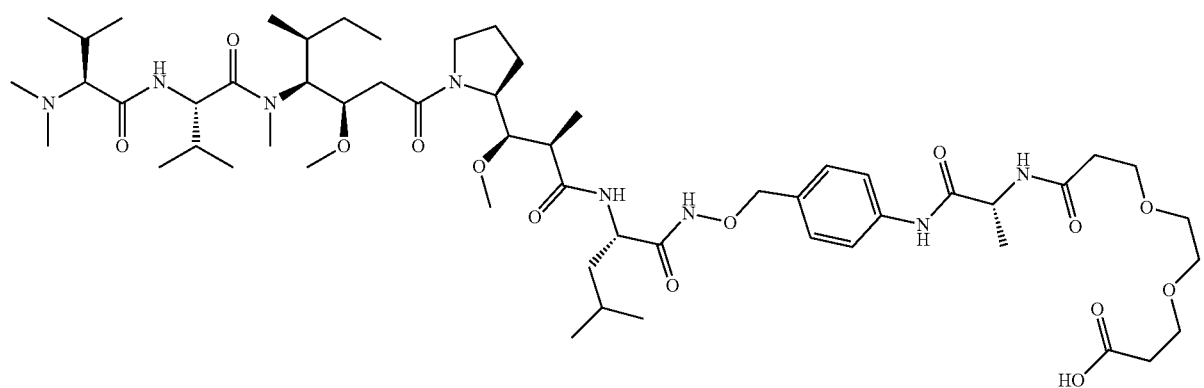
Method 2-3. Removal of Carboxylic Acid Protective Group to Reveal the Free Carboxylic Acid (General Procedure C, F)
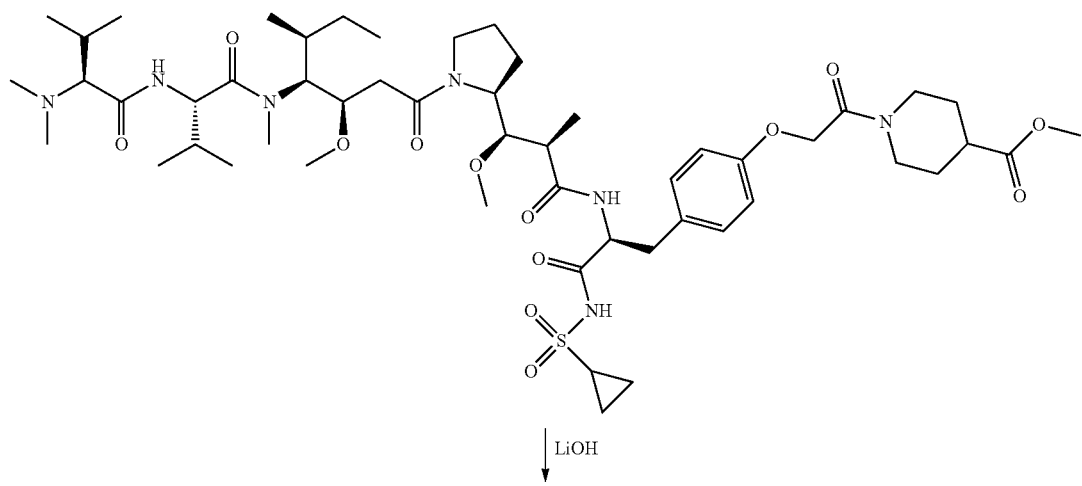

77 78
-continued
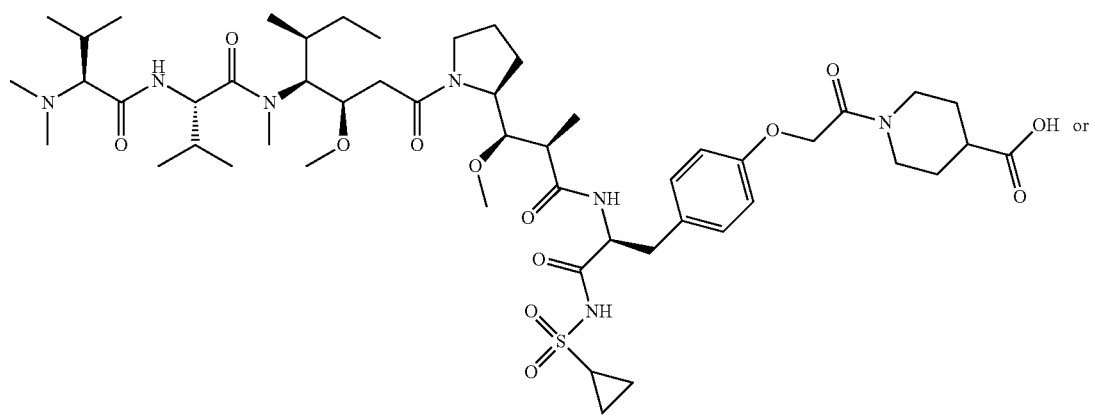
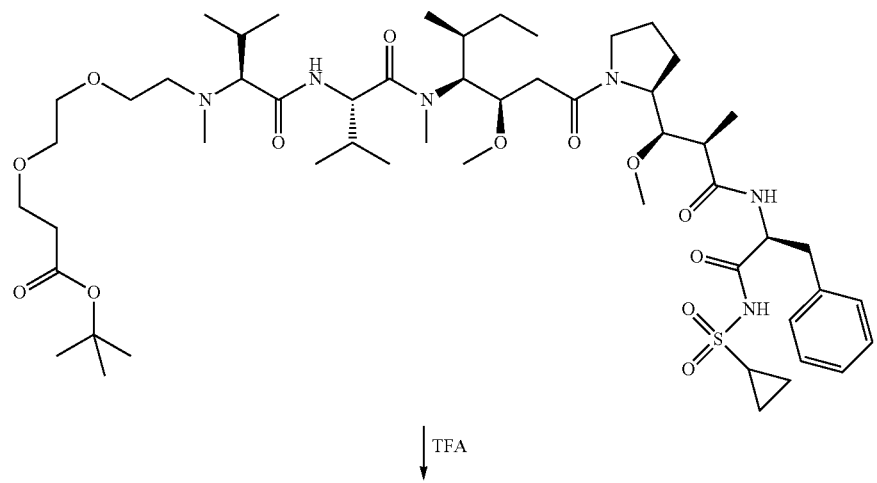
↓ TFA
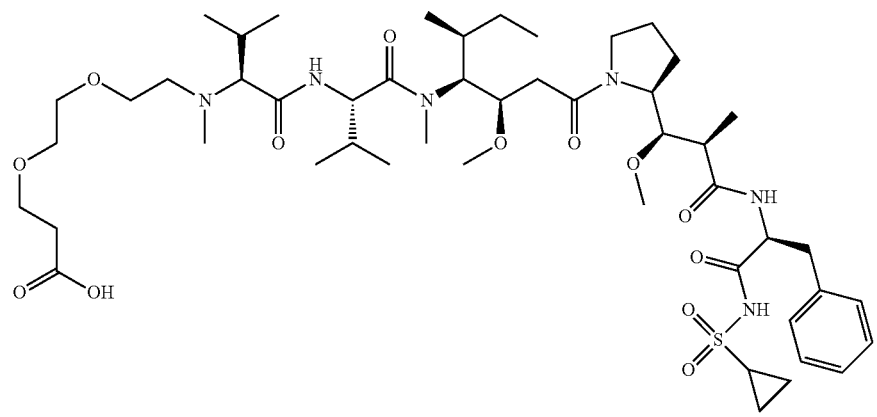

Method 2-4. Introduction of a Cyclic Carboxylic Acid Moiety Using a Linear Carboxylic Acid as a Starting Material
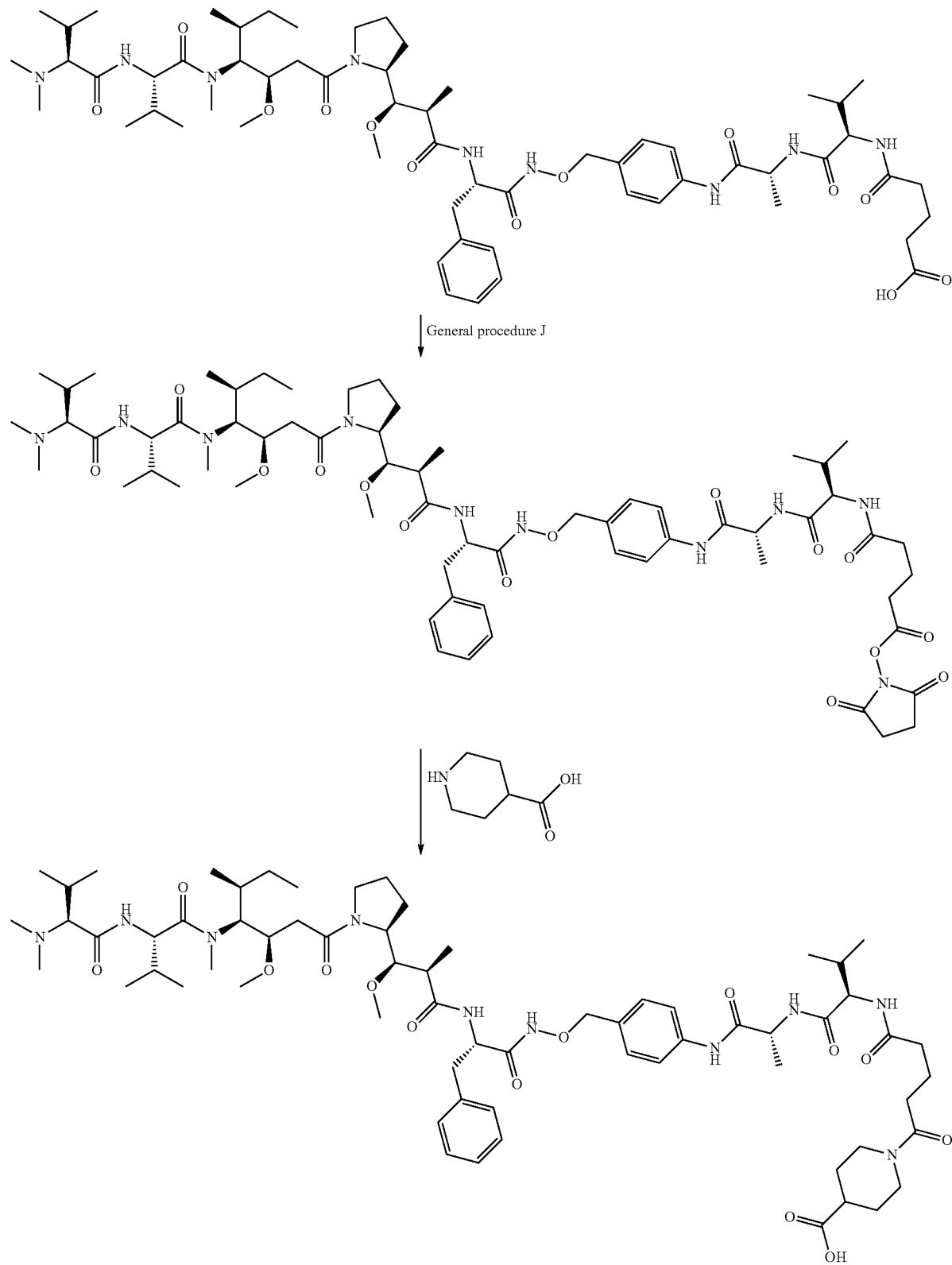

The NHS ester (20 mg) was dissolved in acetonitrile/water (6/4, v/v) and a solution of piperidine 4-carboxylic acid (12 mg) in sat. aq. sodium bicarbonate (0.3 mL) was added. The mixture was stirred at room temperature for 2 h and purified directly by RP-HPLC to give the desired product as a white solid after lyophilization (18 mg). MS found 1261.5 (M+H)+.

Method 2-5. Reductive Alkylation of a Primary Amine with a Dialdehyde Bearing a Carboxylic Acid Moiety (General Procedure E)

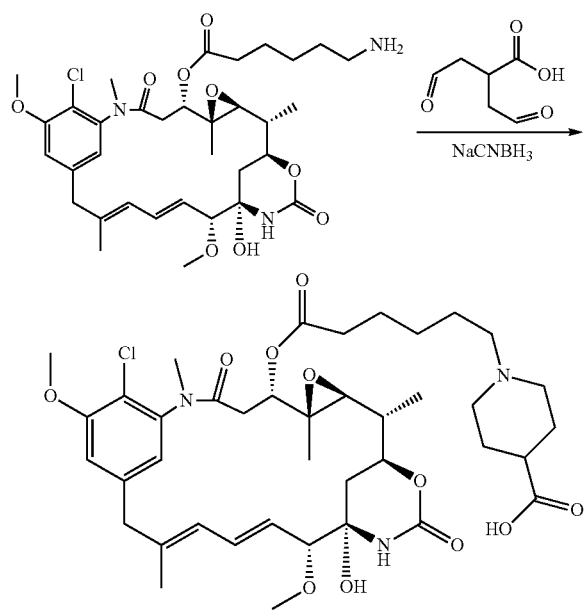

The amine (NH$_2$-Ahx-Maytansinol) (20 mg) was dissolved in acetonitrile (2 mL) and 1 mL of NaOAc buffer (100 mM, pH=4.0) was added. The dialdehyde (0.5 M solution in water, 0.2 mL) was added, followed by NaCNBH$_3$ (10 mg). The reaction mixture was stirred at room temperature for 30 mins and purified directly by RP-HPLC to give the desired acid (16 mg) as a white solid after lyophilization. MS found: 790.5 (M+H)+.

The Dialdehyde Carboxylic Acid was Synthesized According to the Following Scheme:

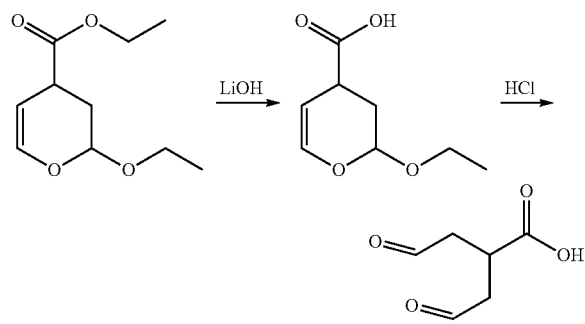

The ester, 2H-Pyran-4-carboxylic acid, 2-ethoxyl-3,4-dihydro-ethyl ester was synthesized according to a literature procedure (*Chem Communications*, (1) 25-26, 1998) was saponified using General procedure F, followed by treatment with 1N aq. HCl at room temperature for 1 h. The aq. solution of dialdehyde was used directly without further purification.

Step 3. Introducing the Final Functional Groups Prior to Conjugation

Methods of Introduction of Final Reactive Group Prior to Conjugation Reaction, but not Limited to:

Method 3-1. Activation of a Carboxylic Acid to its Corresponding Activated Form

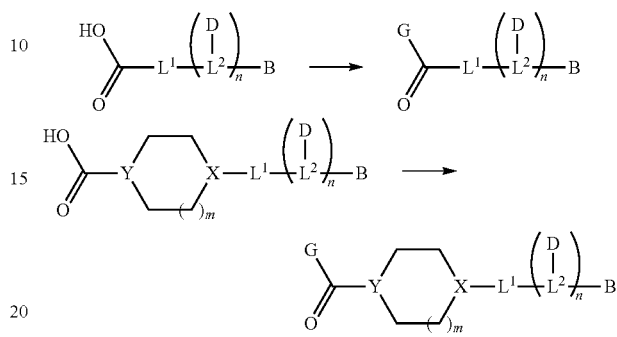

G is a leaving group selected from —F, —Cl, —Br, —I, —N$_3$, —OR (R=alkyl, aryl, heteroaryl, substituted aryl, substituted heteroaryl), SR (R=substituted alkyl, substituted aryl heteroaryl, substituted aryl, substituted heteroaryl), —ON(R$^1$)R$^2$, (R$^1$, R$^2$ are each independently selected from —(C=O)—R, R=H, alkyl, aryl, heteroaryl, substituted aryl, substituted heteroaryl or R$^1$ and R$^2$ are connected to form a cyclic structure, or R$^1$=R$^2$=(=C—R), RC(=O)O—, and RSO$_2$—O— (R=alkyl, aryl, heteroaryl, substituted aryl, substituted heteroaryl).

The carboxylic acid can be activated using a variety of methods to afford an activated form. For example, the carboxylic acid can be activated using the following methods: A) *Tetrahedron* 61 (2005) 10827-10852; B) Beckwith, A. L. J. In The Chemistry of Amides; Zabicky, J., Ed.; Synthesis of Amides; Interscience: London, 1970; pp 105-109; C) Handbook of Reagents for Organic Synthesis: Activating Agents and Protecting Groups; Pearson, A. J., Roush, W. R., Eds.; Wiley: New York, 1999; pp 370-373; D) Lloyd-Williams, P., Albericio, F., and Giralt, E. (1997). Chemical approaches to the synthesis of peptide and proteins (Series ed. C. W. Rees). CRC Press, New York; E) Peptide chemistry: A practical textbook: By M Bodansky. Springer-Verlag, Heidelberg. 1988; and F) The practice of peptide synthesis, 2nd ed., by M. Bodansky and A. Bodansky, Springer-Verlag, New York, each of which is incorporated herein by reference in its entirety.

Method 3-2. Introduction of a Dialdehyde Moiety for Conjugation Reaction

The ethoxypyrane derivative was treated with aq. acid to give the desired dialdehyde.

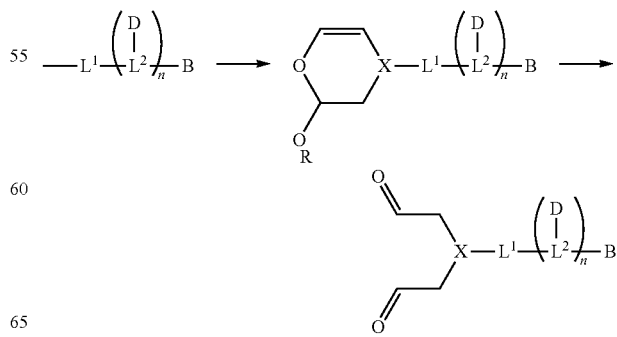

Example I. Synthesis of Compound 10

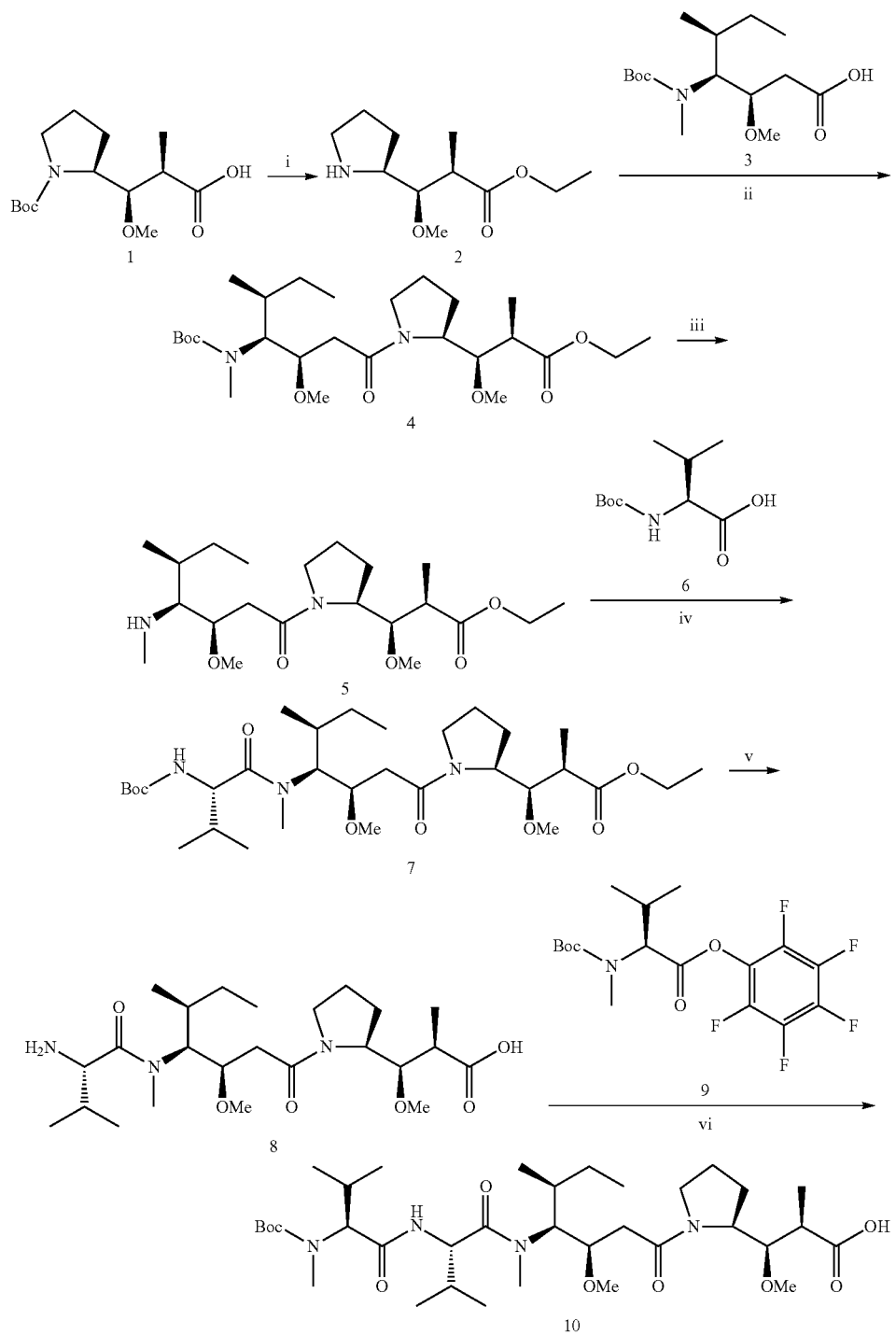

Scheme I. Reagents and conditions: i. SOCl₂, EtOH; ii. DEPC, TFA, DCM; iii. TFA, DCM; iv. BrOP, DCM, DIEA; v. TFA, DCM; iv. DIEA, DCM, HOBt To a solution of compound 1 (23.4 g, 81.53 mmol) in dry EtOH (200 mL) was added SOCl₂ (100 mL) at 0° C. The mixture was stirred for overnight and the solvent was removed by evaporation in vacuo. The residue was immediately used for the next step without further purification. To a solution of compound 2 (81.53 mmol), compound 3 (50 g, 163.1 mmol) in dry DMF (150 mL) was added DEPC (15.9 g, 97.8 mmol), TEA (41 g, 0.408 mol) at 0° C. The mixture was stirred for 2 h at 0° C. Then the mixture was stirred overnight at room temperature. Solvent was removed by evaporation in vacuo. The residue was diluted with ethyl acetate-toluene (2:1, 900 mL) and washed with 1M $KHSO_4$, water, sat. $NaHCO_3$, and brine. The organic Lyser was dried and concentrated to give a residue, which was purified by column (hexanes:ethyl acetate:DCM=5:1:1) to give 38 g of compound 4.

To a solution of Boc-Val-OH (30.6 g, 0.142 mol), compound 5 (from 25 g of compound 4) in DCM (400 mL) was added BrOP (28 g, 70.87 mmol), DIEA (30 g, 0.236 mol) at 0° C. The mixture was shielded from light and stirred for 0.5 h at 0° C. Then the mixture was stirred for 48 h at room temperature. The solvent was removed by evaporation in vacuo. The residue was diluted with ethyl acetate-toluene (3:1, 900 mL) and washed with 1M $KHSO_4$, water, sat. NaHCO₃, and brine. The organic Lyser was dried and concentrated to give a residue, which was purified by silica gel column (hexanes:ethyl acetate:DCM=3:1:1) to give 22 g of compound 7.

To a solution of compound 7 (40 g, 66.7 mmol) in THF (600 mL) was added a mixture of LiOH (14 g, 0.33 mol) in water (300 mL) below 10° C. The mixture was stirred for 5 days at 25° C. THF was removed by evaporation. The aqueous Lyser was washed with $Et_2O$ (200 mL×3). The aqueous Lyser was acidified to pH 2 with 1N HCl at 0° C., the mixture was extracted with ethyl acetate and the organic Lyser was washed with water and brine. The organic Lyser was dried and concentrated to give a residue, which was purified by Prep-HPLC to give 14 g of compound 8.

To a solution of compound 8 (3 g) in DCM (100 mL) was added compound 9 (3 g, prepared according to General procedure J from Boc-N-Me-Val-OH using EDC and pentafluorophenol). DIEA (2.6 mL) was added, followed by HOBt (cat. 100 mg) and the reaction mixture was stirred at room temperature for 16 h. The solvents were removed under reduced pressure and the residue was purified on a silica gel column to give compound 10 as a white powder (3.1 g). MS m/z Calcd for $C_{35}H_{64}N_4O_9$ 684.5. Found 707.6 ([M+Na]⁺).

Example II-1. Synthesis of Compound 13

SCHEME II-1

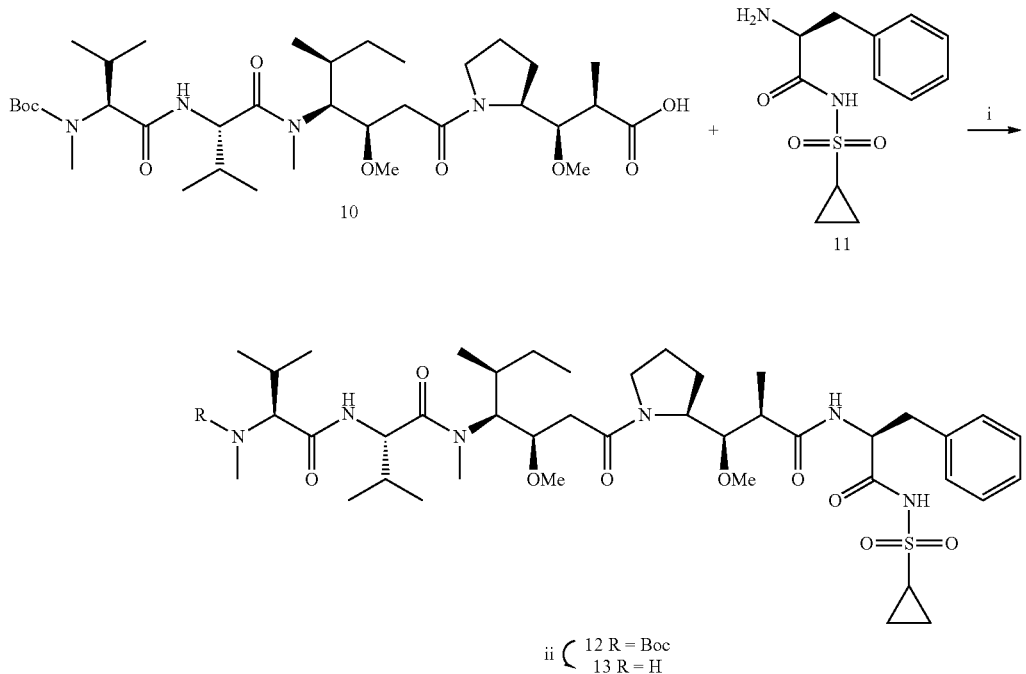

Scheme II-1. Reagents and conditions: i. DIC/HOAt, DMF, rt, 16 h; ii. HCl/Dioxane The amino acid sulfonamide derivatives 11 were synthesized according to previously reported procedure (ARKIVOC 2004 (xii) 14-22, or WO 2007146695) using Boc protected amino acid and cyclopropyl/methyl sulfonamide, followed by removal of Boc (General procedure C)

Compound 13 was synthesized using the general procedures described above as following: DIC/HOAt mediated amide bond formation (General procedure B) between Boc-N-Me-Val-Val-Dil-Dap-OH (compound 1) and amine 11, followed by removal of Boc (General procedure C). The final compound was purified by reverse phase HPLC to give compound 13 as a white powder after lyophilization. MS m/z Calcd for $C_{42}H_{70}N_6O_9S$ 834.5. Found 835.6 ([M+H]⁺).

Example II-2. Synthesis of Compounds 16

SCHEME II-2

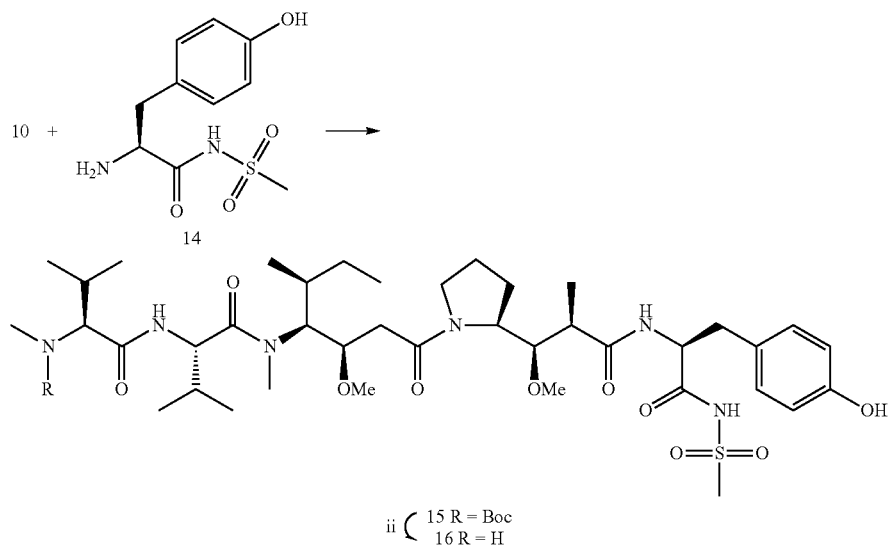

Scheme II-2. Reagents and conditions: i. DIC/HOAt, DMF, rt, 16 h; ii. HCl/Dioxane The amino acid sulfonamide derivatives 14 were synthesized according to previously reported procedure (ARKIVOC 2004 (xii) 14-22, or WO 2007146695) using Boc protected amino acid and cyclopropyl/methyl sulfonamide, followed by removal of Boc (General procedure C).

Compound 16 was synthesized using the general procedures described above as following: DIC/HOAt mediated amide bond formation (General procedure B) between Boc-N-Me-Val-Val-Dil-Dap-OH (compound 10) and amine 14, followed by removal of Boc (General procedure C). The final compound was purified by reverse phase HPLC to give compound 16 as a white powder after lyophilization. MS m/z Calcd for $C_{41}H_{70}N_6O_{10}S$ 838.5. Found 839.6 ([M+H]$^+$).

Example II-3. Synthesis of Compound 20

SCHEME IIC

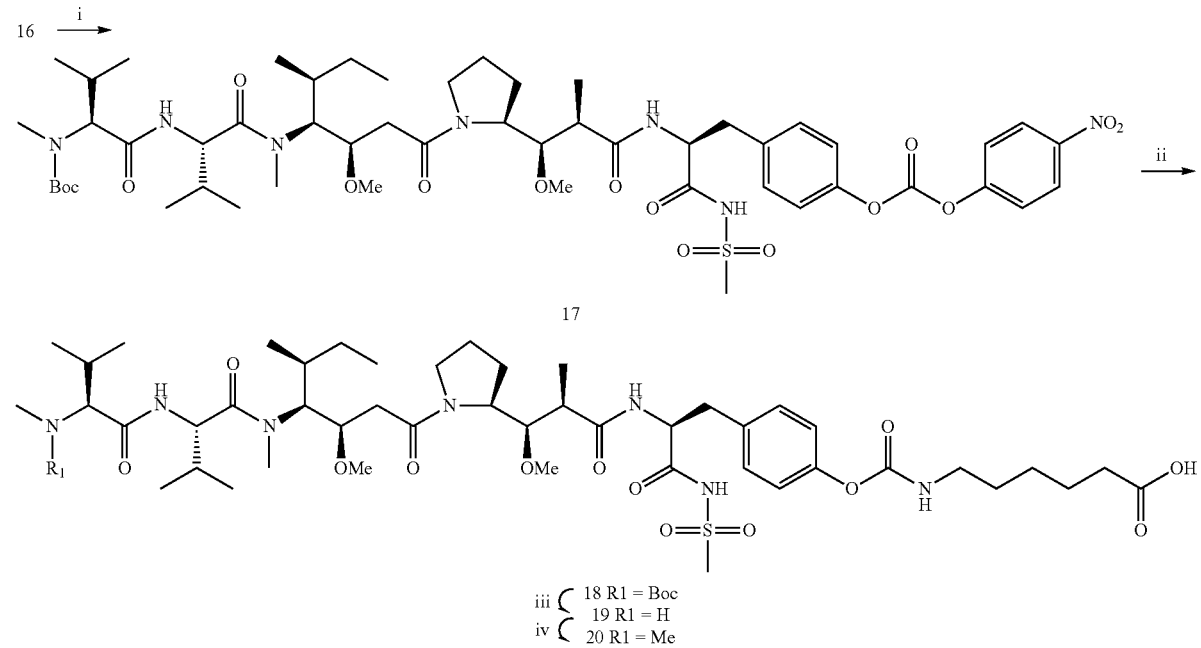

Scheme IIC. Reagents and conditions: i. bis(nitrophenyl) carbonate, DIEA, THF/DMF, r.t.; ii. 6-aminohexanoic acid, NaHCO$_3$ (aq.); iii. HCl/Dixoane (4N); iv. HCHO, NaCNBH$_3$, DMF, HOAc;

The phenol 16 (1 mmol) was treated with 3 eq of bis(p-nitrophenyl)carbonate to form the activated carbonate 17 (general procedure G). The crude product was used directly without further purification. 6-Aminohexanoic acid (5 eq) was dissolved in sat. aq. NaHCO$_3$ (5 mL) and the solution was added. The reaction mixture was stirred at room temperature for 16 h. Citric acid (aq. 10%) was added to acidify the reaction (pH=4-5) and then diluted with EtOAc (150 mL). Organic Lyser was dried (over Na$_2$SO$_4$) and concentrated to give the crude product 18 which underwent the following procedures: removal of Boc (General procedure C), reductive alkylation using HCHO. The final product was purified by RP-HPLC to give compound 20 as a white powder after lyophilization. MS m/z Calcd for C$_{48}$H$_{81}$N$_7$O$_{13}$S 995.6. Found 996.4 ([M+H]$^+$).

Example III. Synthesis of Alkoxyamine Linkers 24, 25, 26, and 27

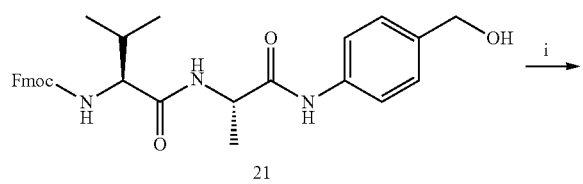

SCHEME III

Scheme III. Reagents and conditions: i. SOCl$_2$, THF, 1 h; ii. N-hydroxyphthalimide, NaHCO$_3$, DMF, rt, 48 h; iii. NH$_2$NH$_2$·H$_2$O, HOAc, DMF.

Example III-1. Synthesis of Compound 24

To a stirred solution of Fmoc-VA-PAB (21) (*Bioconjugate Chem.*, 2002, 13, 855-859) (9 g, 15 mmol) in THF (200 mL) was added thionyl chloride (18 mmol) dropwise. After the addition was complete, the reaction mixture was stirred at room temperature for 1 h. TLC analysis (ethyl acetate/hexane, 1/1, v/v) showed the completion of the reaction. The solvents were removed under reduced pressure and the residue was washed with hexanes (100 mL) to give compound 22 as a slightly yellowish solid (8.8 g).

Compound 22 (6.2 g, 10 mmol) was dissolved in anhydrous DMF (100 mL). N-Hydroxy-phthalimide (3.2 g, 20 mmol) was added, followed by solid NaHCO$_3$ (3.4 g, 40 mmol). The reaction mixture was stirred at room temperature for 48 h. TLC analysis showed that most of compound 61 was consumed. The reaction was then diluted with ethyl acetate (500 mL) and washed successively with sat. aq. NaHCO$_3$ (3×200 mL) and brine (200 mL). The organic Lyser was dried and concentrated to give compound 23 as a tan solid, which was used directly without further purification.

The crude compound 23 from previous step was dissolved in DMF (100 mL). HOAc (6 mL) was added, followed by hydrazine hydrate (5 mL). The reaction was stirred at room temperature for 1 h. LC/MS showed the completion of the reaction. The reaction mixture was then poured into a beaker containing 1 L of water under stirring. The precipitated solid was collected via filtration and washed twice with water to give compound 24 as a white solid (purity>85%, can be used directly). Pure compound 63 was obtained after RP-HPLC purification. MS m/z Calcd for $C_{30}H_{34}N_4O_5$ 530.3. Found 531.4 ([M+H]$^+$).

Example III-2. Synthesis of Compound 25

Compound 25 was synthesized starting from compound Fmoc-VC-PAB (*Bioconjugate Chem.*, 2002, 13, 855-859) using the procedures described above for the synthesis of compound 25. MS m/z Calcd for $C_{33}H_{40}N_6O_6$ 616.3. Found 617.5 ([M+H]$^+$).

Example III-3. Synthesis of Compound 26

Compound 26 was synthesized starting from compound Fmoc-A-PAB (synthesized according to the procedure reported: *Bioconjugate Chem.*, 2002, 13, 855-859) using the procedures described above for the synthesis of compound 26. MS m/z Calcd for $C_{25}H_{25}N_3O_4$ 431.2. Found 432.6 ([M+H]$^+$).

Example III-4. Synthesis of Compound 27

Compound 27 was synthesized starting from compound Fmoc-Ahx-PAB using the procedures described above for the synthesis of compound 27. MS m/z Calcd for $C_{28}H_{31}N_3O_4$ 473.2. Found 474.3 ([M+H]$^+$).

Example IV. Synthesis of -L$^1$-(L$^2$-D)-

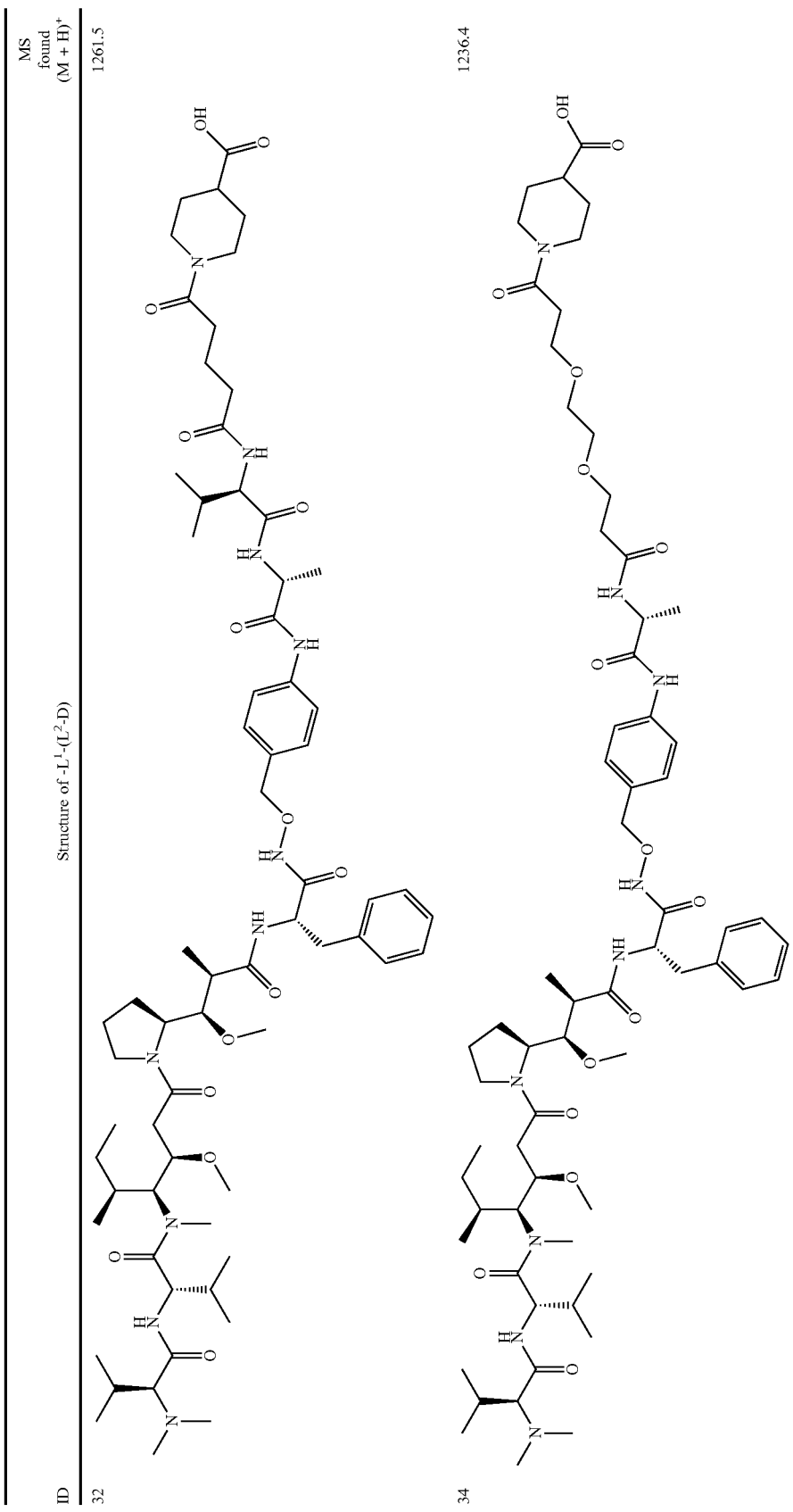

-continued

| ID | Structure of -L¹-(L²-D) | MS found (M + H)⁺ |
|---|---|---|
| 35 | | 1348.0 |
| 36 | | 1162.6 |

-continued

| ID | Structure of -L¹-(L²-D) | MS found (M + H)⁺ |
|---|---|---|
| 37 | | 1204.5 |
| 38 | | 1202.4 |

| ID | Structure of -L¹-(L²-D) | MS found (M+H)⁺ |
|---|---|---|
| 39 | | 1228.2 |
| 40 | | 1374.0 |

-continued

| ID | Structure of -L¹-(L²-D) | MS found (M + H)⁺ |
|---|---|---|
| 41 | | 1385.6 |
| 42 | | 1389.4 |

-continued

| ID | Structure of -L¹-(L²-D) | MS found (M + H)⁺ |
|---|---|---|
| 43 | | 1329.7 |
| 44 | | 1148.5 |

| ID | Structure of -L¹-(L²-D) | MS found (M + H)⁺ |
|---|---|---|
| 45 | 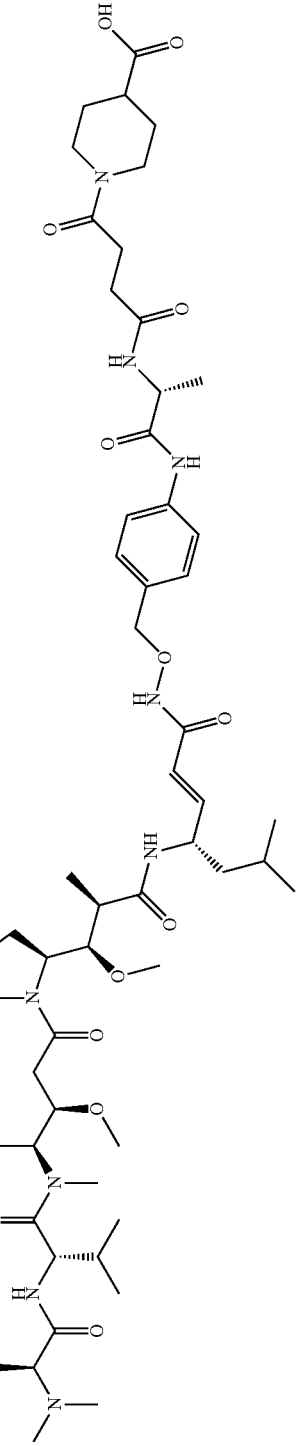 | 1140.4 |

SCHEME IV
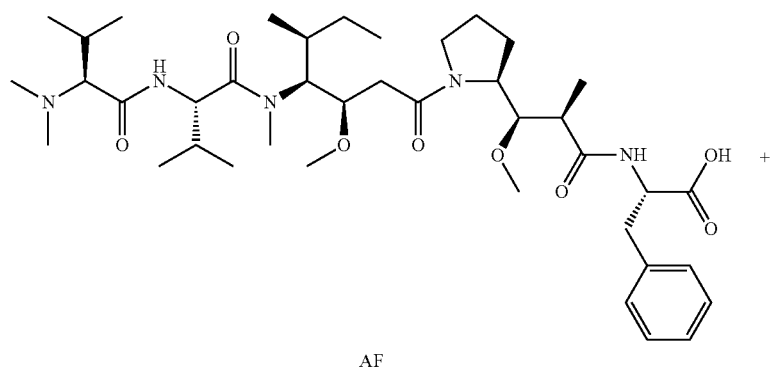
AF
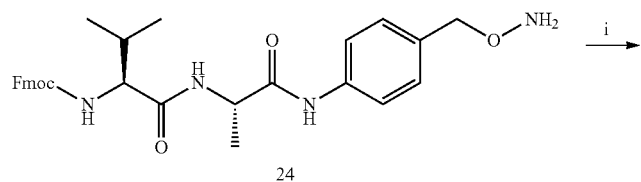
24
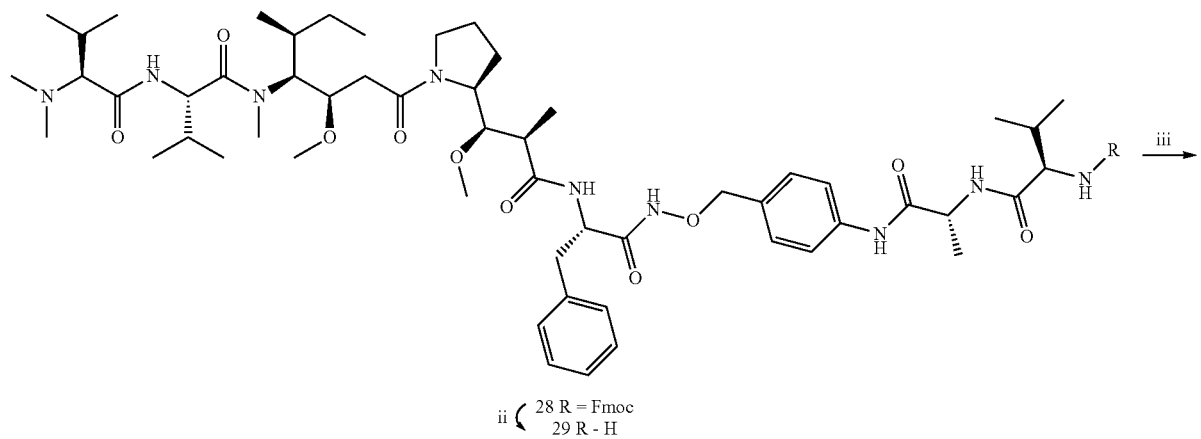
ii ⎰ 28 R = Fmoc
   ⎱ 29 R - H
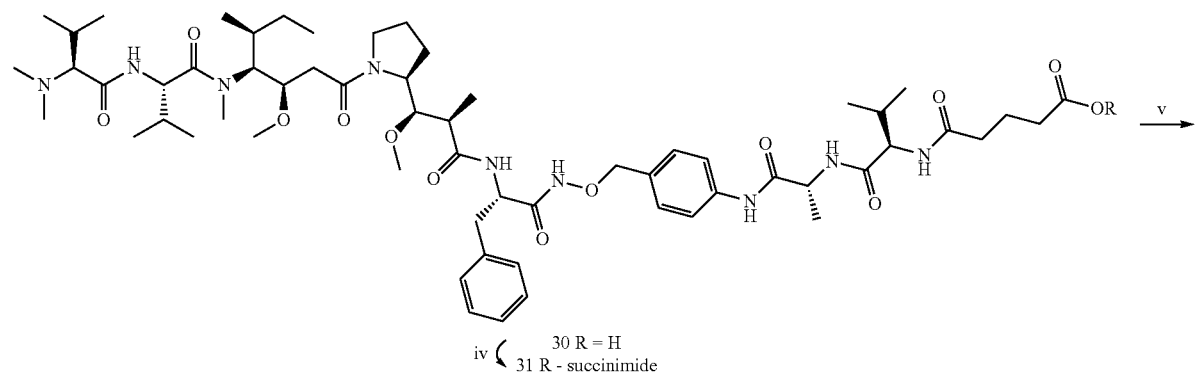
iv ⎰ 30 R = H
   ⎱ 31 R - succinimide -continued

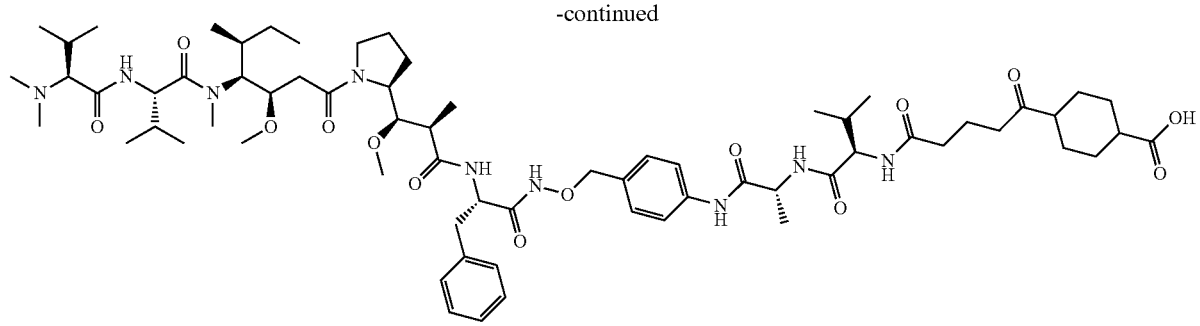

32

Scheme IV. Reagents and conditions: i. DIC, HOAt, DMF, r.t.; ii. Piperidine, DMF; iii. Glutaric anhydride, DIEA, DMF, rt; iv. EDC, HOSu, DCM, DMF, r.t.
iv. Piperidine 4-carboxylic acid, NaHCO₃, MeCN/water.

Example IV-1. Synthesis of Compound 32

Compound 32 was synthesized using the general procedures described above as following: DIC/HOAt mediated amide bond formation (General procedure B) between Auristatin F and compound 24, followed by removal of Fmoc (General procedure D), reaction with glutaric anhydride (General procedure H), and conversion of the acid to the corresponding NHS ester (General procedure J).

The NHS ester (20 mg) was dissolved in acetonitrile/water (6/4, v/v) and a solution of piperidine 4-carboxylic acid (12 mg) in sat. aq. sodium bicarbonate (0.3 mL) was added. The mixture was stirred at room temperature for 2 h and purified directly by RP-HPLC to give the desired product as a white solid after lyophilization (18 mg). MS found 1261.5 (M+H)⁺.

Example IV-2. Synthesis of Compound 34

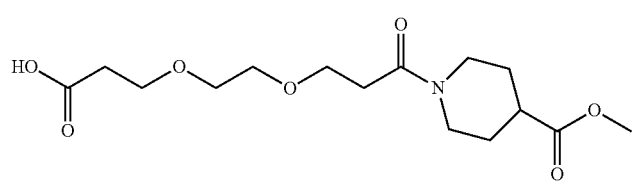

33

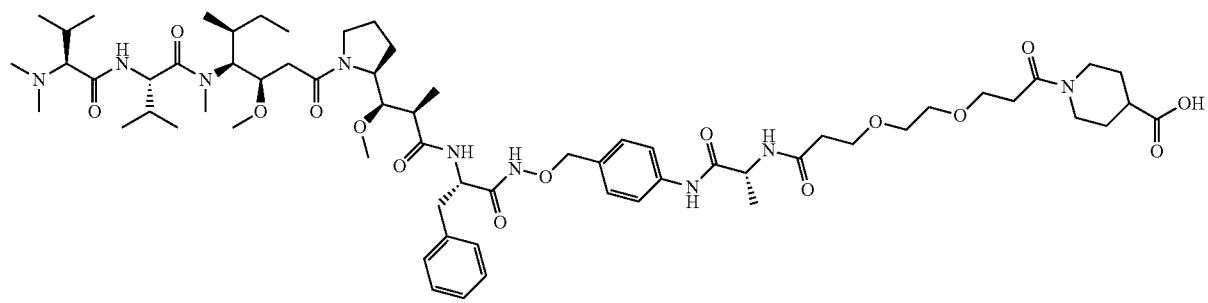 [SMILES: CC[C@H](C)[C@@H]([C@@H](CC(=O)N1CCC[C@H]1[C@H](OC)[C@@H](C)C(=O)N[C@@H](Cc1ccccc1)C(=O)NOCc1ccc(NC(=O)[C@@H](C)NC(=O)CCOCCOCCC(=O)N2CCC(C(=O)O)CC2)cc1)OC)N(C)C(=O)[C@@H](NC(=O)[C@H](C(C)C)N(C)C)C(C)C]

34

Compound 34 was synthesized using the general procedures described above as following: DIC/HOAt mediated amide bond formation (General procedure B) between compound dimethyl auristatin F and compound 26, followed by removal of Fmoc (General procedure D), and amide formation with acid 33 using HATU (General procedure A), followed by saponification to remove the methyl ester (General procedure F). The final compound was purified by reverse phase HPLC to give compound 34 as a white powder after lyophilization. MS m/z Calcd for $C_{64}H_{101}N_9O_{15}$ 1235.7. Found 1236.4 ([M+H]⁺).

Example V. Synthesis of -L¹-(L²-D)-

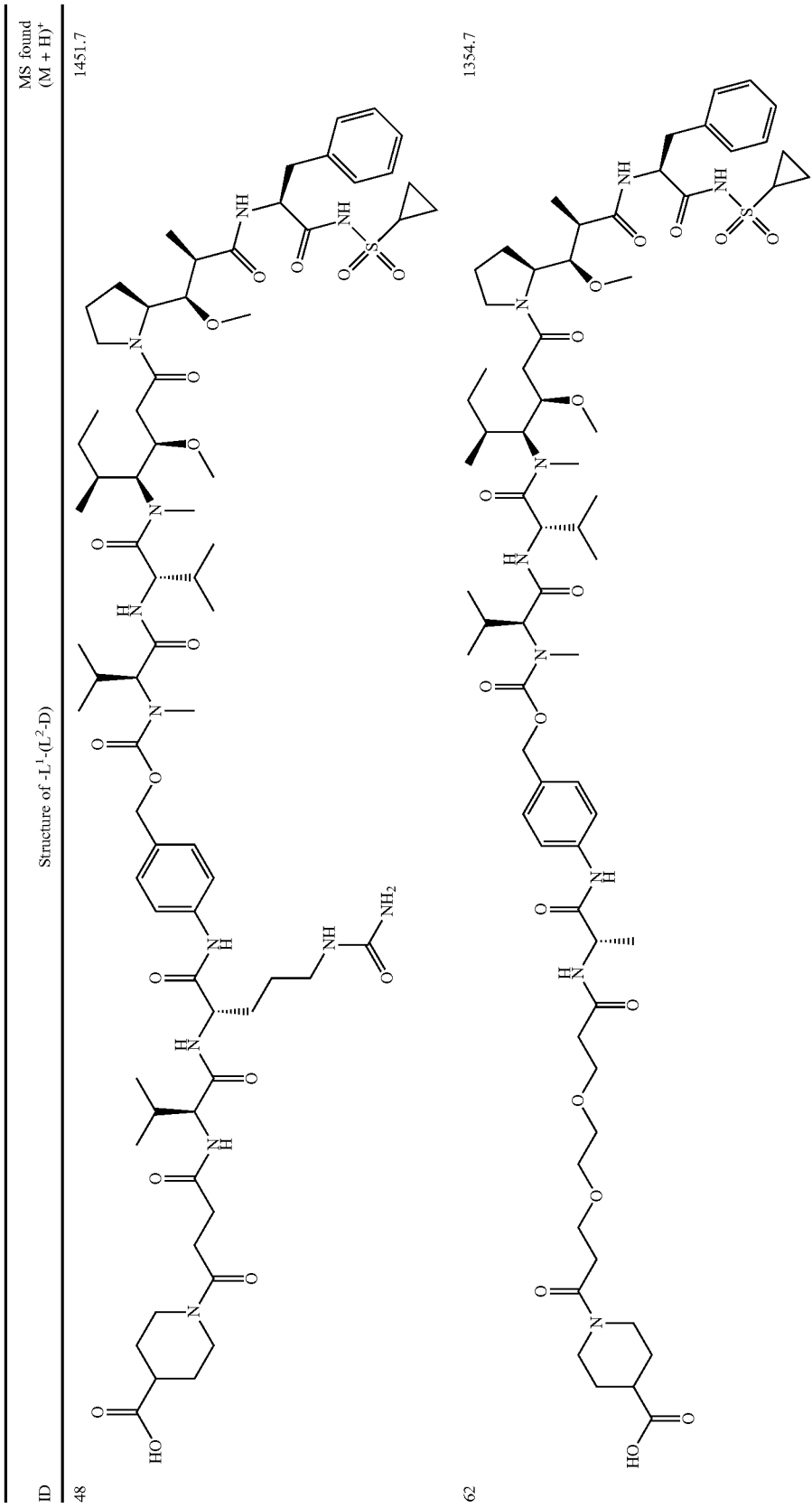

| ID | Structure of -L¹-(L²-D) | MS found (M + H)⁺ |
|---|---|---|
| 49 | | 1106.4 |
| 63 | | 1232.5 |
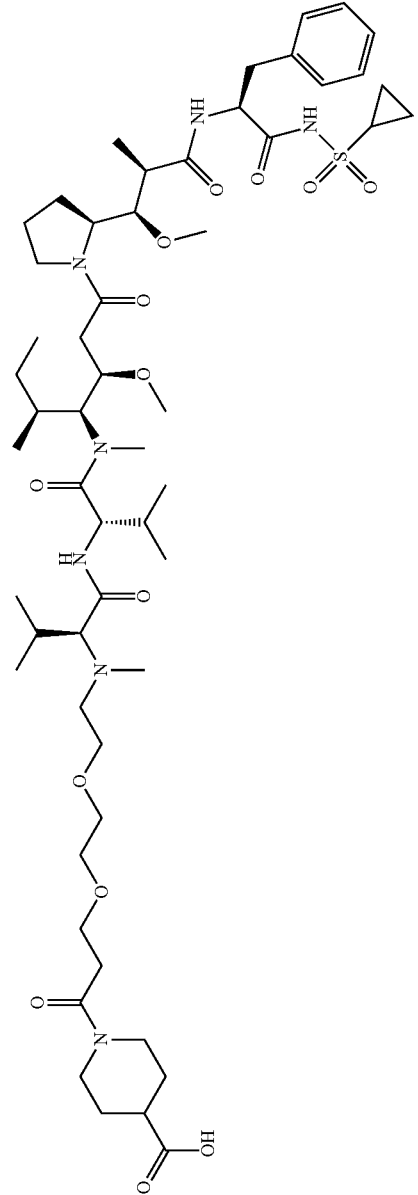

-continued

| ID | Structure of -L¹-(L²-D) | MS found (M + H)⁺ |
|---|---|---|
| 64 | | 1320.4 |
| 65 | | 1598.1 |
| 66 | | 1334.8 |

-continued
| ID | Structure of -L¹-(L²-D) | MS found (M + H)⁺ |
|---|---|---|
| 67 | 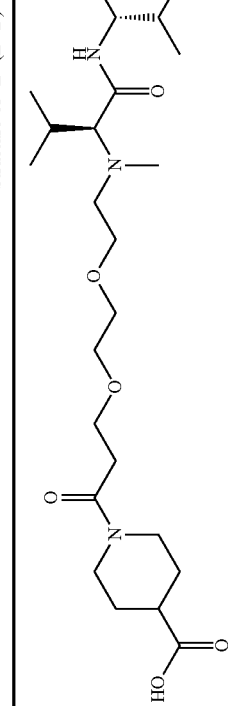 | 1042.5 |
| 55 | 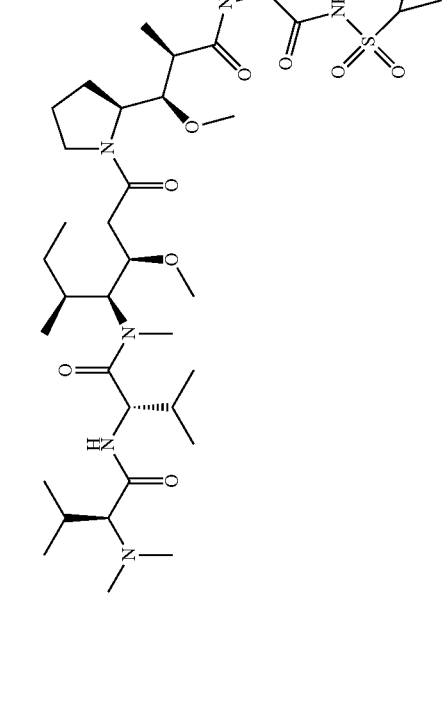 | 1020.8 |

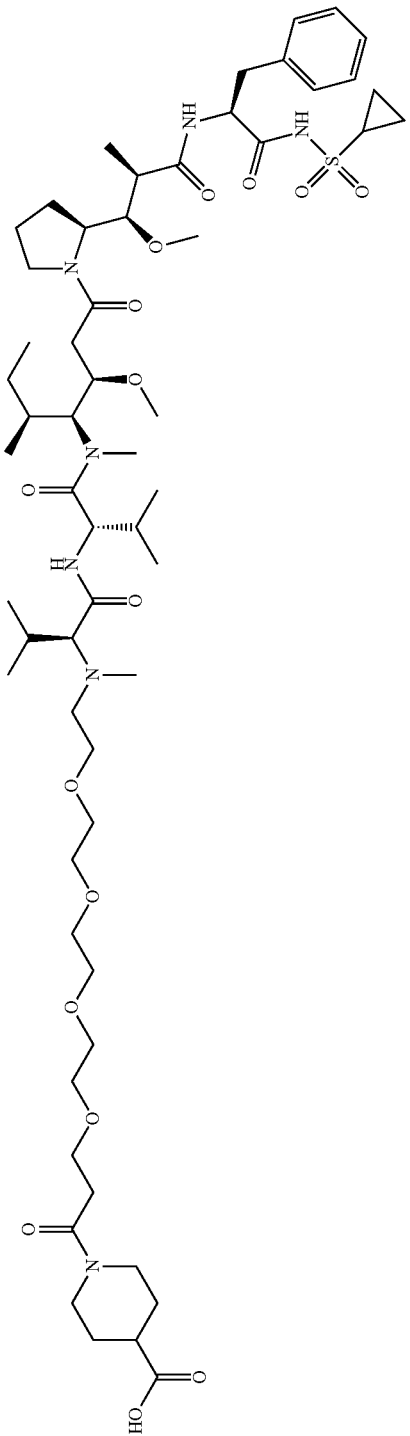

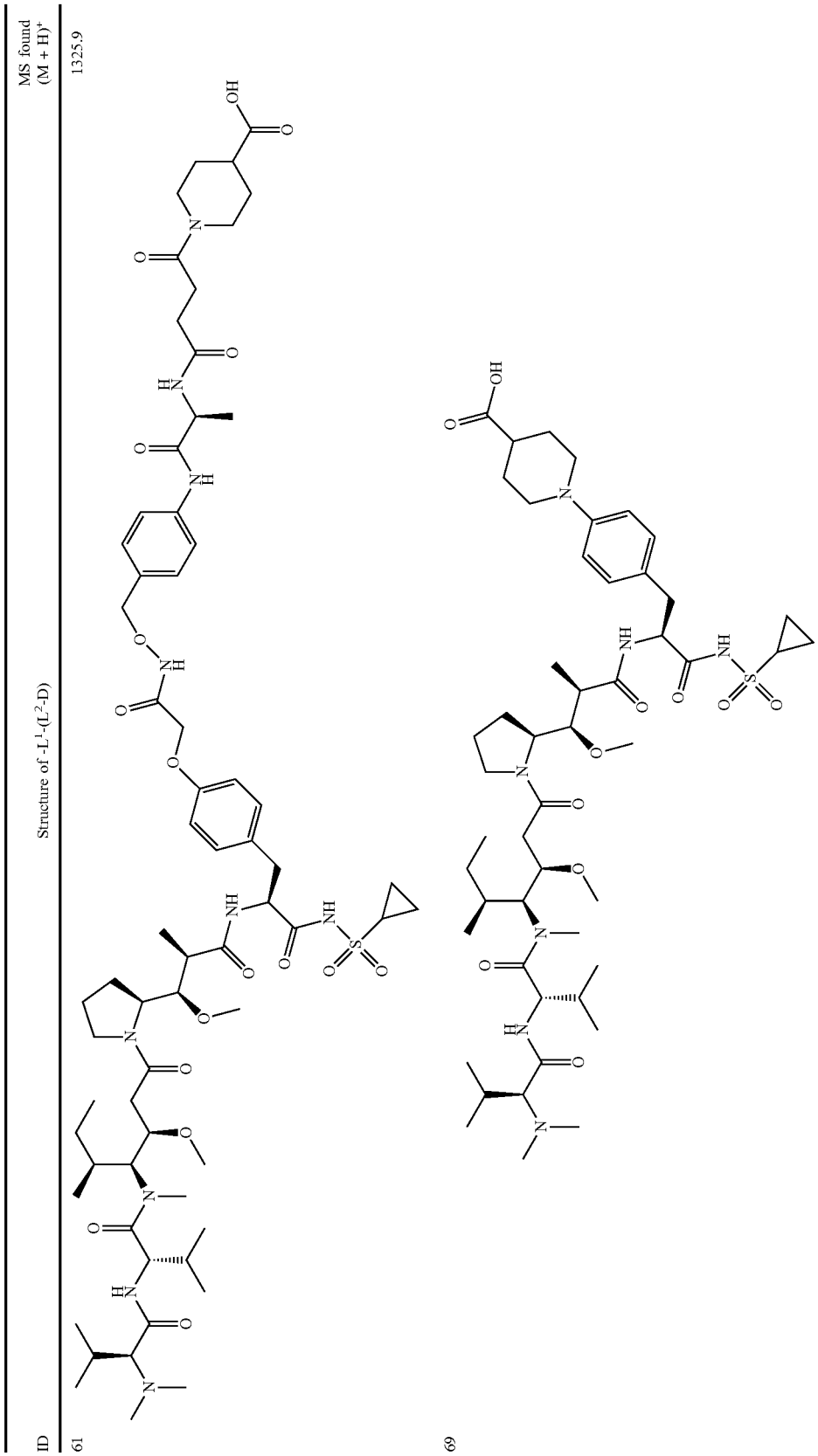

| ID | Structure of -L¹-(L²-D) | MS found (M + H)⁺ |
|---|---|---|
| 70 | | 1133.5 |
| 71 | | 1135.6 |

| ID | Structure of -L¹-(L²-D) | MS found (M + H)⁺ |
|---|---|---|
| 72 | 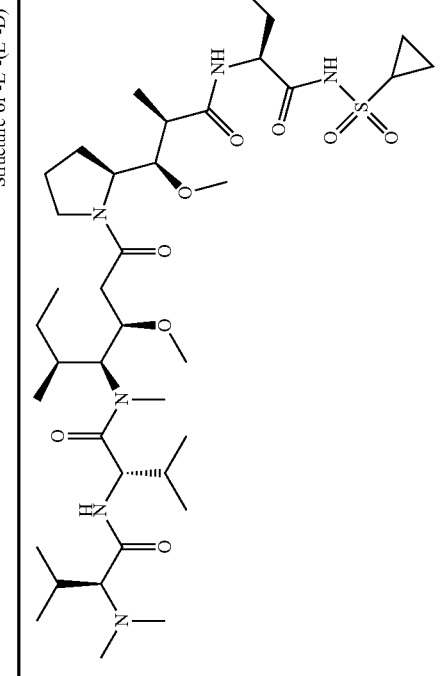 | 1062.9 |
| 73 | 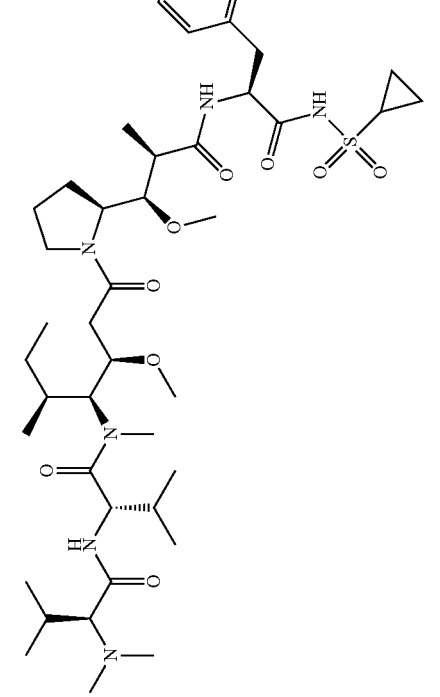 | 1090.2 |

-continued
| ID | Structure of -L¹-(L²-D) | MS found (M + H)⁺ |
|---|---|---|
| 74 | 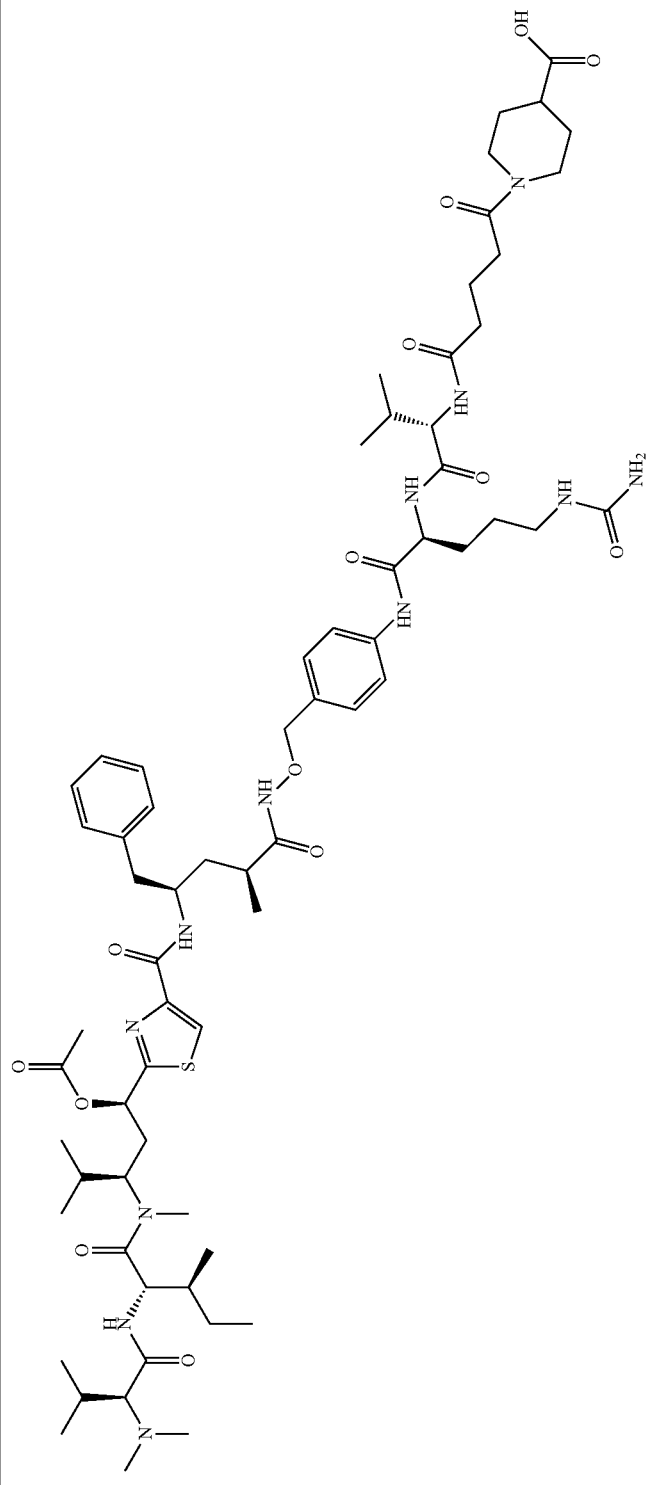 | 1331.6 |

-continued
| ID | Structure of -L¹-(L²-D) | MS found (M + H)+ |
|---|---|---|
| 75 | 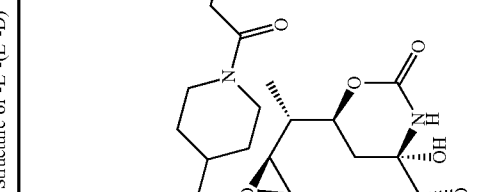 | 901.4 |
| 76 | 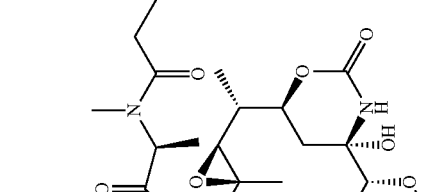 | 875.5 |

| ID | Structure of -L¹-(L²-D) | MS found (M + H)⁺ |
|---|---|---|
| 77 | 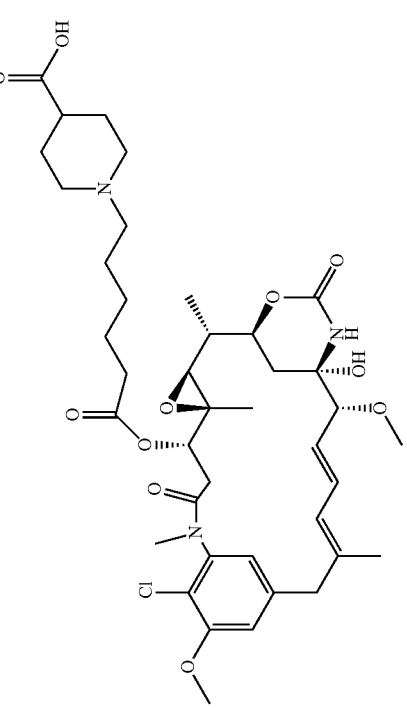 | 790.5 |
| 78 | 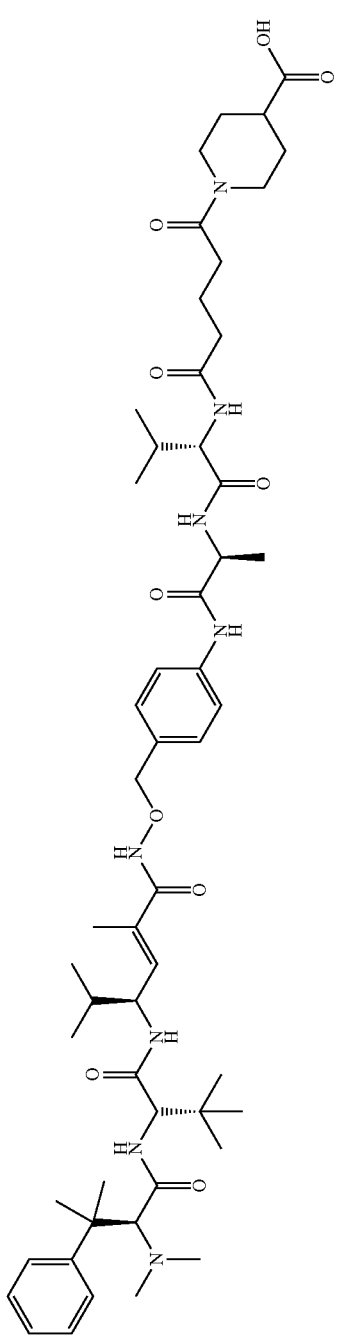 | 989.7 |

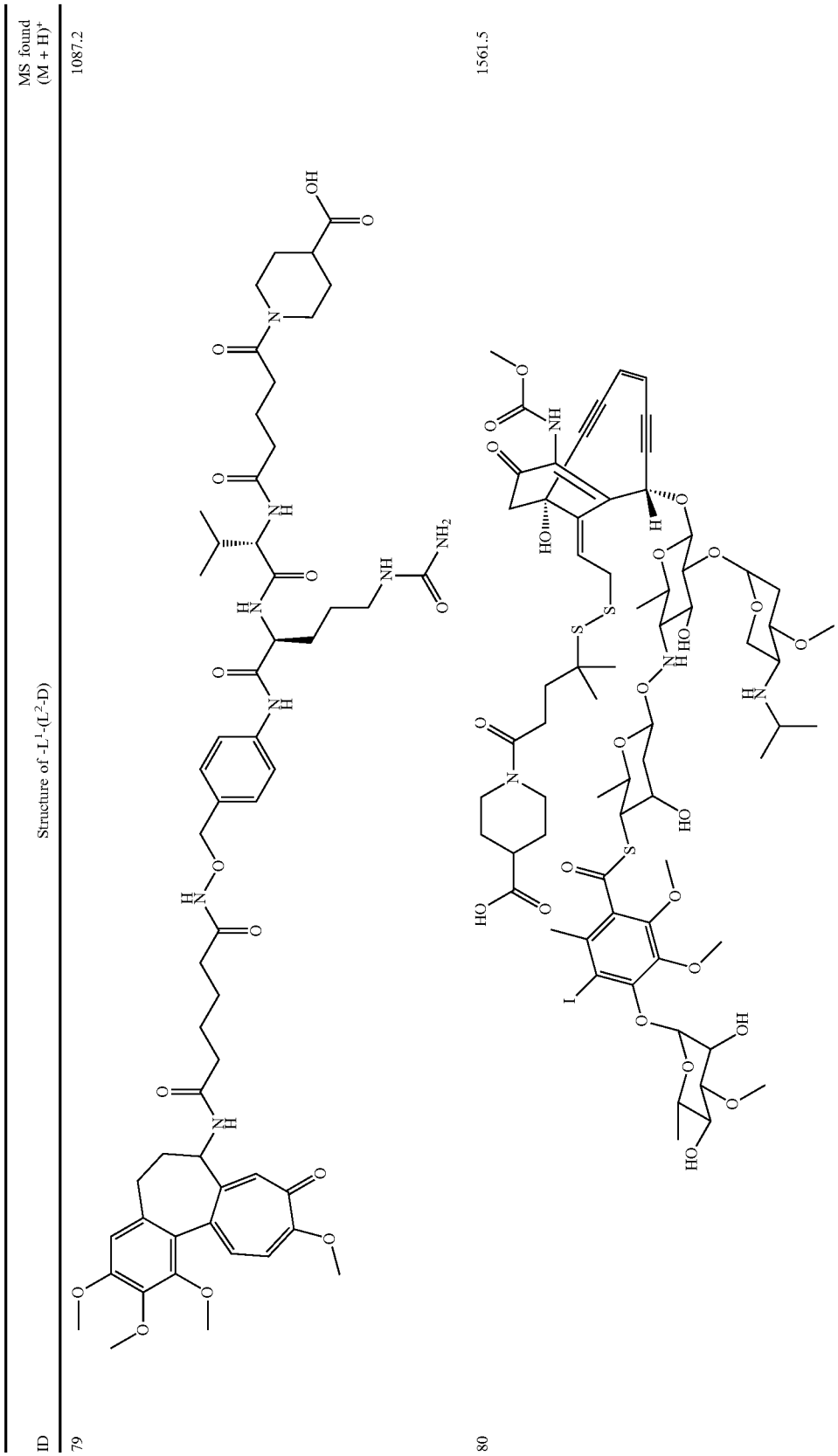

-continued
| ID | Structure of -L¹-(L²-D) | MS found (M + H)⁺ |
|---|---|---|
| 81 | 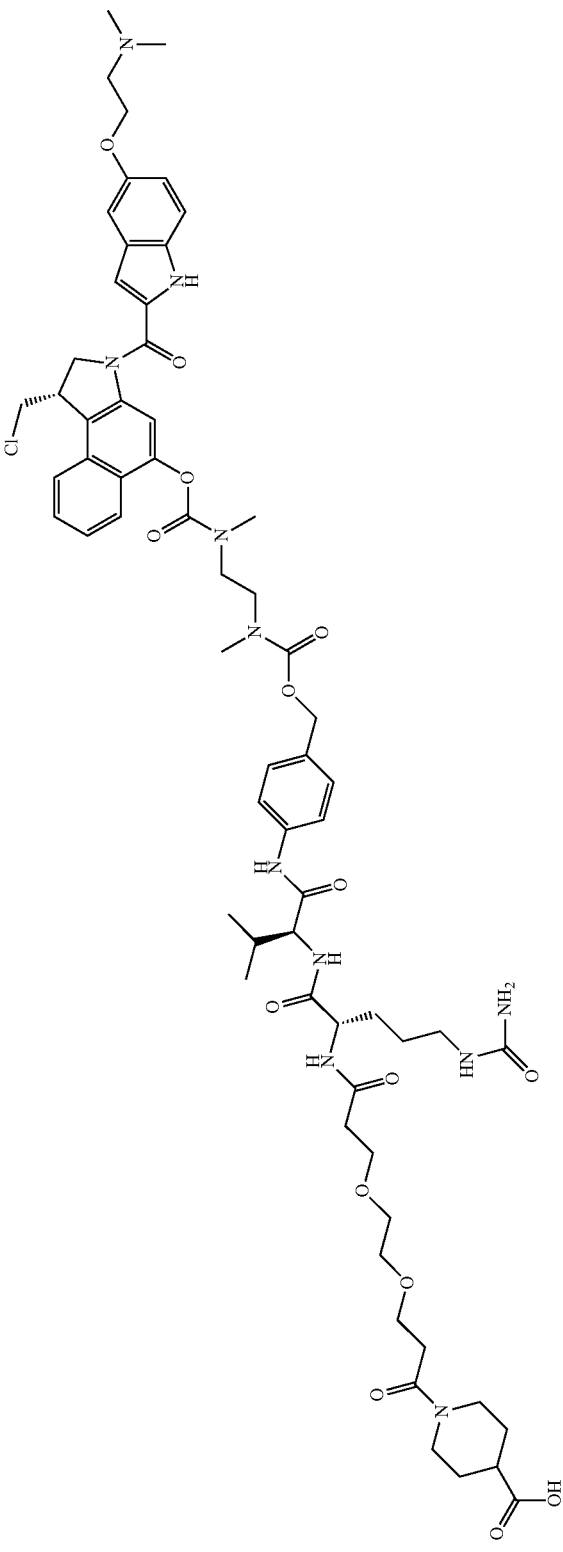 | 1282.4 |

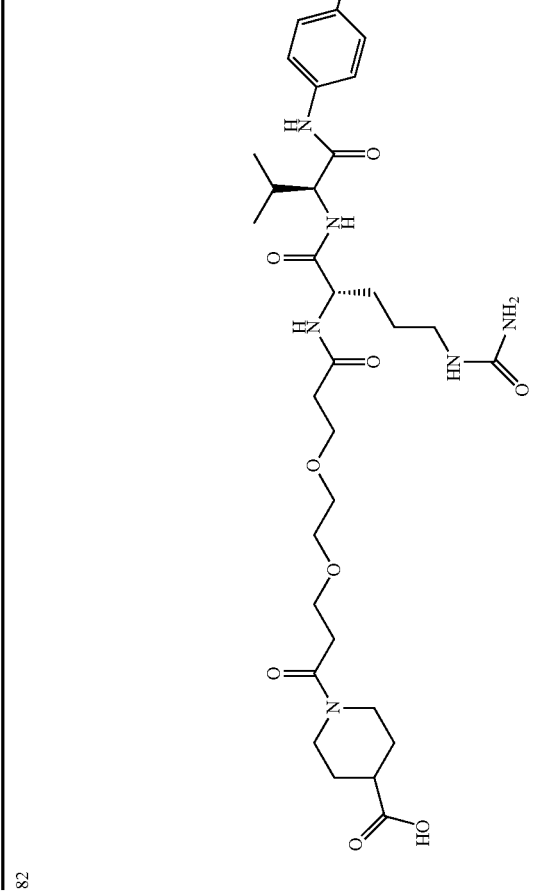

Example V-1. Synthesis of Compound 48
SCHEME IX
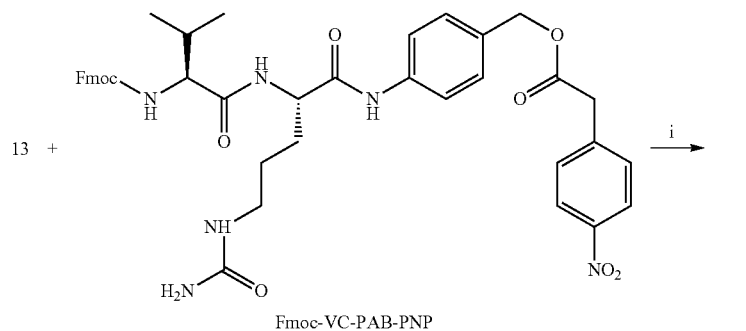
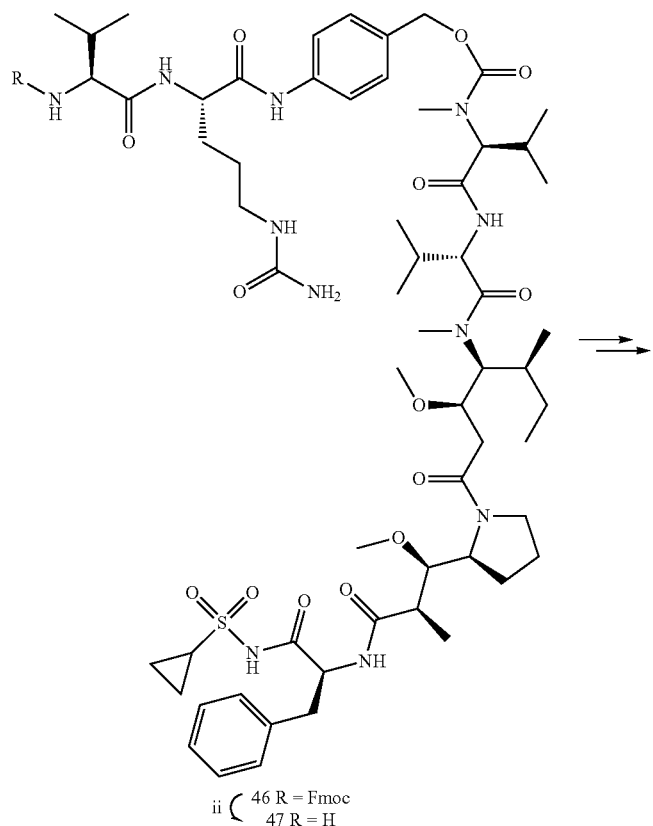

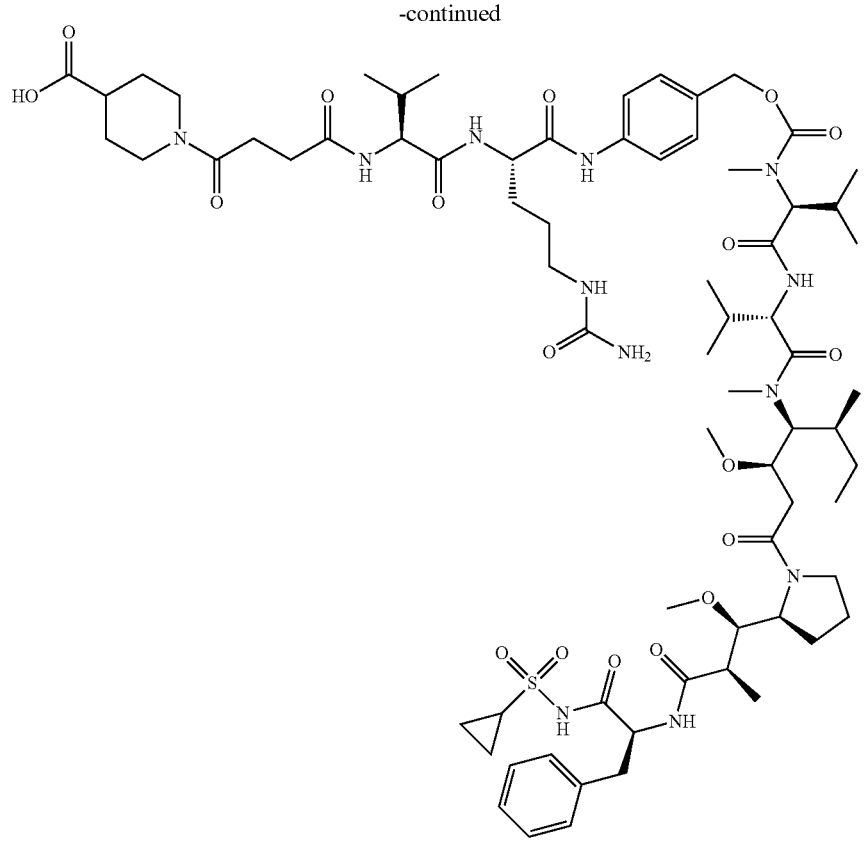

48

Scheme IX. Reagents and conditions: i. DIEA, HOBt (5%), DMF, rt, 48 h; ii. Piperidine, DMF.

Compound 48 was synthesized using the general procedures described above as following: Carbamate formation (General procedure I) between compound 13 and Fmoc-VC-PAB-PNP, followed by removal of Fmoc (General procedure D) to give the intermediate compound 47 which was converted to the final compound using the same procedure described for the synthesis of compound 34. The final compound was purified by reverse phase HPLC to give compound 48 as a white powder after lyophilization. MS m/z Calcd for $C_{71}H_{110}N_{12}O_{18}S$ 1450.8. Found 1451.7 ([M+H]$^+$).

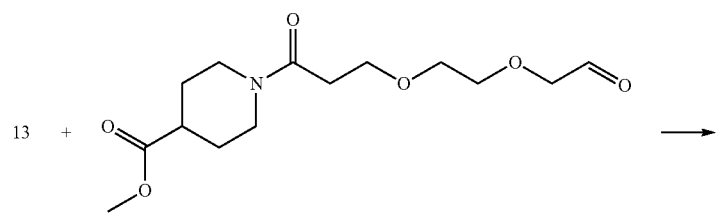

50

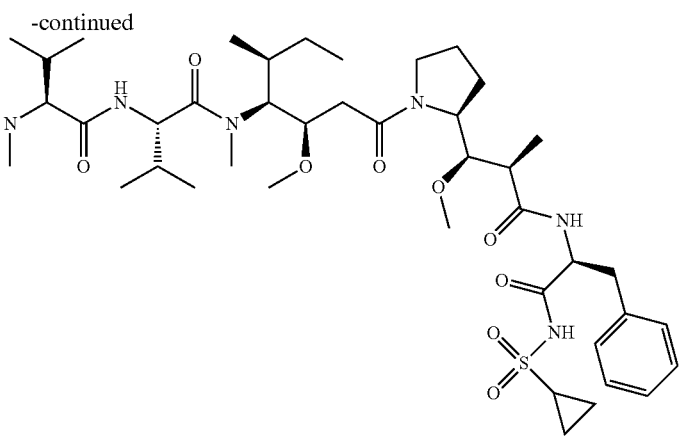

49

Example V-2. Synthesis of Compound 49

Compound 49 was synthesized using the general procedures described above as following: reaction of compound 13 and aldehyde 50 under reductive alkylation conditions (General procedure E) followed by removal of Me ester (General procedure F). The final compound was purified by reverse phase HPLC to give compound 49 as a white powder after lyophilization. MS m/z Calcd for $C_{55}H_{91}N_7O_{14}S$ 1105.6. Found 1106.4 ([M+H]$^+$).

Example V-3. Synthesis of Compound 55

SCHEME V-3

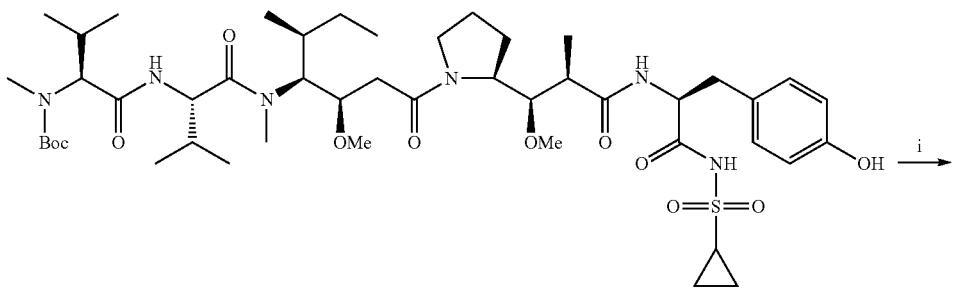

51

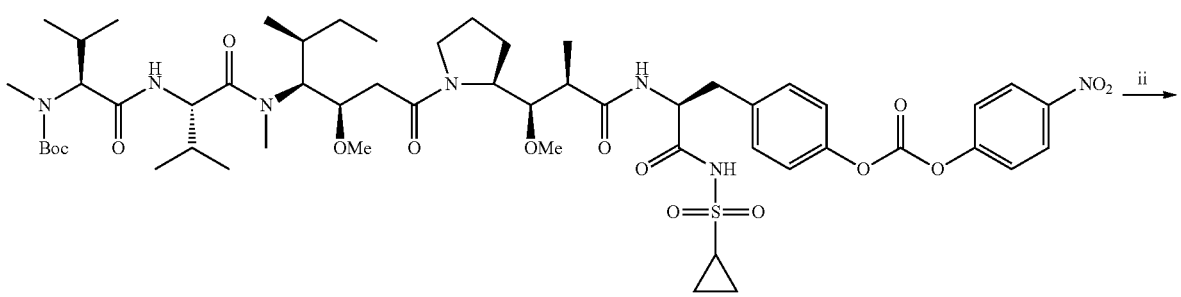

52

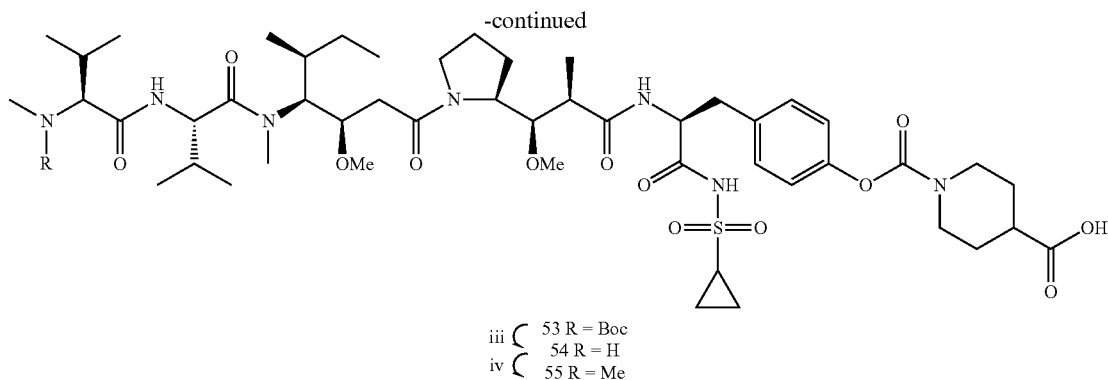

iii ⌐ 53 R = Boc
   ⌐ 54 R = H
iv ⌐ 55 R = Me

Scheme V-3. Reagents and conditions: i. bis(nitrophenyl) carbonate, DIEA, THF/DMF, r.t.; ii. Piperidine 4-carboxylic acid, NaHCO₃ (aq.); iii. HCl/Dixoane (4N); iv. HCHO, NaCNBH₃, DMF, HOAc.

The phenol 51 (1 mmol) was treated with 3 eq of bis(p-nitrophenyl)carbonate to form the activated carbonate 52 (general procedure G). The crude product was used directly without further purification. Piperidine 4-carboxylic acid (5 eq) was dissolved in sat. aq. NaHCO₃ (5 mL) and the solution was added. The reaction mixture was stirred at room temperature for 8 h. Citric acid (aq. 10%) was added to acidify the reaction (pH=4-5) and then diluted with EtOAc (150 mL). Organic Lyser was dried (over Na₂SO₄) and concentrated to give the crude product 53 which underwent the following procedures: removal of Boc (General procedure C), and reductive alkylation using HCHO (General procedure E). The final compound was purified by reverse phase HPLC to give compound 55 as a white powder after lyophilization. MS m/z Calcd for $C_{50}H_{81}N_7O_{13}S$ 1019.6. Found 1020.8 ([M+H]⁺).

Example V-4. Synthesis of Compound 60

SCHEME V-4

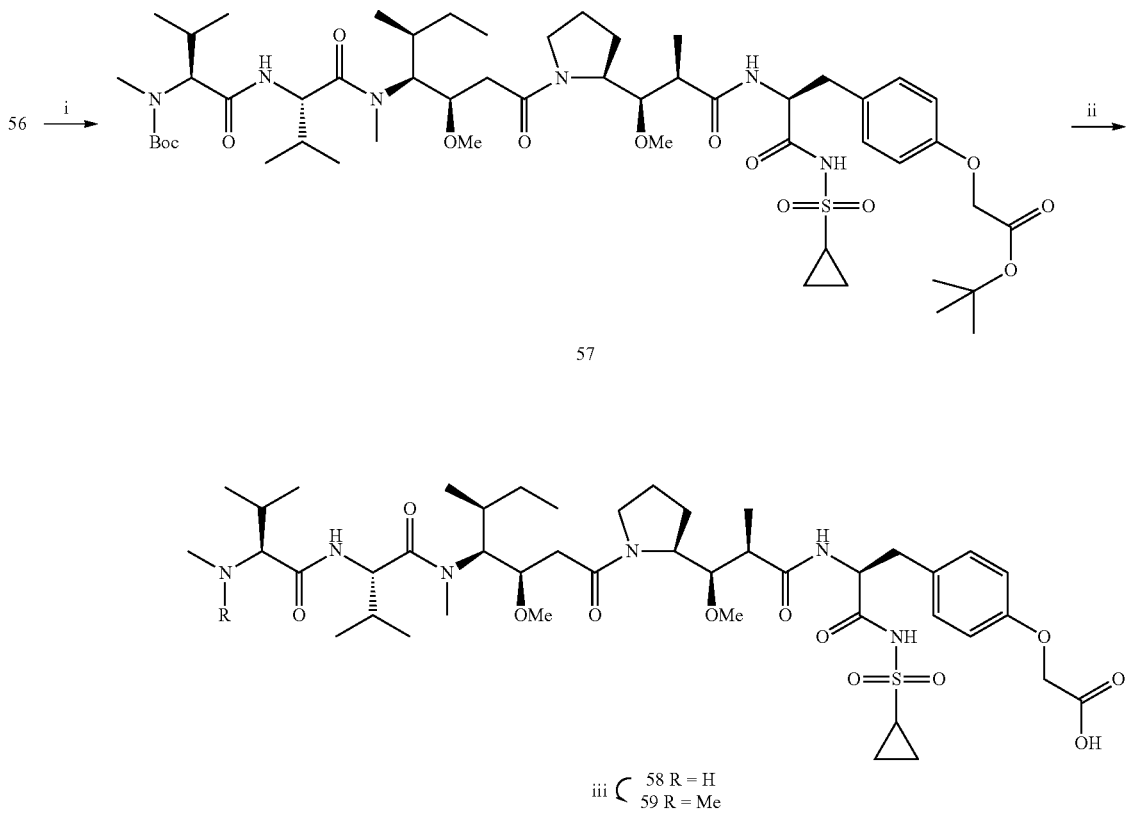

iii ⌐ 58 R = H
    ⌐ 59 R = Me

Scheme V-4. Reagents and conditions: i. t-Butylbromoacetate, K₂CO₃, DMF, rt, 2 h; ii. HCl/dioxane (4N); iii. HCHO, NaCNBH₃, HOAc, DMF To a stirred solution of compound 59 (0.2 mmol, 190 mg) in anhydrous DMF (5 mL) was added t-butyl bromoacetate (0.3 mmol), followed by solid potassium carbonate (55 mg, 0.4 mmol). The reaction mixture was stirred at room temperature for 2 h. LC/MS confirmed that the completion of the reaction. The mixture was diluted with EtOAc (100 mL) and washed with 10% aq. Citric acid and brine. The organic Lyser was dried and concentrated to dryness to give the crude compound 57, which underwent the following procedures: removal of Boc and t-Bu (General procedure C), and reductive alkylation using HCHO (General procedure E). The final compound was purified by reverse phase HPLC to give compound 59 as a white powder after lyophilization. MS m/z Calcd for $C_{45}H_{74}N_6O_{12}S$, 922.5 Found 923.7 ([M+H]$^+$).

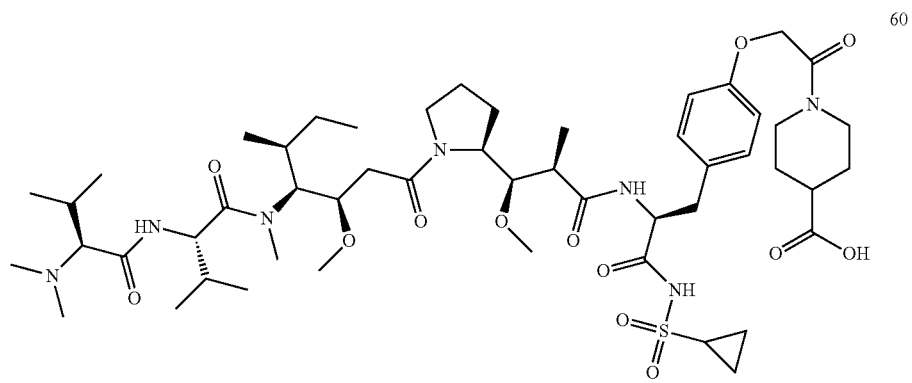 [SMILES: CC[C@H](C)[C@@H]([C@@H](CC(=O)N1CCC[C@H]1[C@H](OC)[C@@H](C)C(=O)N[C@@H](Cc1ccc(OCC(=O)N2CCC(C(=O)O)CC2)cc1)C(=O)NS(=O)(=O)C1CC1)OC)N(C)C(=O)[C@@H](NC(=O)[C@H](C(C)C)N(C)C)C(C)C]

Compound 60 was synthesized using the general procedures described above as following: HATU mediated amide bond formation (General procedure A) between compound 59 and methyl isonipecotate, followed by saponification to remove methyl group from ester (General procedure F). The final compound was purified by reverse phase HPLC to give compound 60 as a white powder after lyophilization. MS m/z Calcd for $C_{51}H_{83}N_7O_{13}S$ 1033.6. Found 1034.7 ([M+H]$^+$).

Example V-5. Synthesis of Compound 61

Compound 61 was synthesized using the general procedures described above as following: DIC/HOAt mediated amide bond formation (General procedure B) between compound 59 and compound 26, followed by removal of Fmoc (General procedure D), HATU mediated amidation reaction with acid 62 (General procedure A), and saponification to remove methyl group from ester (General procedure F). The final compound was purified by reverse phase HPLC to give compound 61 as a white powder after lyophilization. MS m/z Calcd for $C_{65}H_{100}N_{10}O_{17}S$ 1324.7. Found 1325.9 ([M+H]$^+$).

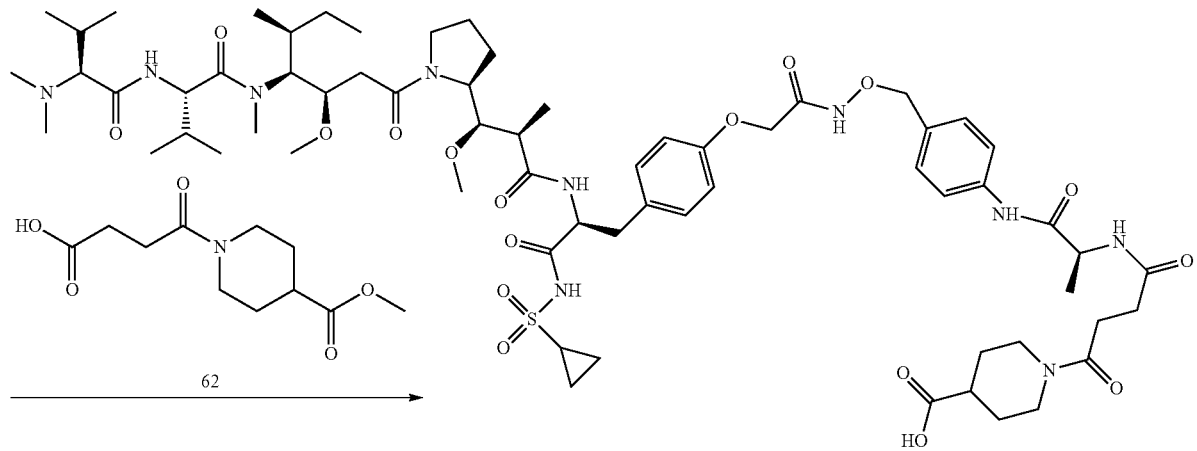

Example VI. Introduction of the Final Function Group Prior to Conjugation
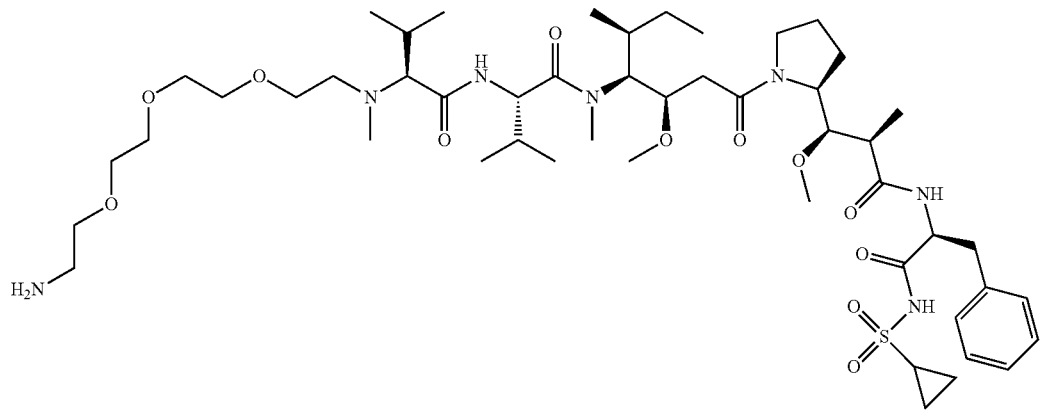
83
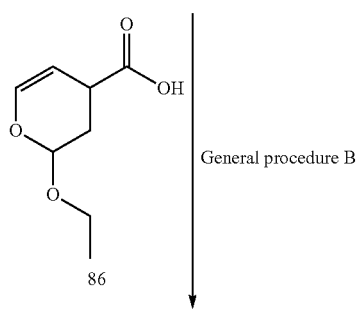
86
General procedure B
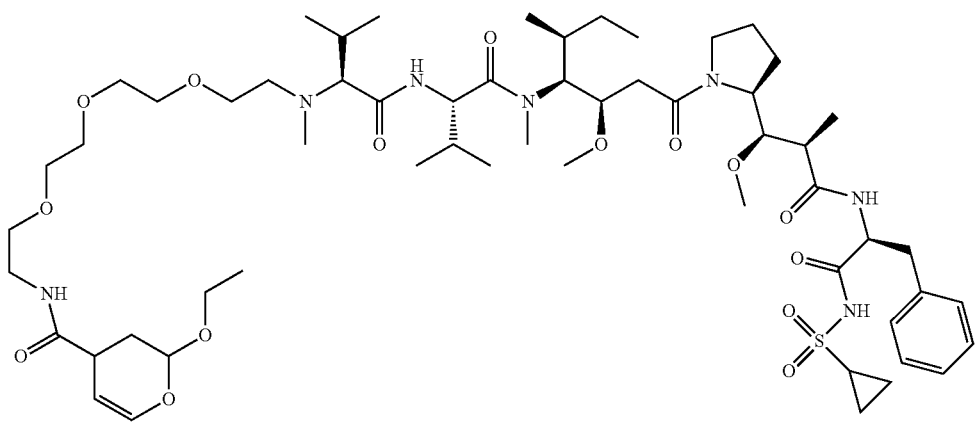
84
1M HCl -continued

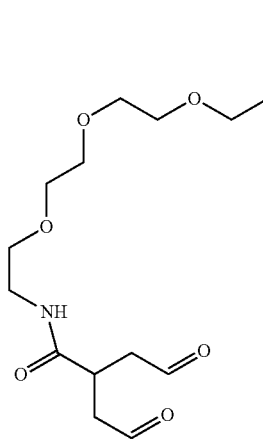

85

Compound 85 was synthesized using the general procedures described above as following: DIC/HOAt mediated amide bond formation (General procedure B) between compound 83 and acid 86. The intermediate 84 was purified by RP-HPLC and the obtained pure product was treated with 1N aq. HCl (20 eq) in acetonitrile/water (6/4, v/v) for 1 h. The crude was used directly without further purification. MS found: 1136.6 (M+H)+.

Antibody-Drug Conjugation

General Conjugation Procedure II:

To a solution of 0.5-50 mgs/mL of targeting molecule A in buffer at pH 6.0-9.0 with 0-30% organic solvent, was added 0.1-10 eq of activated carboxylic component in a manner of portion wise or continuous flow. The reaction was performed at 0-40° C. for 0.5-50 hours with gentle stirring or shaking, monitored by HIC-HPLC. The resultant crude ADC product underwent necessary down-stream steps of desalt, buffet changes/formulation, and optionally, purification, using the state-of-art procedures. The final ADC product was characterized by HIC-HPLC, SEC, RP-HPLC, and optionally LC-MS. The average DAR was calculated by UV absorption and/or MS spectroscopy.

Trastuzumab and emtansine were conjugated using a conventional two-step method under conditions provided in U.S. Pat. No. 8,435,528 and references cited therein.

The product of the trastuzumab-emtansine two-step conjugation reaction was analyzed using HIC-HPLC under conditions: HPLC Column: Tosoh TSKgel Butyl-NPR, 4.6 mm×3.5 cm, 2.5 mm; Buffer A: 20 mM sodium phosphate, 1.5 M Ammonium Sulfate, pH 7.0; Buffer B: 20 mM sodium phosphate, 25% v/v isopronal, pH 7.0; flow rate: 1 ml/min; Gradient: 10 min 10% Buffer B to 80% Buffer B, 4 min 100% Buffer B; 20 μl sample.

FIG. 1 shows the HIC-HPLC chromatogram product of the trastuzumab-emtansine two-step conjugation reaction, where DAR represents the number of drugs conjugated per antibody, based on $UV_{252}$ and $UV_{280}$. The amount of unconjugated antibody (DAR=0) is about 1%.

Figure 2:
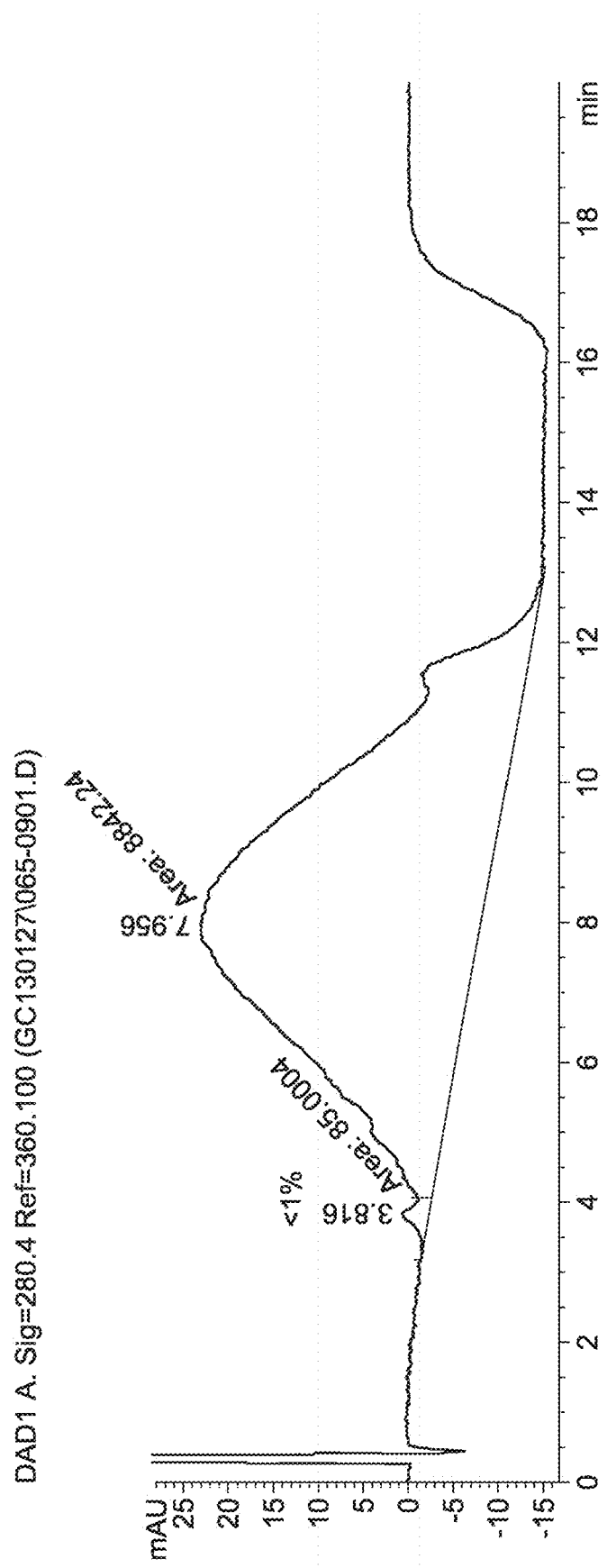
FIG. 2 shows the HIC-HPLC chromatogram product of a conventional trastuzumab-emtansine one-step conjugation reaction.

Trastuzumab and emtansine were conjugated using a conventional one-step method under conditions provided in U.S. Pat. No. 8,435,528 and references cited therein. The product of the trastuzumab-emtansine one-step conjugation reaction was analyzed using HIC-HPLC, as depicted in FIG. 2. The amount of unconjugated antibody (DAR=0) is about 1%.

Figure 3:
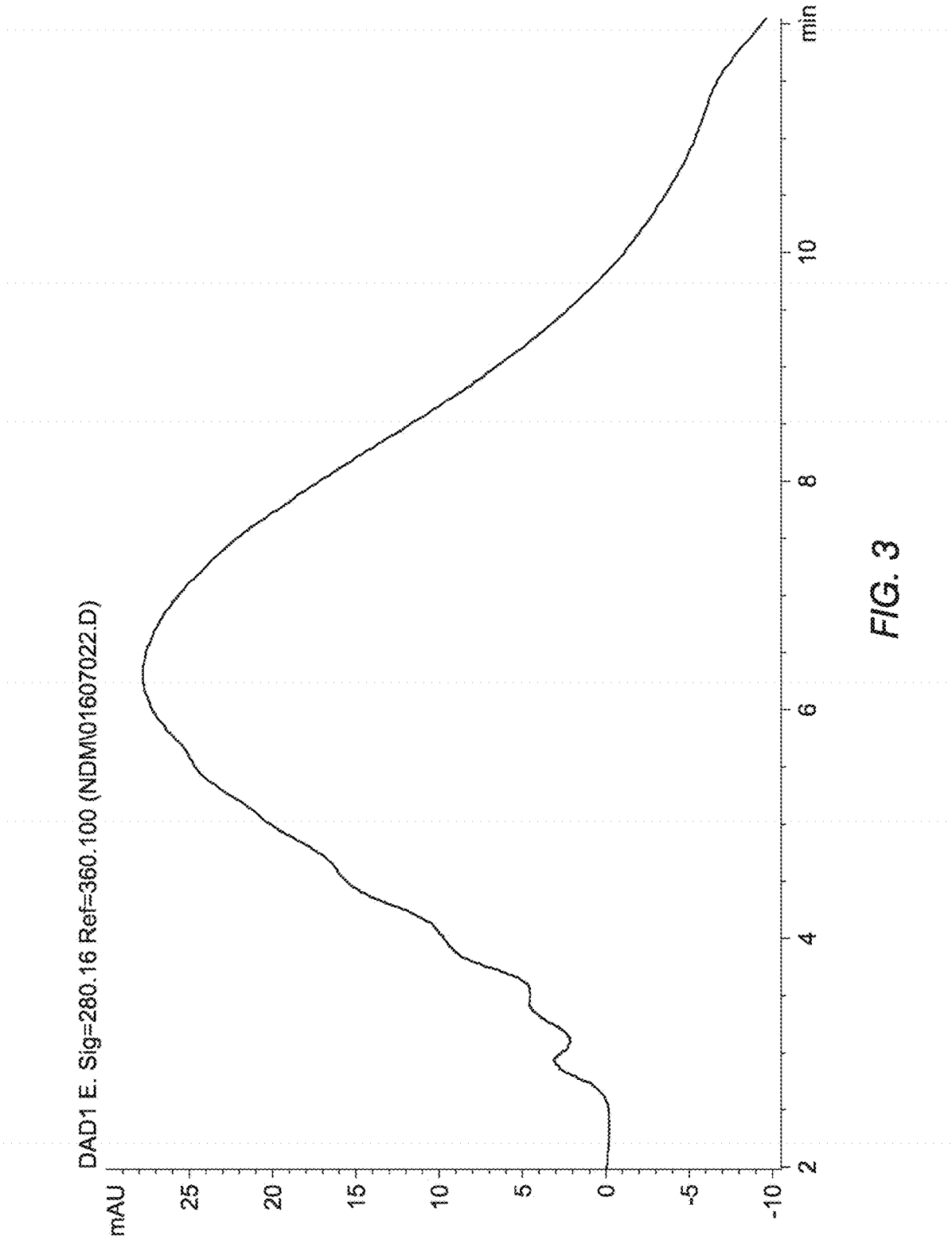
FIG. 3 shows the HIC-HPLC chromatogram product of reacting trastuzumab and compound 34 using a conventional NHS method.

Trastuzumab and compound 34 were conjugated using a conventional NHS method under conditions provided in U.S. Pat. No. 8,435,528 and references cited therein. The product of the trastuzumab-compound 34 NHS conjugation reaction was analyzed using HIC-HPLC, as depicted in FIG. 3.

Figure 4:
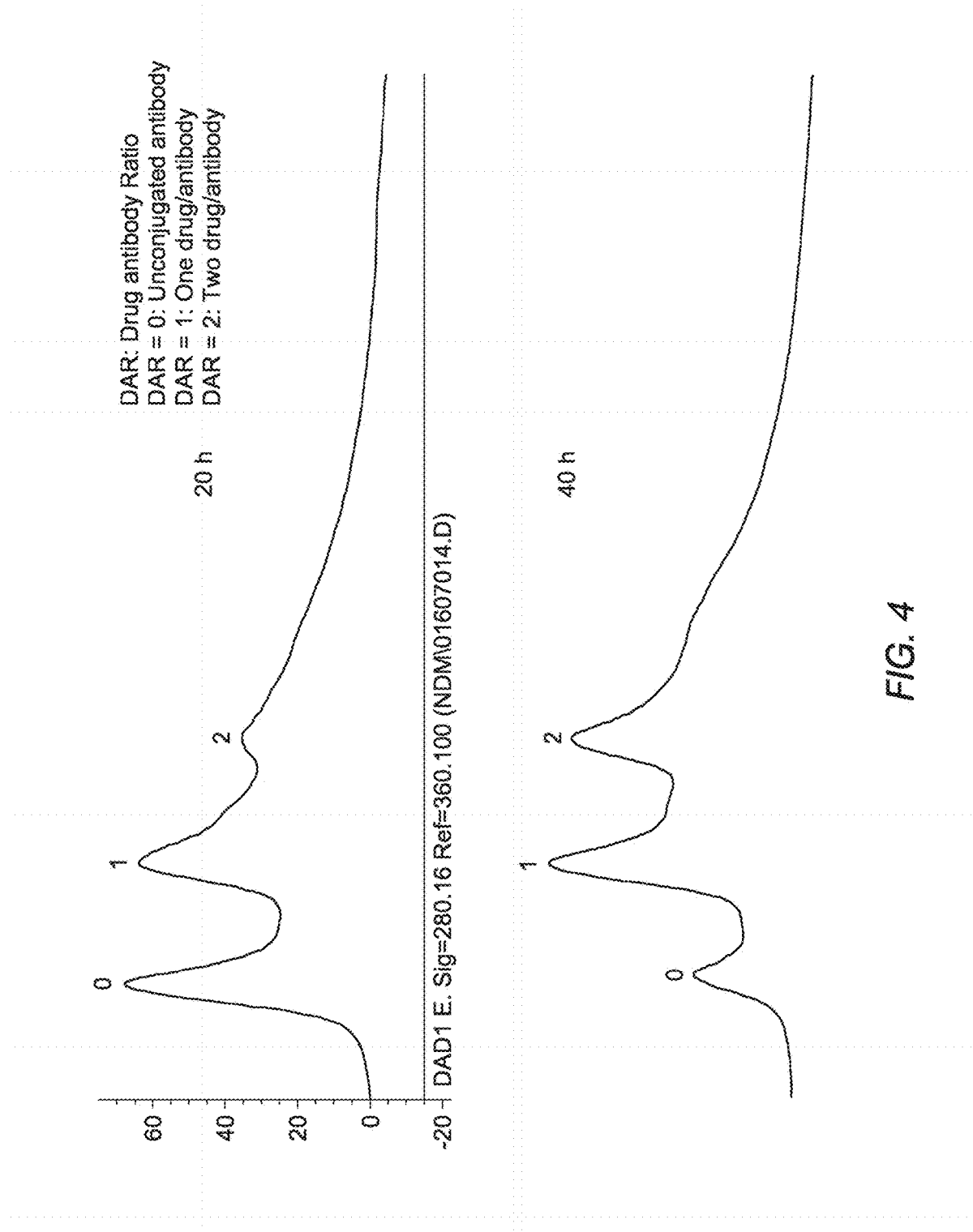
FIG. 4 shows the HIC-HPLC chromatogram product of reacting trastuzumab and compound 34 using a selective conjugation method.

Trastuzumab and compound 34 were conjugated using a selective conjugation method under General Conjugation Procedure II. Samples were removed after reaction for 20 hours and for 40 hours. The product of the trastuzumab-compound 34 selective conjugation reaction was analyzed using HIC-HPLC, as depicted in FIG. 4. The number of drugs conjugated per antibody (DAR) were primarily 0, 1 and 2, as depicted in FIG. 4.

Figure 5:
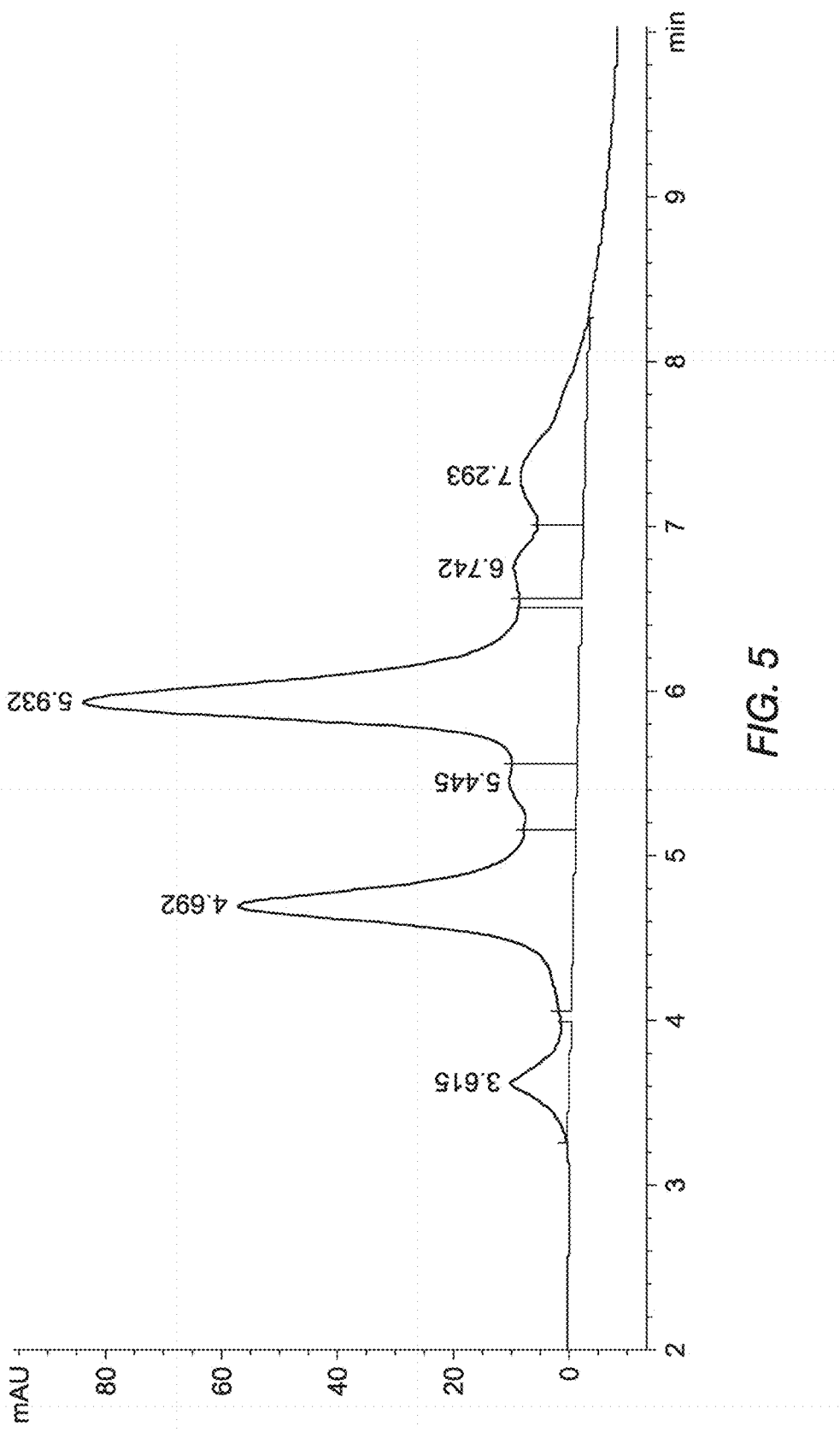
FIG. 5 shows the HIC-HPLC chromatogram product of reacting trastuzumab and compound 67 using a selective conjugation method.

Trastuzumab and compound 67 were conjugated using a selective conjugation method under the General Conjugation Procedure II. The product of the trastuzumab-compound 67 selective conjugation reaction was analyzed using HIC-HPLC, as depicted in FIG. 5.

Figure 6:
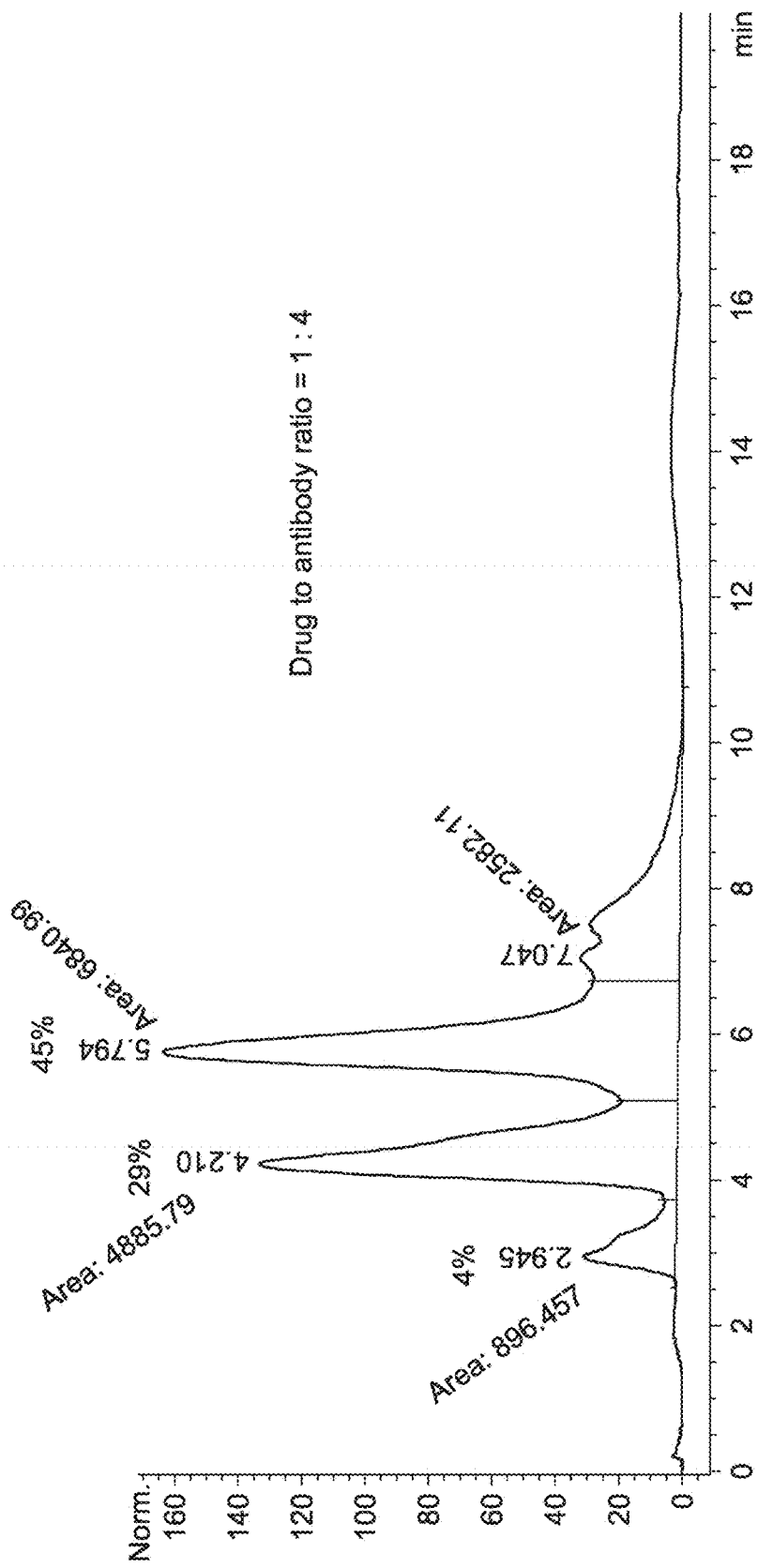
FIG. 6 shows the HIC-HPLC chromatogram product of reacting trastuzumab and compound 62 using a selective conjugation method at a drug/antibody ratio of 1:4.

Trastuzumab and compound 62 were conjugated using a selective conjugation method under the General Conjugation Procedure II, where the ratio of compound 62 to trastuzumab used in the conjugation reaction was 1:4. The product of the trastuzumab-compound 62 selective conjugation reaction was analyzed using HIC-HPLC, as depicted in FIG. 6. The number of drugs conjugated per antibody (DAR) for DAR 0, 1, and 2 were 0 (4%), 1 (29%) and 2 (45%), as depicted in FIG. 6.

Figure 7:
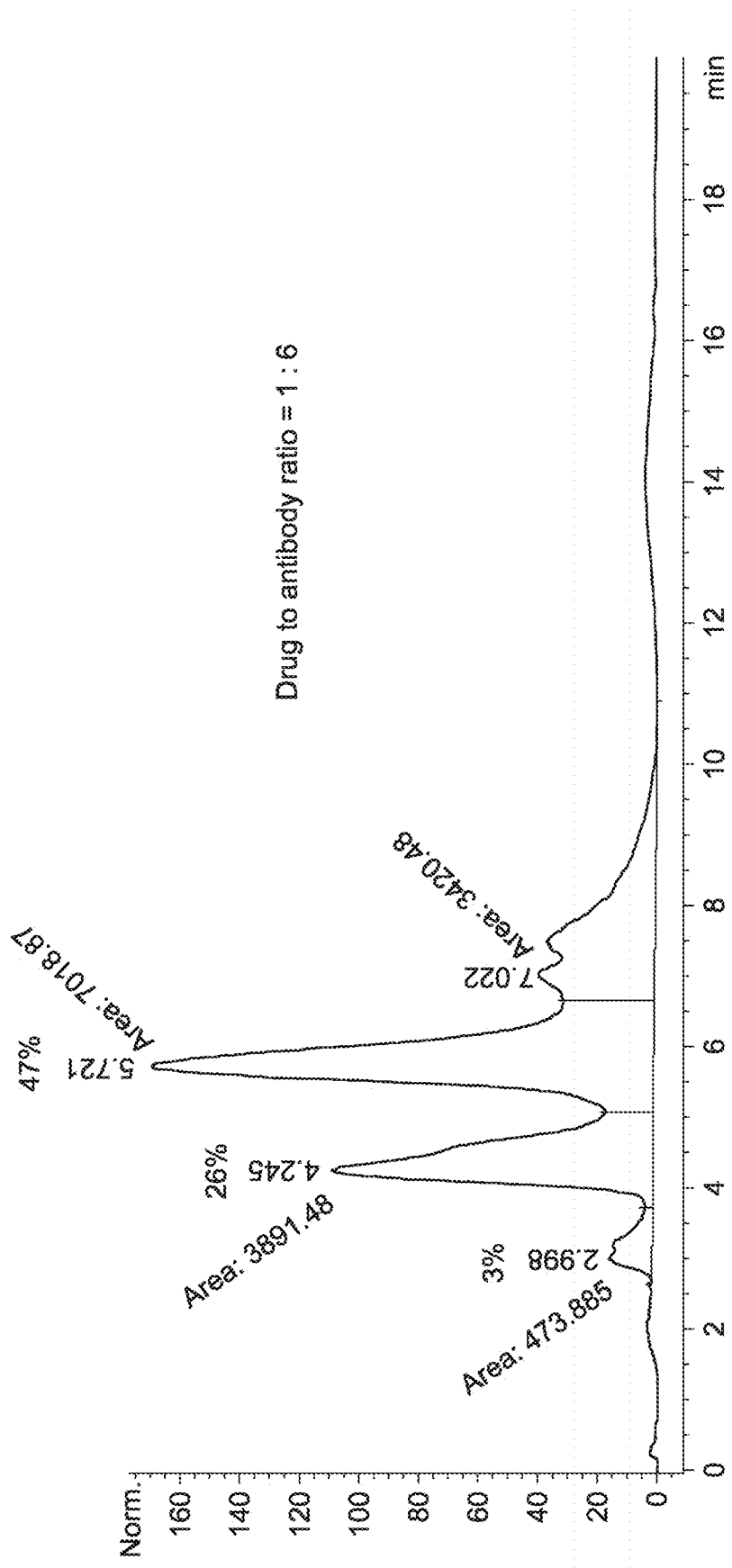
FIG. 7 shows the HIC-HPLC chromatogram product of reacting trastuzumab and compound 62 using a selective conjugation method at a drug/antibody ratio of 1:6.

Trastuzumab and compound 62 were conjugated using a selective conjugation method under the General Conjugation Procedure II, where the ratio of compound 62 to trastuzumab used in the conjugation reaction was 1:6. The product of the trastuzumab-compound 62 selective conjugation reaction was analyzed using HIC-HPLC, as depicted in FIG. 7. The number of drugs conjugated per antibody (DAR) for DAR 0, 1, and 2 were 0 (3%), 1 (26%) and 2 (47%), as depicted in FIG. 7.

Figure 8:
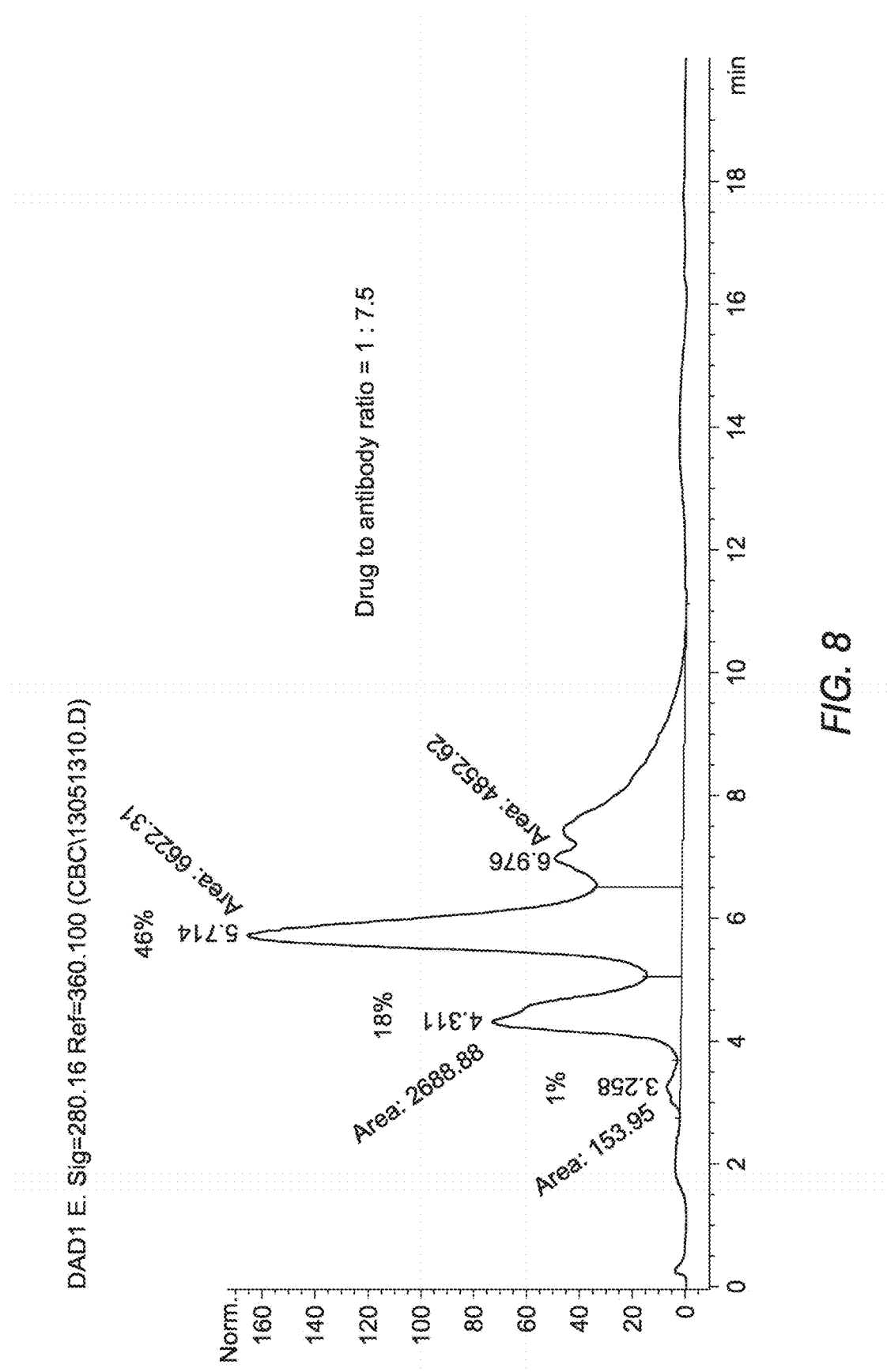
FIG. 8 shows the HIC-HPLC chromatogram product of reacting trastuzumab and compound 62 using a selective conjugation method at a drug/antibody ratio of 1:7.5.

Trastuzumab and compound 62 were conjugated using a selective conjugation method under the General Conjugation Procedure II, where the ratio of compound 62 to trastuzumab used in the conjugation reaction was 1:7.5. The product of the trastuzumab-compound 62 selective conjugation reaction was analyzed using HIC-HPLC, as depicted in FIG. 8. The number of drugs conjugated per antibody (DAR) for DAR 0, 1, and 2 were 0 (1%), 1 (18%) and 2 (46%), as depicted in FIG. 8.

Figure 9:
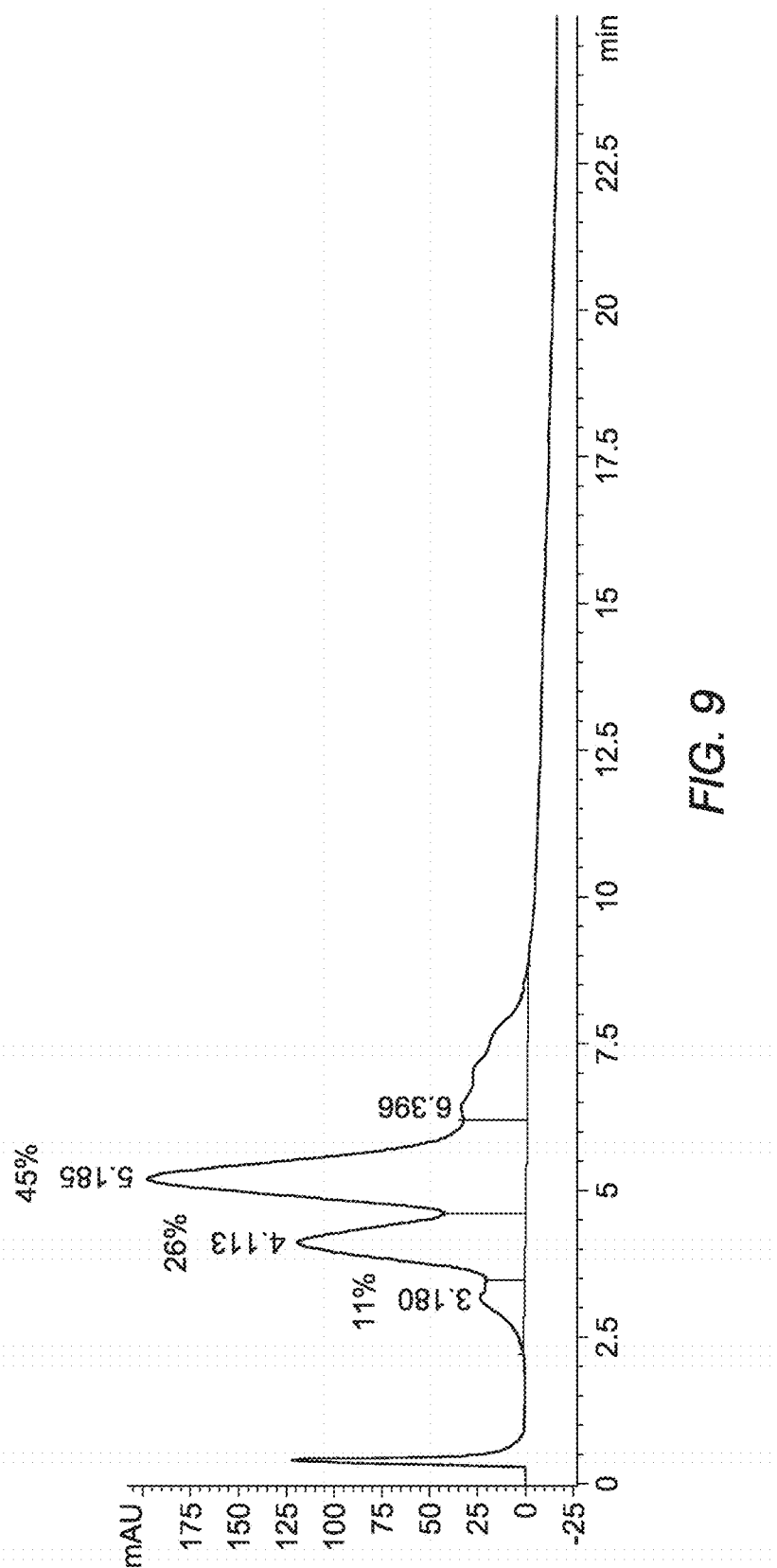
FIG. 9 shows the HIC-HPLC chromatogram product of reacting trastuzumab and compound 49 using a selective conjugation method.

Trastuzumab and compound 49 were conjugated using a selective conjugation method under the General Conjugation Procedure II. The product of the trastuzumab-compound 49 selective conjugation reaction was analyzed using HIC-HPLC, as depicted in FIG. 9. The number of drugs conjugated per antibody (DAR) for DAR 0, 1, and 2 were 0 (11%), 1 (26%) and 2 (45%), as depicted in FIG. 9.

Figure 10:
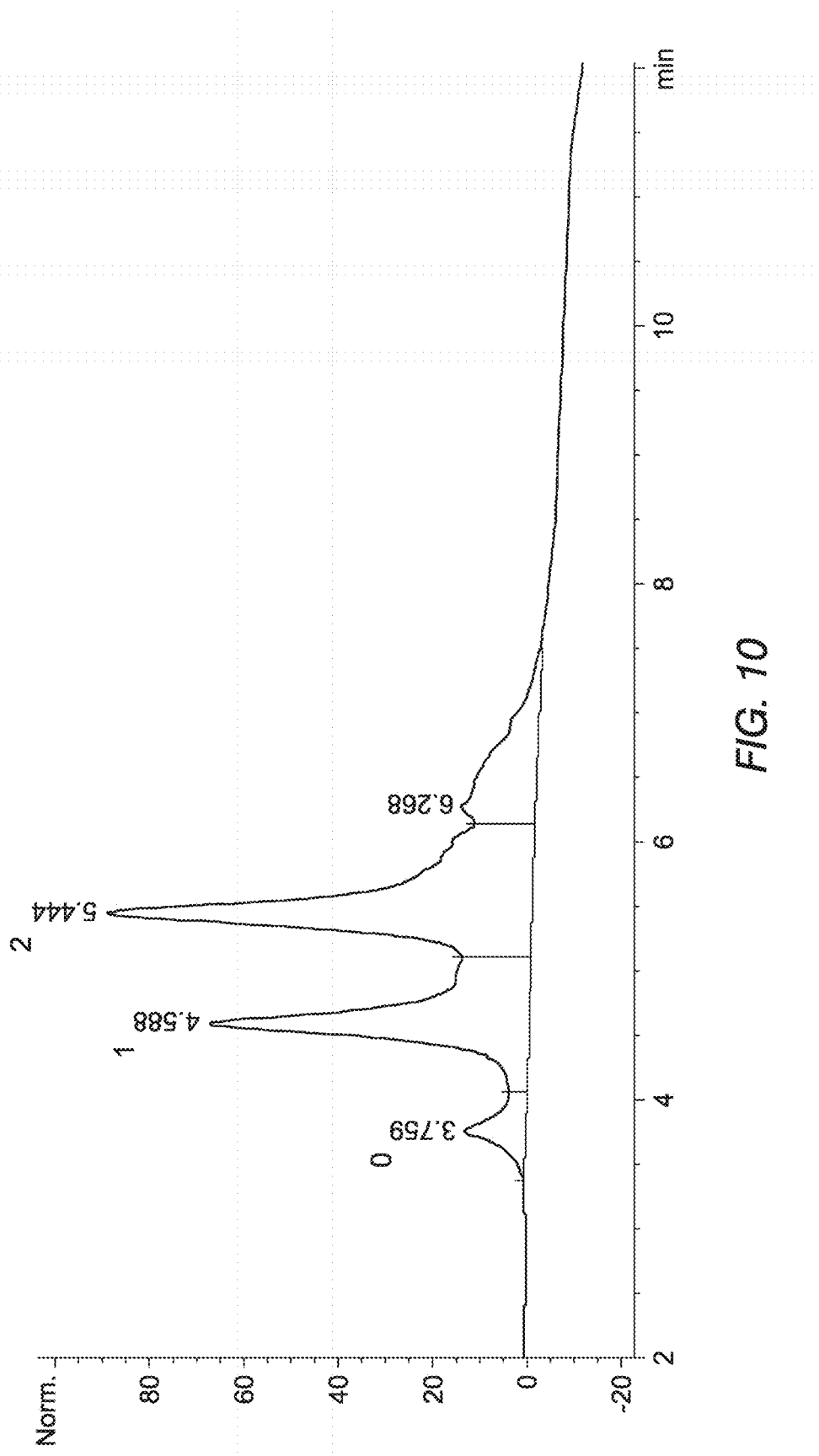
FIG. 10 shows the HIC-HPLC chromatogram product of reacting trastuzumab and compound 73 using a selective conjugation method.

Trastuzumab and compound 73 were conjugated using a selective conjugation method under the General Conjugation Procedure II. The product of the trastuzumab-compound 73 selective conjugation reaction was analyzed using HIC-HPLC, as depicted in FIG. 10. The number of drugs conjugated per antibody (DAR) for DAR 0, 1, and 2 are depicted in FIG. 10.

Figure 11:
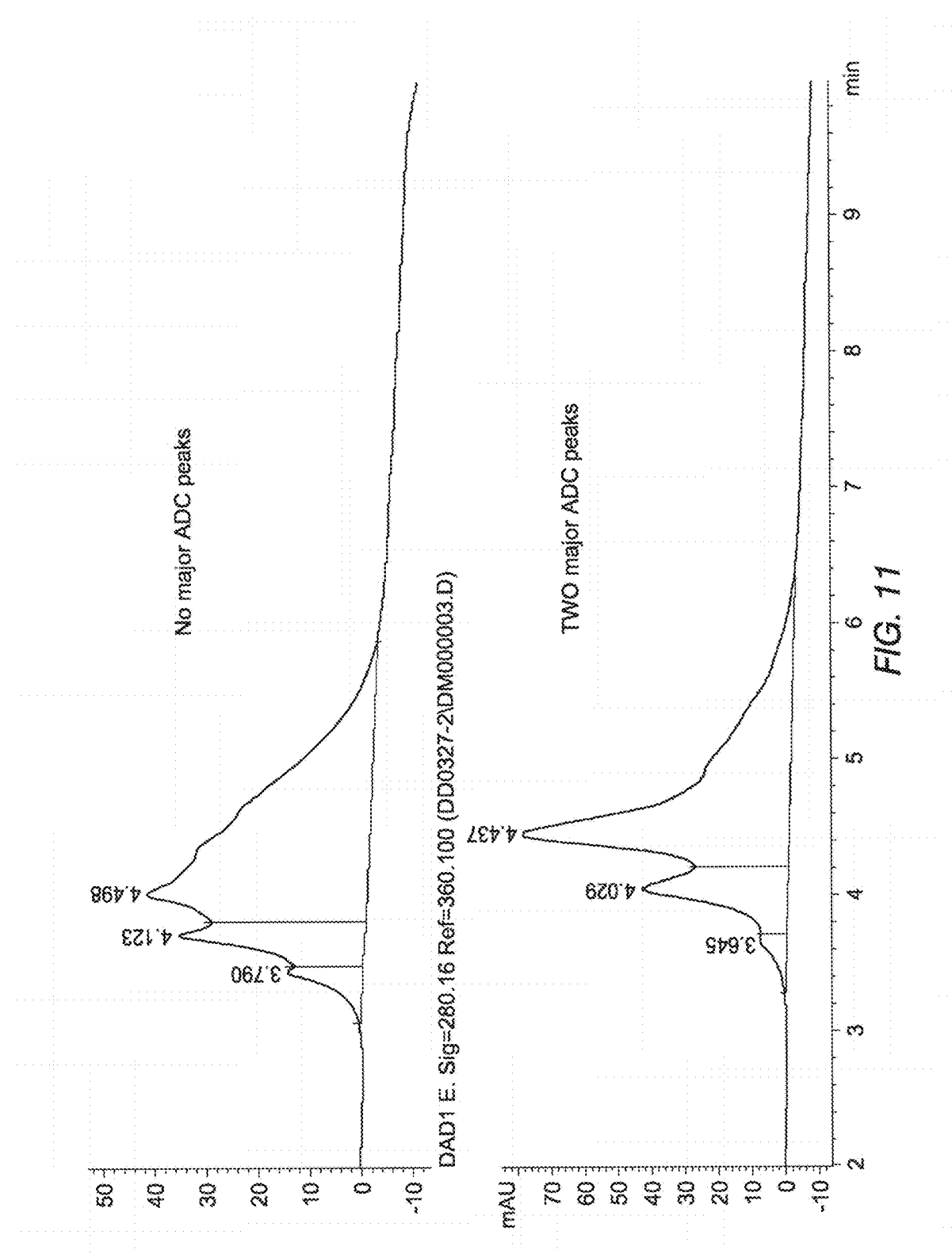
FIG. 11 shows a HIC-HPLC chromatogram product of reacting trastuzumab and compound 60 using a non-selective linker and a HIC-HPLC chromatogram product of reacting trastuzumab and compound 60 using an optimized linker.

Trastuzumab and compound 60 were conjugated using a conventional NHS method. The product of the trastuzumab-compound 60 conjugated with the non-selective linker was analyzed using HIC-HPLC, as depicted in FIG. 11. As seen in FIG. 11, no major ADC peaks were observed when using the non-selective linker.

Trastuzumab and compound 60 were conjugated using the selective conjugation method under the General Conjugation Procedure II. The product of the trastuzumab-compound 60 conjugated with the optimized linker was analyzed using HIC-HPLC, as depicted in FIG. 11. As seen in FIG. 11, two major ADC peaks were observed when using the optimized linker.

In Vitro Cytotoxicity Experiment

Figure 12:
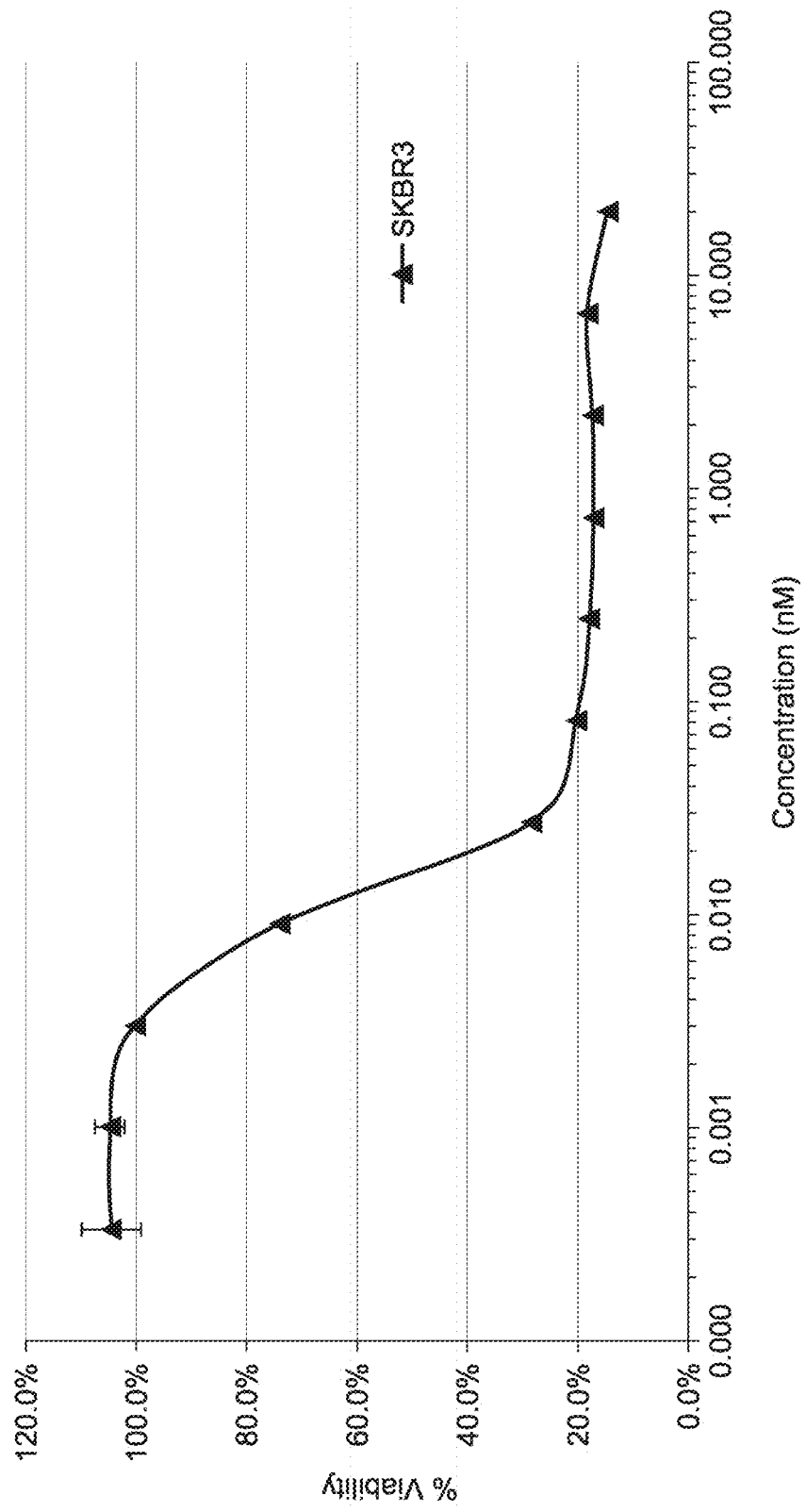
FIG. 12 shows viability of SK-BR-3 cells for a trastuzumab-compound 55 antibody-drug conjugate.

Antibody drug conjugates were the analyzed for cytotoxicity. The cell lines used were SK-BR-3 human breast adenocarcinoma (HER2 triple positive), HCC1954 human Ductal Carcinoma (HER2 triple positive), MCF7 human breast adenocarcinoma (HER2 normal), and MDA-MB-468 human breast adenocarcinoma (HER2 negative). These cells were available from ATCC. SK-BR-3 cells were grown in McCoy's 5 A medium (Caisson Labs, North Logan, Utah) supplemented with 10% fetal bovine serum. HCC1954 cells were grown in RPMI-1640 medium (Caisson Labs, North Logan, Utah) supplemented with 10% fetal bovine serum. MCF7 and MDA-MB-468 cells were grown in DMEM/F12 medium (Caisson Labs, North Logan, Utah) supplemented with 10% fetal bovine serum. SK-BR-3, MCF7, and MDA-MB-468 cells were plated in 96-well plates at approximately 7,500 cells/well, and HCC1954 cells were plated in 96-well plates at approximately 20,000 cells/well. Compounds or the antibody-drug conjugates were added in duplicates in the same day. After 72 hour incubation at 37° C., CellTiter-Glo (Promega, Madison, Wis.) were added and cell viability was determined as describe by the manufacture's protocol. The percent viability was determined as following:

% Viability=Average Luminescence Value of the duplicates(treated wells)/Average Luminescence Value of the untreated wells Trastuzumab and compound 55 were conjugated using a selective conjugation method under the General Conjugation Procedure II. The product of the trastuzumab-compound 55 selective conjugation reaction was analyzed for cytotoxicity on SK-BR-3 cells, as depicted in FIG. 12.

Figure 13:
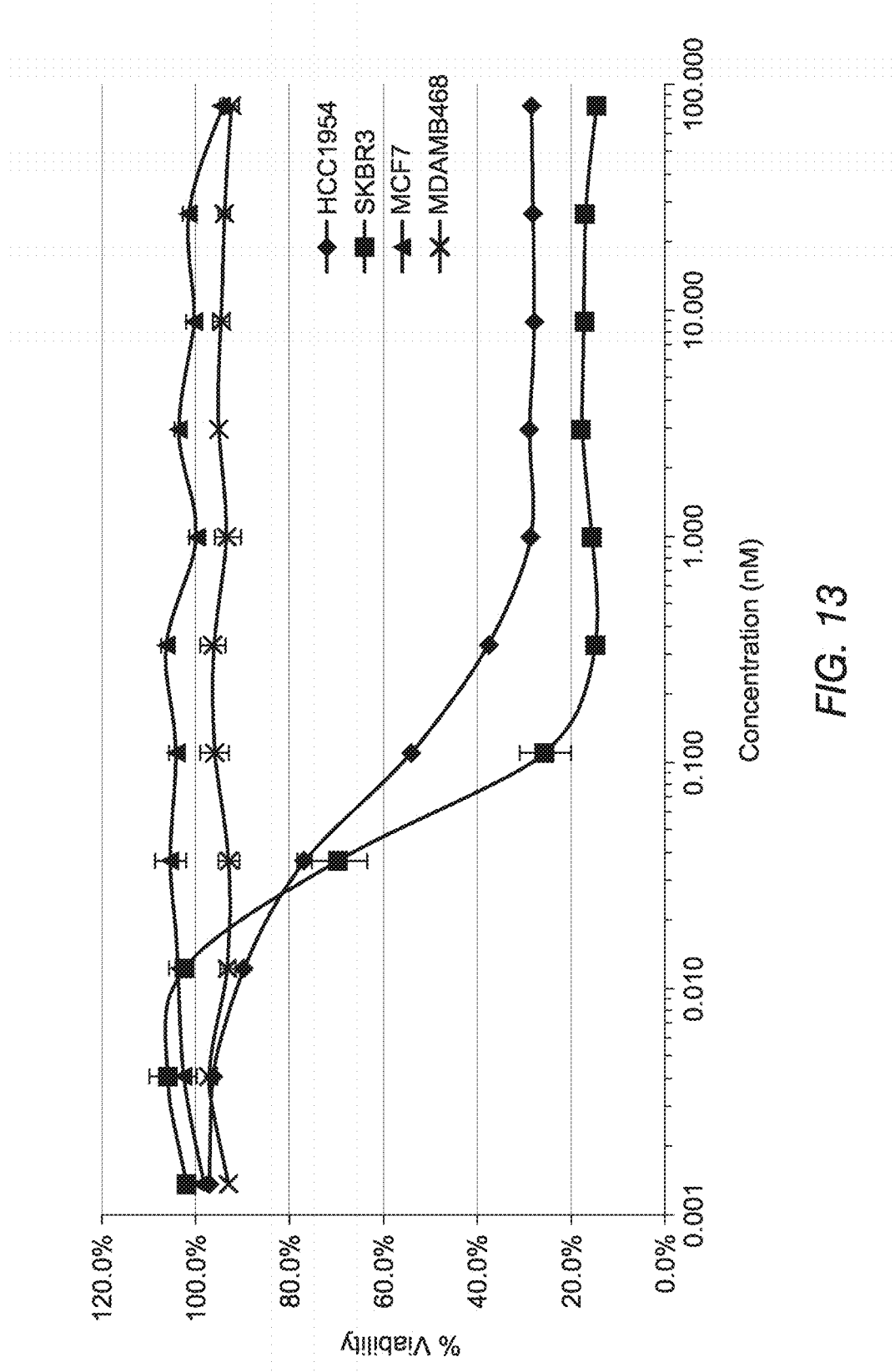
FIG. 13 shows viability of SK-BR-3, HCC1954, MCF7, and MDA-MB-468 cells for a trastuzumab-compound 61 antibody-drug conjugate.

Trastuzumab and compound 61 were conjugated using a selective conjugation method under the General Reaction Conditions General Conjugation Procedure II. The product of the trastuzumab-compound 61 selective conjugation reaction was analyzed for cytotoxicity on SK-BR-3, HCC1954, MCF7, and MDA-MB-468 cells, as depicted in FIG. 13.

Figure 14:
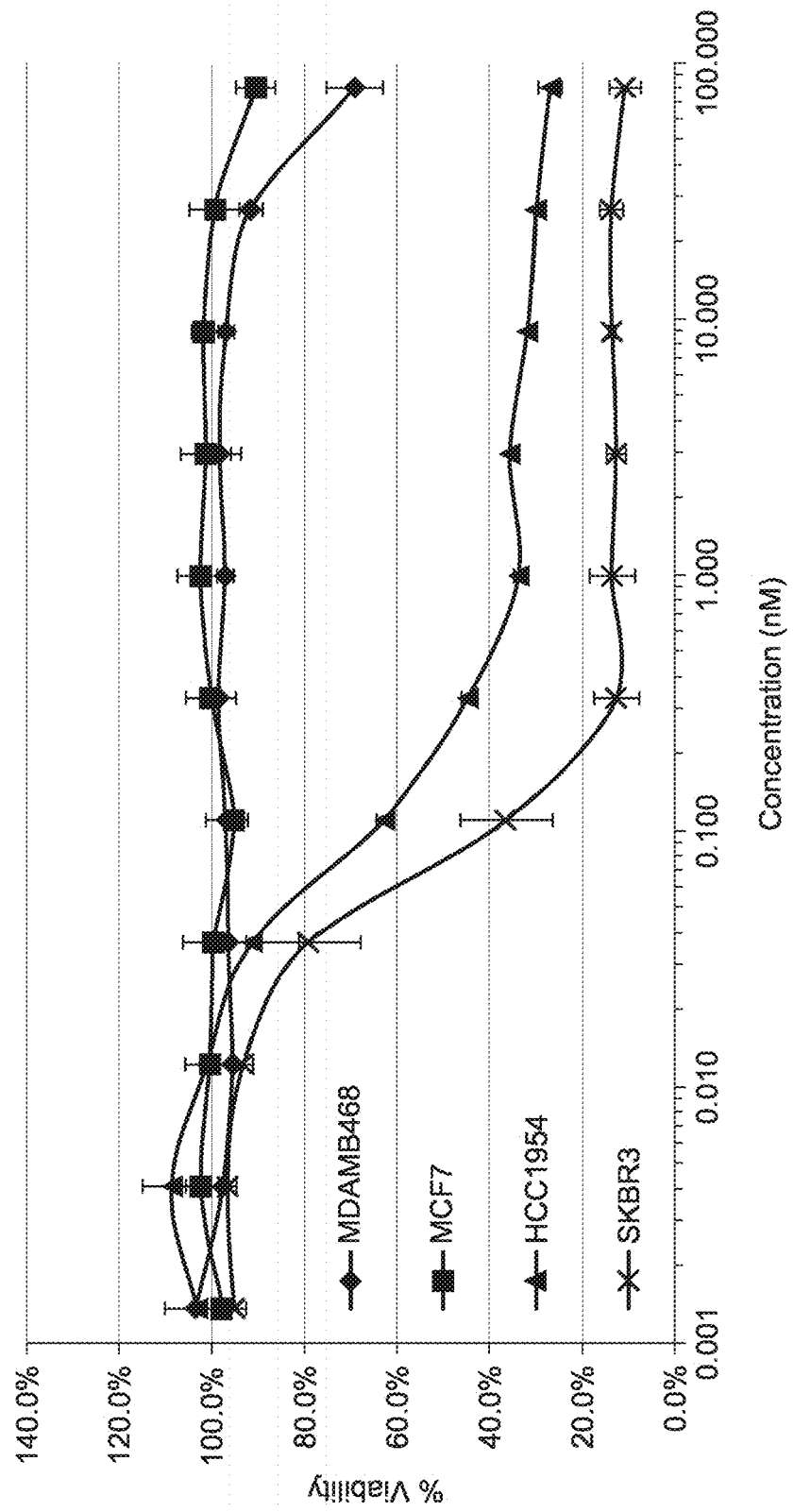
FIG. 14 shows viability of SK-BR-3, HCC1954, MCF7, and MDA-MB-468 cells for a trastuzumab-compound 67 antibody-drug conjugate.

The product of the trastuzumab and compound 67 selective conjugation as described above in regard to FIG. 5 was analyzed for cytotoxicity on SK-BR-3, HCC1954, MCF7, and MDA-MB-468 cells, as depicted in FIG. 14.

Figure 15:
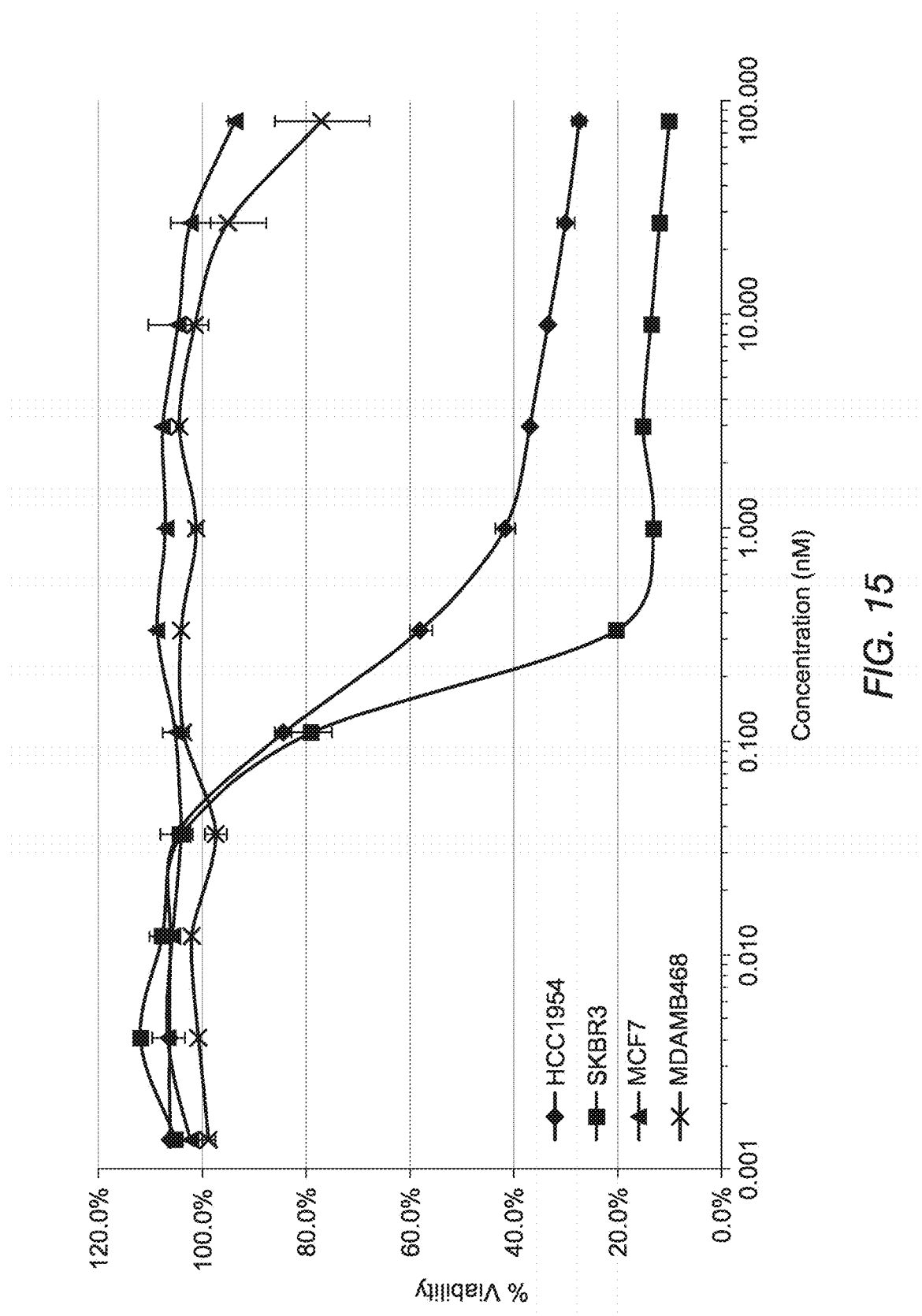
FIG. 15 shows viability of SK-BR-3, HCC1954, MCF7, and MDA-MB-468 cells for a trastuzumab-compound 62 antibody-drug conjugate.

The product of the trastuzumab and compound 62 selective conjugation as described above in regard to FIG. 6 was analyzed for cytotoxicity on SK-BR-3, HCC1954, MCF7, and MDA-MB-468 cells, as depicted in FIG. 15.

Figure 16:
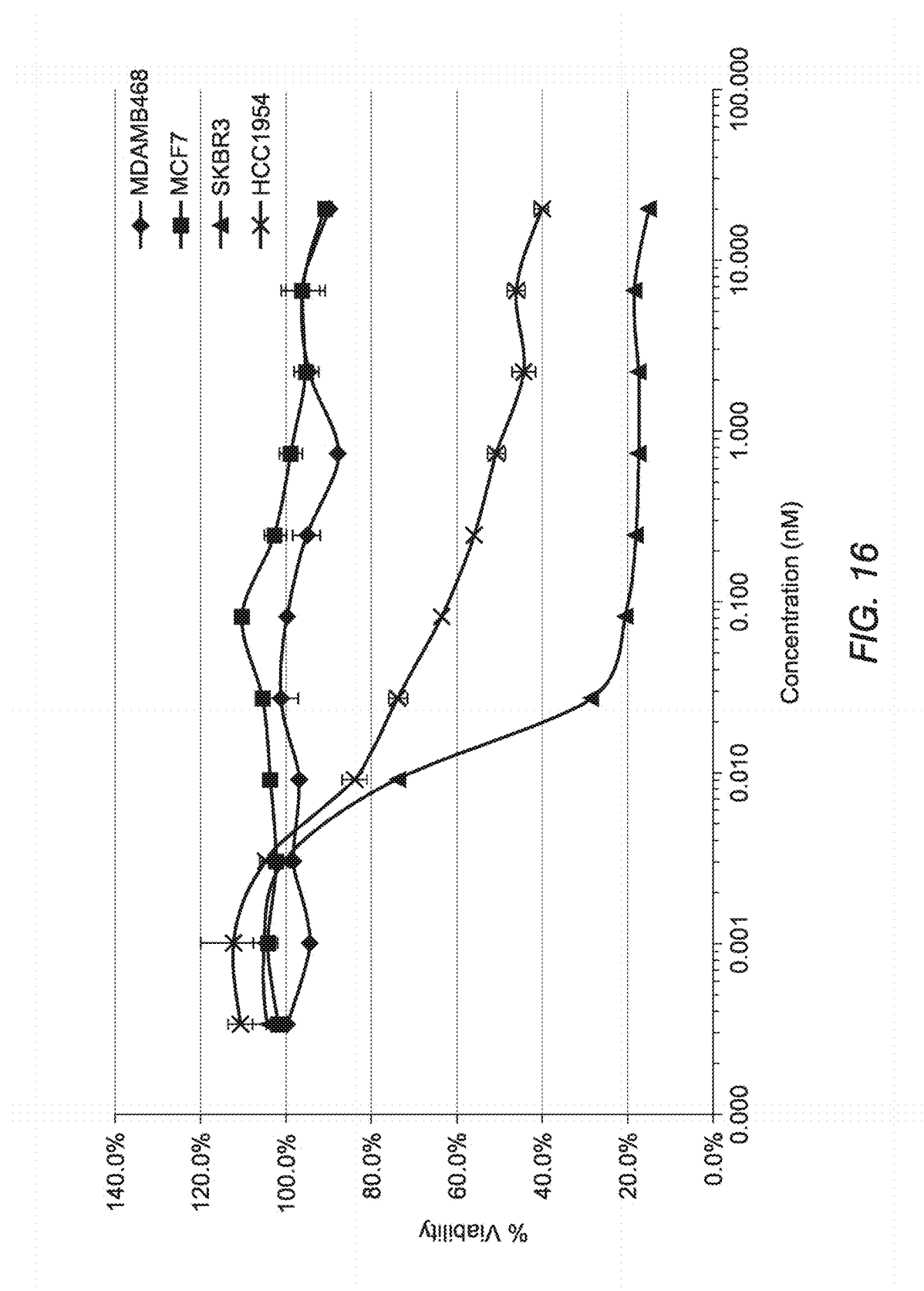
FIG. 16 shows viability of SK-BR-3, HCC1954, MCF7, and MDA-MB-468 cells for a trastuzumab-compound 55 antibody-drug conjugate.

The product of the trastuzumab and compound 55 selective conjugation as described above in regard to FIG. 12 was analyzed for cytotoxicity on SK-BR-3, HCC1954, MCF7, and MDA-MB-468 cells, as depicted in FIG. 16.

What is claimed is:

1. An active agent-conjugate, comprising Formula 1a:

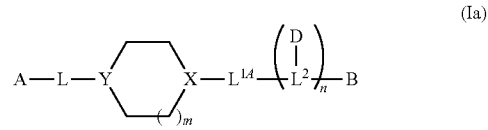

or a pharmaceutically acceptable salt thereof,
wherein:
A is a targeting moiety selected from the group consisting of an antibody and an antibody fragment;
B is null;
X is N;
Y is N;
m is 1;
D is a drug;
$L^2$ is a linker independently selected from the group consisting of —(CH$_2$)$_n$—, —(CH$_2$CH$_2$O)$_n$, D-Val-Leu-Lys, Gly-Gly-Arg, and combinations thereof;
n is 1;
L is —NH—C(=O)—NH; and
$L^{14}$ is a linker selected from the group consisting of —(CH$_2$)$_n$—, —(CH$_2$CH$_2$O)$_n$, D Val-Leu-Lys, and Gly-Gly-Arg, or is null.

2. The active agent-conjugate of claim 1 wherein A is a monoclonal antibody (mAB).

* * * * *